United States Patent
Grether et al.

(10) Patent No.: US 9,593,123 B2
(45) Date of Patent: Mar. 14, 2017

(54) TRIAZOLO[4,5-D]PYRIMIDINE DERIVATIVES

(71) Applicant: Hoffmann-La Roche Inc., Little Falls, NJ (US)

(72) Inventors: Uwe Grether, Efringen-Kirchen (DE); Matthias Nettekoven, Grenzach-Wyhlen (DE); Mark Rogers-Evans, Bottmingen (CH); Stephan Roever, Inzlingen (DE); Sebastien Schmitt, Hagenthal-le-Bas (FR); Atsushi Kimbara, Shizuoka (JP)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/050,753

(22) Filed: Feb. 23, 2016

(65) Prior Publication Data

US 2016/0168158 A1 Jun. 16, 2016

Related U.S. Application Data

(63) Continuation of application No. PCT/EP2014/068640, filed on Sep. 30, 2014.

(30) Foreign Application Priority Data

Sep. 6, 2013 (EP) .................................. 13183385

(51) Int. Cl.
*C07D 487/04* (2006.01)
(52) U.S. Cl.
CPC .................................. *C07D 487/04* (2013.01)
(58) Field of Classification Search
IPC .................................................. C07D 487/04
See application file for complete search history.

(56) References Cited

U.S. PATENT DOCUMENTS 6,245,769 B1 6/2001 Arvanitis et al.

FOREIGN PATENT DOCUMENTS

| WO | 01/58869 A2 | 8/2001 |
| WO | 2006/047516 A2 | 5/2006 |
| WO | 2008/141239 A1 | 11/2008 |
| WO | 2009/117444 A1 | 9/2009 |
| WO | 2010/120987 A1 | 10/2010 |
| WO | 2013/060837 A1 | 2/2013 |
| WO | 2013/068306 A1 | 5/2013 |
| WO | 2013/076182 A1 | 5/2013 |
| WO | 2014/005968 A1 | 1/2014 |
| WO | 2014/086705 A1 | 6/2014 |
| WO | 2014/086805 A1 | 6/2014 |
| WO | 2014/086806 A1 | 6/2014 |
| WO | 2014/086807 | 6/2014 |
| WO | 2014/135507 A1 | 9/2014 |
| WO | 2014/177490 A1 | 11/2014 |
| WO | 2014/177527 A1 | 11/2014 |
| WO | 2014/198592 A1 | 12/2014 |

OTHER PUBLICATIONS

David Kinshuck Drugs to treat diabetic retinopathy Sep. 15, 2016.*
Walker et al. High Throughput Screens Yield . . . PLOS Neglated Tropical disease 5(4):e1033.*
Chorvat et al., "Synthesis, Corticotropin-Releasing Factor Receptor Binding Affinity and Pharmacokinetic Properties of Triazolo-, Imidazo-, and Pyrrolopyrimidines and -pyridines" J. Med. Chem. 42(5):833-848.
ISR for WO 2015/032769, PCT/EP2014/068640.
Kang et al., "Tetrazole-biarylpyrazole derivatives as cannabinoid CBI receptor antagonists" Biorg Med Chem Lett 18:2385-2389 ( 2008).
Nettekoven et al., "Highly potent and selective cannabinoid receptor 2 agonists: initial hit optimization of an adamantyl hit series identified from high-through-put screening" Bioorg Med Chem Lett 23:1177-1181 ( 2013).
Nettekoven et al., "Novel Triazolopyrimidine-Derived Cannabinoid Receptor 2 Agonists as Potential Treatment for Inflammatory Kidney Diseases" ChemMedChem 11(2):179-89 ( 2016).
Roderick et al., "High Throughput Screens Yield Small Molecule Inhibitors of Leishmania CRK3:CYC6 Cyclin-Dependent Kinase" PLOS Neglected Tropical Diseases 5(4):e1033 (Apr. 5, 2011).
Shealy et al., "v-Triazolo [4,5-d]pyrimidines. III. N-(3-Alkyl-5-amino-3H-2j-triazolo[4,5-d]pyrimidin-7-yl)-amino Acids" J. Med. Chem. 9(3):417-419 ( 1966).

* cited by examiner

*Primary Examiner* — Shirley V Gembeh
(74) *Attorney, Agent, or Firm* — Alex Andrus

(57) ABSTRACT

The invention relates to a compound of formula (I)

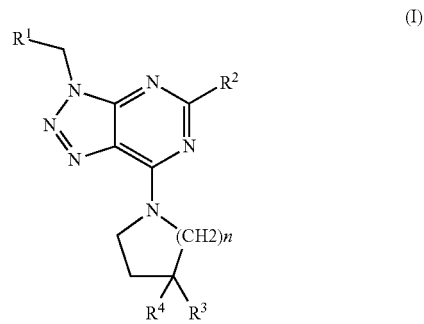

wherein $R^1$ to $R^4$ are defined as in the description and in the claims. The compound of formula (I) can be used as a medicament.

14 Claims, No Drawings

TRIAZOLO[4,5-D]PYRIMIDINE DERIVATIVES

CROSS REFERENCE TO RELATED APPLICATIONS

This application is a continuation of International Application No. PCT/EP2014/068640 having an International Filing Date of 3 Sep. 2014, the entire contents of which are incorporated herein by reference, and which claims the benefit of priority under 35 U.S.C. §119 to EP 13183385.7, filed 6 Sep. 2013.

FIELD OF THE INVENTION

The present invention relates to organic compounds useful for therapy and/or prophylaxis in a mammal, and in particular to compounds that are preferential agonists of the Cannabinoid Receptor 2.

SUMMARY OF THE INVENTION

The invention relates in particular to a compound of formula (I)

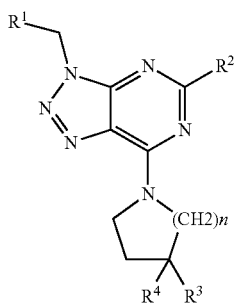

wherein $R^1$ is haloalkyl, halophenyl, alkoxyphenyl, alkyl-1,2,5-oxadiazolyl, haloalkylphenyl, alkyl sulfonylphenyl, halopyridinyl or alkyltetrazolyl;

$R^2$ is cycloalkyl, isopropyl, alkenyl, piperidinyl, alkylamino, azetidinyl, pyrrolidinyl, alkoxy, cycloalkylalkoxy, cycloalkyloxy, oxetanyloxy, alkyloxetanylalkyloxy, alkynyloxy, alkoxyalkoxy, hydroxyalkyloxy, alkylsulfanyl, haloalkylsulfanyl, alkylsulfonyl, hydroxyalkylsulfanyl, hydroxyalkylsulfonyl or alkoxyalkylsulfonyl;

$R^3$ and $R^4$ are independently selected from hydrogen, halogen, hydroxyl, alkylcarbonylamino and alkyl, provided that $R^3$ and $R^4$ are not both hydrogen at the same time; and n is 1 or 2;

or a pharmaceutically acceptable salt or ester thereof;

provided that (S)-1-[3-(4-Methoxy-benzyl)-5-(2,2,2-trifluoro-ethoxy)-3H-[1,2,3]triazolo[4,5-d]pyrimidin-7-yl]-pyrrolidin-3-ol is excluded.

The compound of formula (I) is particularly useful in the treatment or prophylaxis of e.g. pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis.

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

The interest in CB2 receptor agonists has been steadily on the rise during the last decade (currently 30-40 patent applications/year) due to the fact that several of the early compounds have been shown to have beneficial effects in pre-clinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemic preconditioning.

Recent data indicates that endocannabinnoids and their receptors, in particular CB2 might be involved in preconditioning and contribute to prevent reperfusion injury by downregulation of the inflammatory response (Pacher, P. et al. Br J Pharmacol 2008, 153(2), 252-62). Specifically, recent studies using CB2 tool agonists demonstrated the efficacy of this concept for reducing the I/R injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in sub-chronic and chronic setting. Specific upregulation of CB1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A. et al. Arthritis Rheum 2009, 60(4), 1129-36) and in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

The compounds of the invention bind to and modulate the CB2 receptor and have lower CB1 receptor activity.

DEFINITIONS

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls. Particular examples of alkyl are methyl, ethyl, n-propyl, isopropyl, n.-butyl, isobutyl, tert.-butyl, and neopentyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. Particular examples of "cycloalkyl" are cyclopropyl and cyclobutyl.

The term "alkenyl", alone or in combination, signifies a straight-chain or branched hydrocarbon residue comprising an olefinic bond and up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "alkynyl", alone or in combination, signifies a straight-chain or branched hydrocarbon residue comprising a triple bond and up to 8, preferably up to 6, particularly preferred up to 4 carbon atoms. A particular example of alkynyl group is propinyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert.-butoxy. Particular "alkoxy" are methoxy, ethoxy, n-propyloxy, isopropyloxy, isobutyloxy, tert.-butyloxy and neopentyloxy.

The terms "halogen" or "halo", alone or in combination, signifies fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to four halogens, i.e. one, two, three or four halogens. Particular "halogen" are fluorine, chlorine and bromine.

The term "haloalkyl", alone or in combination, denotes an alkyl group substituted with at least one halogen, particularly substituted with one to five halogens, particularly one to three halogens. Particular "haloalkyl" are trifluoromethyl, trifluoroethyl and trifluoropropyl.

The term "haloalkyloxy" or "haloalkoxy", alone or in combination, denotes an alkyloxy group substituted with at least one halogen, particularly substituted with one to five halogens, particularly one to three halogens. Particular "haloalkyloxy" are trifluoroethyloxy, trifluoropropyloxy, fluoroethyloxy, difluoroethyloxy and difluoropropyloxy.

The terms "hydroxyl" and "hydroxy", alone or in combination, signify the —OH group.

The term "oxy", alone or in combination, signifies the —O— group.

The term "amino", alone or in combination, signifies the primary amino group (—$NH_2$), the secondary amino group (—NH—), or the tertiary amino group (—N—). A particular amino is —NH—.

The term "sulfonyl", alone or in combination, signifies the —$S(O)_2$— group.

The term "sulfanyl", alone or in combination, signifies the —S— group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that the compound of general formula (I) may be derivatized at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compound of general formula (I), similar to the metabolically labile esters, which are capable of producing the parent compound of general formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3$^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethyl silylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

DETAILED DESCRIPTION OF EXEMPLARY EMBODIMENTS

The invention relates in particular to:

A compound of formula (I) wherein $R^1$ is halophenyl, alkoxyphenyl, alkyl-1,2,5-oxadiazolyl, haloalkylphenyl, alkylsulfonylphenyl, halopyridinyl or alkyltetrazolyl;

A compound of formula (I) wherein $R^1$ is halophenyl, haloalkylphenyl or alkyl sulfonylphenyl;

A compound of formula (I) wherein $R^1$ is chlorophenyl, trifluoromethylphenyl or methyl sulfonylphenyl;

A compound of formula (I) wherein $R^2$ is cycloalkyl, isopropyl, alkylamino, alkoxy, haloalkyloxy or alkylsulfanyl;

A compound of formula (I) wherein $R^2$ is cyclobutyl, isopropyl, tert.-butylamino, pentyloxy, isopropyloxy, trifluoroethyloxy, trifluoropropyloxy, ethylsulfanyl or tert.-butylsulfanyl;

A compound of formula (I) wherein $R^3$ and $R^4$ are independently selected from hydrogen, halogen and hydroxyl;

A compound of formula (I) wherein one of $R^3$ and $R^4$ is hydrogen and the other one is hydroxyl, or wherein $R^3$ and $R^4$ are both halogen at the same time; and A compound of formula (I) wherein one of $R^3$ and $R^4$ is hydrogen and the other one is hydroxyl, or wherein $R^3$ and $R^4$ are both fluorine at the same time.

The invention further relates in particular to a compound of formula (I) selected from:
3-[(2-chlorophenyl)methyl]-5-cyclobutyl-7-(3,3-difluoropyrrolidin-1-yl)triazolo[4,5-d]pyrimidine;
5-cyclopropyl-7-(3,3-difluoropyrrolidin-1-yl)-3-[(4-methoxyphenyl)methyl]triazolo[4,5-d]pyrimidine;
3-[(2-chlorophenyl)methyl]-7-(3,3-difluoropyrrolidin-1-yl)-5-propan-2-yltriazolo[4,5-d]pyrimidine;
3-[(2-chlorophenyl)methyl]-5-cyclopropyl-7-(3,3-difluoropyrrolidin-1-yl)triazolo[4,5-d]pyrimidine;
3-[[5-cyclopropyl-7-(3,3-difluoropyrrolidin-1-yl)triazolo[4,5-d]pyrimidin-3-yl]methyl]-4-methyl-1,2,5-oxadiazole;
(3S)-1-[3-[(2-chlorophenyl)methyl]-5-prop-1-en-2-yltriazolo[4,5-d]pyrimidin-7-yl]pyrrolidin-3-ol;
3-[(2-chlorophenyl)methyl]-5,7-di(piperidin-1-yl)triazolo[4,5-d]pyrimidine;
3-[(2-chlorophenyl)methyl]-7-(3,3-difluoropyrrolidin-1-yl)-N-ethyltriazolo[4,5-d]pyrimidin-5-amine;
5-(azetidin-1-yl)-3-[(2-chlorophenyl)methyl]-7-(3,3-difluoropyrrolidin-1-yl)triazolo[4,5-d]pyrimidine;
3-[(2-chlorophenyl)methyl]-7-(3,3-difluoropyrrolidin-1-yl)-5-pyrrolidin-1-yltriazolo[4,5-d]pyrimidine;
3-[(2-chlorophenyl)methyl]-N-cyclobutyl-7-(3,3-difluoropyrrolidin-1-yl)triazolo[4,5-d]pyrimidin-5-amine;
N-tert-butyl-3-[(2-chlorophenyl)methyl]-7-(3,3-difluoropyrrolidin-1-yl)triazolo[4,5-d]pyrimidin-5-amine;
3-[(2-chlorophenyl)methyl]-7-(3,3-difluoropyrrolidin-1-yl)-N-(3-methyloxetan-3-yl)triazolo[4,5-d]pyrimidin-5-amine;
4-[3-[(2-chlorophenyl)methyl]-7-(3,3-difluoropyrrolidin-1-yl)triazolo[4,5-d]pyrimidin-5-yl]morpholine;
N-tert-butyl-3-[(2-chlorophenyl)methyl]-7-(3,3-difluoropyrrolidin-1-yl)-N-methyltriazolo[4,5-d]pyrimidin-5-amine;
3-[(2-chlorophenyl)methyl]-7-(3,3-difluoropyrrolidin-1-yl)-N-(2,2-dimethylpropyl)triazolo[4,5-d]pyrimidin-5-amine;
3-[(2-chlorophenyl)methyl]-7-(3,3-difluoropyrrolidin-1-yl)-N-(oxetan-3-yl)triazolo[4,5-d]pyrimidin-5-amine;
3-[(2-chlorophenyl)methyl]-N-cyclobutyl-7-(3,3-difluoropyrrolidin-1-yl)-N-methyltriazolo[4,5-d]pyrimidin-5-amine;
(3S)-1-[5-(tert-butylamino)-3-[(4-methoxyphenyl)methyl]triazolo[4,5-d]pyrimidin-7-yl]pyrrolidin-3-ol;
N-tert-butyl-7-(3,3-difluoropyrrolidin-1-yl)-3-[(4-methoxyphenyl)methyl]triazolo[4,5-d]pyrimidin-5-amine;
N-[(3S)-1-[5-(tert-butylamino)-3-[(4-methoxyphenyl)methyl]triazolo[4,5-d]pyrimidin-7-yl]pyrrolidin-3-yl]acetamide;
N-tert-butyl-7-(3,3-difluoropyrrolidin-1-yl)-3-[[2-(trifluoromethyl)phenyl]methyl]triazolo[4,5-d]pyrimidin-5-amine;
N-tert-butyl-7-(3,3-difluoropyrrolidin-1-yl)-3-[(2-methylsulfonylphenyl)methyl]triazolo[4,5-d]pyrimidin-5-amine;
N-tert-butyl-3-[(3-chloropyridin-2-yl)methyl]-7-(3,3-difluoropyrrolidin-1-yl)triazolo[4,5-d]pyrimidin-5-amine;

N-tert-butyl-7-(3,3-difluoropyrrolidin-1-yl)-3-[(1-methyl-tetrazol-5-yl)methyl]triazolo[4,5-d]pyrimidin-5-amine;

N-tert-butyl-7-(3,3-difluoropyrrolidin-1-yl)-3-[(4-methyl-1,2,5-oxadiazol-3-yl)methyl]triazolo[4,5-d]pyrimidin-5-amine;

N-[(3S)-1-[5-(tert-butylamino)-3-[(3-chloropyridin-2-yl)methyl]triazolo[4,5-d]pyrimidin-7-yl]pyrrolidin-3-yl]acetamide;

(3S)-1-[5-(tert-butylamino)-3-[(2-chlorophenyl)methyl]triazolo[4,5-d]pyrimidin-7-yl]pyrrolidin-3-ol;

(3S)-1-[5-(tert-butylamino)-3-[(1-methyltetrazol-5-yl)methyl]triazolo[4,5-d]pyrimidin-7-yl]pyrrolidin-3-ol;

(3S)-1-[5-(tert-butylamino)-3-[(4-methoxyphenyl)methyl]triazolo[4,5-d]pyrimidin-7-yl]-3-methylpyrrolidin-3-ol;

(3R)-1-[5-(tert-butylamino)-3-[(4-methoxyphenyl)methyl]triazolo[4,5-d]pyrimidin-7-yl]-3-methylpyrrolidin-3-ol;

(3S)-1-[3-[(2-chlorophenyl)methyl]-5-morpholin-4-yltriazolo[4,5-d]pyrimidin-7-yl]-3-methylpyrrolidin-3-ol;

(3S)-3-methyl-1-[5-morpholin-4-yl-3-[[2-(trifluoromethyl)phenyl]methyl]triazolo[4,5-d]pyrimidin-7-yl]pyrrolidin-3-ol;

(3S)-1-[3-[(3-chloropyridin-2-yl)methyl]-5-morpholin-4-yltriazolo[4,5-d]pyrimidin-7-yl]-3-methylpyrrolidin-3-ol;

(3S)-3-methyl-1-[3-[(3-methyl-1,2,4-oxadiazol-5-yl)methyl]-5-morpholin-4-yltriazolo[4,5-d]pyrimidin-7-yl]pyrrolidin-3-ol;

(3R)-1-[3-[(2-chlorophenyl)methyl]-5-morpholin-4-yltriazolo[4,5-d]pyrimidin-7-yl]-3-methylpyrrolidin-3-ol;

(3R)-3-methyl-1-[5-morpholin-4-yl-3-[[2-(trifluoromethyl)phenyl]methyl]triazolo[4,5-d]pyrimidin-7-yl]pyrrolidin-3-ol;

(3R)-3-methyl-1-[3-[(2-methylsulfonylphenyl)methyl]-5-morpholin-4-yltriazolo[4,5-d]pyrimidin-7-yl]pyrrolidin-3-ol;

(3R)-3-methyl-1-[3-[(3-methyl-1,2,4-oxadiazol-5-yl)methyl]-5-morpholin-4-yltriazolo[4,5-d]pyrimidin-7-yl]pyrrolidin-3-ol;

3-[(2-chlorophenyl)methyl]-7-(3,3-difluoropyrrolidin-1-yl)-5-(2,2,2-trifluoroethoxy)triazolo[4,5-d]pyrimidine;

3-[(2-chlorophenyl)methyl]-7-(3,3-difluoropyrrolidin-1-yl)-5-(1,1,1-trifluoropropan-2-yloxy)triazolo[4,5-d]pyrimidine;

3-[(2-chlorophenyl)methyl]-7-(3,3-difluoropyrrolidin-1-yl)-5-[(2S)-1,1,1-trifluoropropan-2-yl]oxytriazolo[4,5-d]pyrimidine;

3-[(2-chlorophenyl)methyl]-5-(2,2-difluoroethoxy)-7-(3,3-difluoropyrrolidin-1-yl)triazolo[4,5-d]pyrimidine;

3-[(2-chlorophenyl)methyl]-7-(3,3-difluoropyrrolidin-1-yl)-5-ethoxytriazolo[4,5-d]pyrimidine;

5-butoxy-3-[(2-chlorophenyl)methyl]-7-(3,3-difluoropyrrolidin-1-yl)triazolo[4,5-d]pyrimidine;

3-[(2-chlorophenyl)methyl]-7-(3,3-difluoropyrrolidin-1-yl)-5-(2-fluoroethoxy)triazolo[4,5-d]pyrimidine;

3-[(2-chlorophenyl)methyl]-5-(cyclopropylmethoxy)-7-(3,3-difluoropyrrolidin-1-yl)triazolo[4,5-d]pyrimidine;

3-[(2-chlorophenyl)methyl]-5-cyclobutyloxy-7-(3,3-difluoropyrrolidin-1-yl)triazolo[4,5-d]pyrimidine;

3-[(2-chlorophenyl)methyl]-7-(3,3-difluoropyrrolidin-1-yl)-5-(oxetan-3-yloxy)triazolo[4,5-d]pyrimidine;

3-[(2-chlorophenyl)methyl]-7-(3,3 difluoropyrrolidin-1-yl)-5[(3-methyloxetan-3-yl)methoxy]triazolo[4,5-d]pyrimidine;

3-[(2-chlorophenyl)methyl]-7-(3,3-difluoropyrrolidin-1-yl)-5-[(2R)-1,1,1-trifluoropropan-2-yl]oxytriazolo[4,5-d]pyrimidine;

3-[(2-chlorophenyl)methyl]-7-(3,3-difluoropyrrolidin-1-yl)-5-(2,2-dimethylpropoxy)triazolo[4,5-d]pyrimidine;

3-[(2-chlorophenyl)methyl]-5-(2,2-difluoropropoxy)-7-(3,3-difluoropyrrolidin-1-yl)triazolo[4,5-d]pyrimidine;

3-[(2-chlorophenyl)methyl]-7-(3,3-difluoropyrrolidin-1-yl)-5-(2-methylpropoxy)triazolo[4,5-d]pyrimidine;

3-[(2-chlorophenyl)methyl]-7-(3,3-difluoropyrrolidin-1-yl)-5-propan-2-yloxytriazolo[4,5-d]pyrimidine;

3-[(2-chlorophenyl)methyl]-7-(3,3-difluoropyrrolidin-1-yl)-5-prop-2-ynoxytriazolo[4,5-d]pyrimidine;

3-[(2-chlorophenyl)methyl]-7-(3,3-difluoropyrrolidin-1-yl)-5-(1-methoxypropan-2-yloxy)triazolo[4,5-d]pyrimidine;

1-[3-[(2-chlorophenyl)methyl]-7-(3,3-difluoropyrrolidin-1-yl)triazolo[4,5-d]pyrimidin-5-yl]oxy-2-methylpropan-2-ol;

3-[(2-chlorophenyl)methyl]-7-(3,3-difluoropyrrolidin-1-yl)-5-propoxytriazolo[4,5-d]pyrimidine;

(3S)-1-[3-[(2-chlorophenyl)methyl]-5-(2,2,2-trifluoroethoxy)triazolo[4,5-d]pyrimidin-7-yl]pyrrolidin-3-ol;

(3S)-1-[5-(2,2,2-trifluoroethoxy)-3-[[2-(trifluoromethyl)phenyl]methyl]triazolo[4,5-d]pyrimidin-7-yl]pyrrolidin-3-ol;

(3S)-1-[3-[(2-chlorophenyl)methyl]-5-propan-2-yloxytriazolo[4,5-d]pyrimidin-7-yl]pyrrolidin-3-ol;

(3S)-1-[3-[(2-methylsulfonylphenyl)methyl]-5-propan-2-yloxytriazolo[4,5-d]pyrimidin-7-yl]pyrrolidin-3-ol;

(3S)-1-[3-[(1-methyltetrazol-5-yl)methyl]-5-propan-2-yloxytriazolo[4,5-d]pyrimidin-7-yl]pyrrolidin-3-ol;

7-(3,3-difluoropyrrolidin-1-yl)-5-(2,2-dimethylpropoxy)-3-[(1-methyltetrazol-5-yl)methyl]triazolo[4,5-d]pyrimidine;

7-(3,3-difluoropyrrolidin-1-yl)-5-(2,2-dimethylpropoxy)-3-[(2-methylsulfonylphenyl)methyl]triazolo[4,5-d]pyrimidine;

3-[[7-(3,3-difluoropyrrolidin-1-yl)-5-(2,2-dimethylpropoxy)triazolo[4,5-d]pyrimidin-3-yl]methyl]-4-methyl-1,2,5-oxadiazole;

7-(3,3-difluoropyrrolidin-1-yl)-3-[[2-(trifluoromethyl)phenyl]methyl]-5-[(2S)-1,1,1-trifluoropropan-2-yl]oxytriazolo[4,5-d]pyrimidine;

7-(3,3-difluoropyrrolidin-1-yl)-3-[(2-methylsulfonylphenyl)methyl]-5-[(2S)-1,1,1-trifluoropropan-2-yl]oxytriazolo[4,5-d]pyrimidine;

3-[(3-chloropyridin-2-yl)methyl]-7-(3,3-difluoropyrrolidin-1-yl)-5-[(2S)-1,1,1-trifluoropropan-2-yl]oxytriazolo[4,5-d]pyrimidine;

2-[[7-(3,3-difluoropyrrolidin-1-yl)-5-[(2S)-1,1,1-trifluoropropan-2-yl]oxytriazolo[4,5-d]pyrimidin-3-yl]methyl]-5-methyl-1,3,4-oxadiazole;

5-[[7-(3,3-difluoropyrrolidin-1-yl)-5-[(2S)-1,1,1-trifluoropropan-2-yl]oxytriazolo[4,5-d]pyrimidin-3-yl]methyl]-3-methyl-1,2,4-oxadiazole;

7-(3,3-difluoropyrrolidin-1-yl)-3-[(1-methyltetrazol-5-yl)methyl]-5-[(2S)-1,1,1-trifluoropropan-2-yl]oxytriazolo[4,5-d]pyrimidine;

3-[[7-(3,3-difluoropyrrolidin-1-yl)-5-[(2S)-1,1,1-trifluoropropan-2-yl]oxytriazolo[4,5-d]pyrimidin-3-yl]methyl]-4-methyl-1,2,5-oxadiazole;

7-(3,3-difluoropyrrolidin-1-yl)-5-[(2S)-1,1,1-trifluoropropan-2-yl]oxy-3-(3,3,3-trifluoropropyl)triazolo[4,5-d]pyrimidine;

3-[(1-cyclopropyltetrazol-5-yl)methyl]-7-(3,3-difluoropyrrolidin-1-yl)-5-[(2S)-1,1,1-trifluoropropan-2-yl]oxytriazolo[4,5-d]pyrimidine;

N-[(3S)-1-[3-[(2-chlorophenyl)methyl]-5-(2,2-dimethylpropoxy)triazolo[4,5-d]pyrimidin-7-yl]pyrrolidin-3-yl]acetamide;

N-[(3S)-1-[3-[(3-chloropyridin-2-yl)methyl]-5-(2,2-dimethylpropoxy)triazolo[4,5-d]pyrimidin-7-yl]pyrrolidin-3-yl]acetamide;
N-[(3S)-1-[5-(2,2-dimethylpropoxy)-3-[(4-methyl-1,2,5-oxadiazol-3-yl)methyl]triazolo[4,5-d]pyrimidin-7-yl]pyrrolidin-3-yl]acetamide;
N-[(3S)-1-[3-[(2-chlorophenyl)methyl]-5-[(2S)-1,1,1-trifluoropropan-2-yl]oxytriazolo[4,5-d]pyrimidin-7-yl]pyrrolidin-3-yl]acetamide;
N-[(3S)-1-[3-[[2-(trifluoromethyl)phenyl]methyl]-5-[(2S)-1,1,1-trifluoropropan-2-yl]oxytriazolo[4,5-d]pyrimidin-7-yl]pyrrolidin-3-yl]acetamide;
3-[(2-chlorophenyl)methyl]-7-(3,3-difluoropyrrolidin-1-yl)-5-ethylsulfanyltriazolo[4,5-d]pyrimidine;
3-[(2-chlorophenyl)methyl]-7-(3,3-difluoropyrrolidin-1-yl)-5-(2,2,2-trifluoroethyl sulfanyl)triazolo[4,5-d]pyrimidine;
3-[(2-chlorophenyl)methyl]-7-(3,3-difluoropyrrolidin-1-yl)-5-propan-2-ylsulfanyltriazolo[4,5-d]pyrimidine;
5-tert-butylsulfanyl-3-[(2-chlorophenyl)methyl]-7-(3,3-difluoropyrrolidin-1-yl)triazolo[4,5-d]pyrimidine;
3-[(2-chlorophenyl)methyl]-7-(3,3-difluoropyrrolidin-1-yl)-5-ethylsulfonyltriazolo[4,5-d]pyrimidine;
5-benzylsulfonyl-3-[(2-chlorophenyl)methyl]-7-(3,3-difluoropyrrolidin-1-yl)triazolo[4,5-d]pyrimidine;
3-[(2-chlorophenyl)methyl]-7-(3,3-difluoropyrrolidin-1-yl)-5-propan-2-ylsulfonyltriazolo[4,5-d]pyrimidine;
2-[3-[(2-chlorophenyl)methyl]-7-(3,3-difluoropyrrolidin-1-yl)triazolo[4,5-d]pyrimidin-5-yl]sulfanylethanol;
1-[3-[(2-chlorophenyl)methyl]-7-(3,3-difluoropyrrolidin-1-yl)triazolo[4,5-d]pyrimidin-5-yl]sulfanylpropan-2-ol;
5-butylsulfanyl-3-[(2-chlorophenyl)methyl]-7-(3,3-difluoropyrrolidin-1-yl)triazolo[4,5-d]pyrimidine;
3-[(2-chlorophenyl)methyl]-7-(3,3-difluoropyrrolidin-1-yl)-5-(2-methylpropylsulfanyl)triazolo[4,5-d]pyrimidine;
5-butylsulfonyl-3-[(2-chlorophenyl)methyl]-7-(3,3-difluoropyrrolidin-1-yl)triazolo[4,5-d]pyrimidine;
3-[(2-chlorophenyl)methyl]-7-(3,3-difluoropyrrolidin-1-yl)-5-(2-methylpropylsulfonyl)triazolo[4,5-d]pyrimidine;
1-[3-[(2-chlorophenyl)methyl]-7-(3,3-difluoropyrrolidin-1-yl)triazolo[4,5-d]pyrimidin-5-yl]sulfonylpropan-2-ol;
3-[(2-chlorophenyl)methyl]-7-(3,3-difluoropyrrolidin-1-yl)-5-(2-methoxyethyl sulfonyl)triazolo[4,5-d]pyrimidine; and
N-[(3S)-1-[5-(tert-butylamino)-3-[(2-chlorophenyl)methyl]triazolo[4,5-d]pyrimidin-7-yl]pyrrolidin-3-yl]acetamide.

The invention further relates in particular to a compound of formula (I) selected from:
3-[(2-chlorophenyl)methyl]-5-cyclobutyl-7-(3,3-difluoropyrrolidin-1-yl)triazolo[4,5-d]pyrimidine;
3-[(2-chlorophenyl)methyl]-7-(3,3-difluoropyrrolidin-1-yl)-5-propan-2-yltriazolo[4,5-d]pyrimidine;
N-tert-butyl-3-[(2-chlorophenyl)methyl]-7-(3,3-difluoropyrrolidin-1-yl)triazolo[4,5-d]pyrimidin-5-amine;
N-tert-butyl-7-(3,3-difluoropyrrolidin-1-yl)-3-[(2-methylsulfonylphenyl)methyl]triazolo[4,5-d]pyrimidin-5-amine;
3-[(2-chlorophenyl)methyl]-7-(3,3-difluoropyrrolidin-1-yl)-5-(2,2-dimethylpropoxy)triazolo[4,5-d]pyrimidine;
3-[(2-chlorophenyl)methyl]-7-(3,3-difluoropyrrolidin-1-yl)-5-(2-methylpropoxy)triazolo[4,5-d]pyrimidine;
(3S)-1-[3-[(2-chlorophenyl)methyl]-5-(2,2,2-trifluoroethoxy)triazolo[4,5-d]pyrimidin-7-yl]pyrrolidin-3-ol;
7-(3,3-difluoropyrrolidin-1-yl)-3-[[2-(trifluoromethyl)phenyl]methyl]-5-[(2S)-1,1,1-trifluoropropan-2-yl]oxytriazolo[4,5-d]pyrimidine;
3-[(2-chlorophenyl)methyl]-7-(3,3-difluoropyrrolidin-1-yl)-5-ethylsulfanyltriazolo[4,5-d]pyrimidine; and
5-tert-butylsulfanyl-3-[(2-chlorophenyl)methyl]-7-(3,3-difluoropyrrolidin-1-yl)triazolo[4,5-d]pyrimidine.

In the definition of $R^2$, haloalkyloxy is in particular trifluoroethyloxy, trifluoropropyloxy, difluoroethyloxy, fluoroethyloxy or difluoropropyloxy, and in particular trifluoropropyloxy, difluoroethyloxy, fluoroethyloxy or difluoropropyloxy.

ABBREVIATIONS

In the present description the following abbreviations are used:
MS=mass spectrometry; EI=electron ionization; ESI=electrospray; NMR=nuclear magnetic resonance; DBU=1,8-Diazabicyclo[5.4.0]undec-7-en; DCM=dichloromethane; DEAD=diethyl azodicarboxylate; DIAD=diisopropyl azodicarboxylate; DIPEA=diisopropylethyl amine; DMA=diemthylacetamide; DMF=dimethylformamide; DMSO=dimethyl-sulfoxide; dppf=1,1'-bis(diphenylphosphino)ferrocene; HATU=2-(3H-[1,2,3]triazolo[4,5-b]pyridin-3-yl)-1,1,3,3-tetramethyl-isouronium hexafluorophosphate(V); HBTU=O-benzotriazole-N,N,N',N'-tetramethyl-uronium-hexafluoro-phosphate; HPLC=LC=high performance liquid chromatography; m-CPBA=meta-chloroperoxybenzoic acid; NMP=N-methylpyrrolidine; PMB=para-methoxy benzyl; TBTU=O-(benzotriazol-1-yl)-N,N,N',N'-tetramethyl-uronium-tetrafluoroborate; TBME=methyl tert-butylether, TFA=trifluoroacetic acid; THF=tetrahydrofuran; tlc=thin layer chromatography; CAN=CAS Registry Number.

The preparation of compounds of formula (I) of the present invention may be carried out in sequential or convergent synthetic routes. Syntheses of the compounds of the invention are shown in the following schemes. The skills required for carrying out the reactions and purifications of the resulting products are known to those skilled in the art. The substituents and indices used in the following description of the processes have the significance given herein before unless indicated to the contrary. In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations*, 2nd Edition, Richard C. Larock. John Wiley & Sons, New York, N.Y. 1999. We find it convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Unless otherwise indicated, $R^1$ to $R^4$ and n have in the following schemes the same meaning as described above.

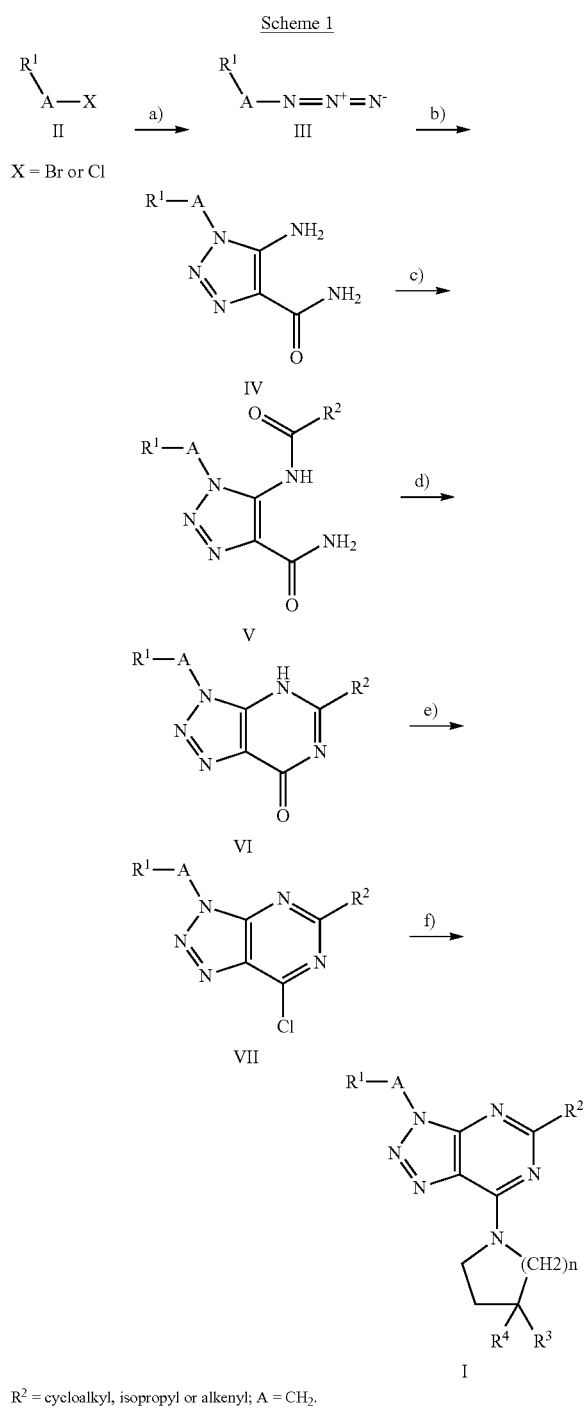

Scheme 1

$R^2$ = cycloalkyl, isopropyl or alkenyl; A = $CH_2$.

a) Halides II are either commercially available or can be synthesized according to methods known in the art. These halides II are conveniently reacted with sodium azide in a suitable solvent such as acetonitrile, ethanol or DMF to afford azide derivatives III. Alternative preferred conditions involve the use of solvents like DMA, NMP or DMSO, even more preferred are NMP and DMSO. In polar aprotic solvents like NMP and DMSO, the alkylations can usually be conducted at lower temperature than for example in acetonitrile, often at room temperature to 40° C. (this is the case for example for BnCl, 1-chloro-2-(chloromethyl)benzene or PMB-Cl; this depends of course on the reactivity of the Halides II) and hence provide a better process safety window (caution organic azides are of course know to be potentially dangerous and process safety has always to be carefully assessed). The addition of water can be beneficial as it increases the solubility of sodium azide and provided more robust kinetic profiles as it helps to dissolves hard clumps of NaN3. It can also lead to a better filterability of the final azide reaction mixture. Filtration of the reaction mixture might be required for example when the following cycloaddition is performed in a continuous mode in small channels reactors. The azide is not isolated and its solution is best introduced in the next step. This also avoids its isolation which can also lead to safety issues.

b) Triazole derivatives IV can be prepared by a [3+2] cycloaddition of azide derivatives III with 2-cyanoacetamide in the presence of an appropriate base such as sodium methoxide or sodium ethoxide in a suitable solvent such as methanol, ethanol or DMF. Alternative preferred conditions involve reacting the azide with 2-cyanoacetamide in solvents like NMP or DMSO, in the presence of sodium hydroxide. The batch process is usually performed at room temperature to 50° C., preferably between room temperature and 40° C. (caution, process safety has always to be carefully assessed). The cycloaddition process is also amendable to continuous mode (for a relevant literature example, see Org. Process Res. Dev., 2009, 13 (6), pp 1401-1406) and in this case the reaction temperature can be increased above 50° C., for example (but not limited to) between 50° C. and 90° C., preferably between 60° C. and 70° C.

c) Triazole IV can conveniently be reacted with an appropriate acid chloride (commercially available or known in the art) in the presence of a base (pyridine, DIPEA, $NEt_3$ and the like) in the presence or absence of a solvent (DCM, DMF and the like) to access triazole derivatives V.

d) Cyclisation of triazole V is can conveniently be done under basic conditions. It proved advantageous to perform this reaction under aqueous conditions in the presence of a base. Suitable bases are $NaHCO_3$ or $KHCO_3$ and the like. This gave access to triazolopyrimidine derivatives VI.

e) Chlorides VII can be obtained by reaction of VI with a chlorination reagent such as $POCl_3$, $SOCl_2$ or $(COCl)_2$ in the presence of an appropriate base such as N,N-diethyl aniline, lutidine, or pyridine. Alternative preferred conditions involve the use of the Vislmeier reagent as chlorinating agent. It can also be generated in situ by reacting oxalyl chloride with DMF. The chlorination can be performed for example in acetonitrile, DCM or AcOEt, preferably in DCM. These conditions allow for mild reaction temperature and for example, avoid the quench of excess $POCl_3$ upon work-up. The crude product can be introduced in the next step.

f) VII are conveniently reacted with various nucleophiles particularly amines in the presence of an appropriate base such as triethylamine, DIPEA or DBU in a suitable solvent such as acetonitrile, methanol, toluene or DMF to yield triazolo-pyrimidine derivatives I.

These derivatives can be the final compounds, however preferably when $R^1$-A is a substituted benzyl group such as p-methoxy benzyl, these groups can be cleaved with TFA, CAN, hydrogenation and the like to access derivatives wherein R¹-A is replaced with H. The benzyl group can be cleaved under standard hydrogenolysis conditions also for example in the presence of acids.

The triazole derivatives wherein R¹-A has been replaced with H is conveniently reacted either with a halide (or sulfonate) in the presence of suitable base such as DIPEA, DBU, K₂CO₃, or Cs₂CO₃ in a solvent such as DMF, dioxane or toluene, or alternatively with an alcohol under Mitsunobu reaction conditions using suitable diazodicarboxylate (DEAD, DIAD and the like) and phosphine such as PBu₃ or PPh₃ in an appropriate solvent such as THF, DCM, toluene to afford final triazolopyrimidine derivatives I.

Scheme 2

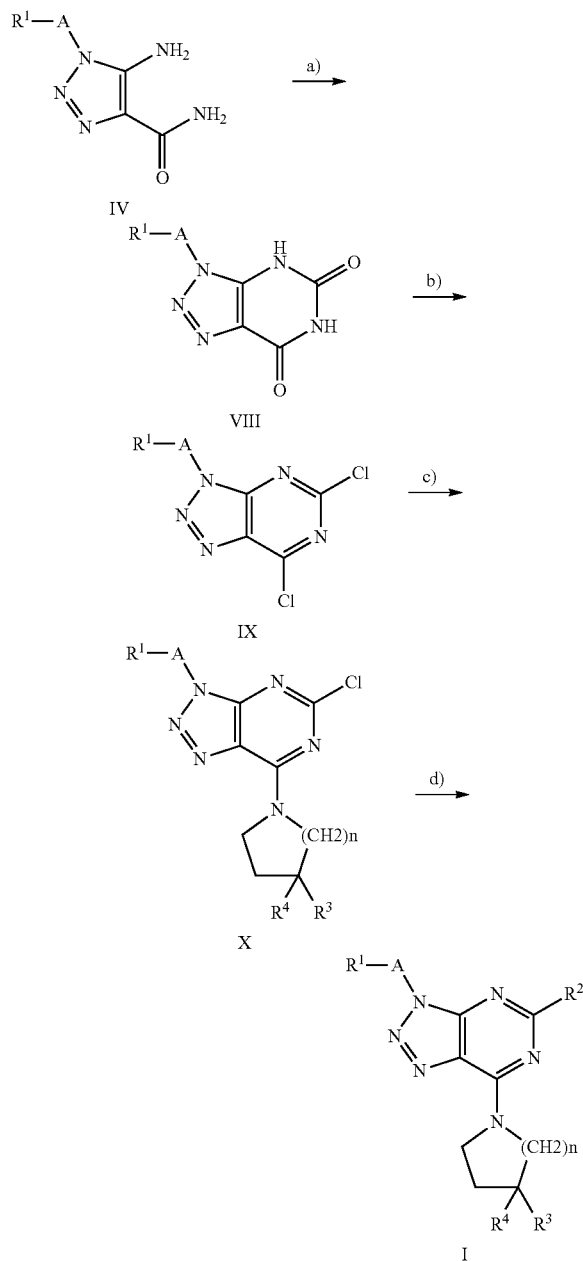

R² is as defined above but not cycloalkyl nor isopropyl, nor alkenyl; A = CH₂.

a) Triazole IV can conveniently be reacted with diethyl carbonate (or any other suitable C1-fragment, commercially available or known in the art) in the presence of a base (NaOEt and the like) in the presence or absence of a solvent (ethanol, dioxane and the like) to access triazolopyrimidine derivative VIII.

b) Chlorides IX can be obtained by reaction of VIII with a chlorination reagent such as POCl₃, SOCl₂ or (COCl)₂ in the presence of an appropriate base such as N,N-diethyl aniline, lutidine, or pyridine. Alternative preferred conditions involve the use of the Vislmeier reagent as chlorinating agent. It can also be generated in situ by reacting oxalyl chloride with DMF. The chlorination can be performed for example in acetonitrile, DCM or AcOEt, preferably in DCM. The crude product can be introduced in the next step.

c) Nucleophilic substitution of chloride IX with an appropriate amine can be performed in the presence of absence of a base (DIPEA, NEt₃ and the like) and a solvent (DCM, dioxane, DMF and the like to access triazolopyrimidine X.

d) Nucleophilic substitution of triazolopyrimidine X with an appropriate amine, sulfide or alcohol can be performed in the presence or absence of a base (DBU, DIPEA, NaH, Cs₂CO₃ and the like) and a solvent (DCM, THF, dioxane, DMF and the like to access triazolopyrimidine I.

These derivatives can be the final compounds, however preferably when R¹-A is a substituted benzyl group such as p-methoxy benzyl, these groups can be cleaved with TFA, CAN, hydrogenation and the like to access derivatives wherein R¹-A has been replaced with H. The benzyl group can be cleaved under standard hydrogenolysis conditions also for example in the presence of acids.

The triazole derivatives wherein R¹-A has been replaced with H is conveniently reacted either with a halide (or sulfonate) in the presence of suitable base such as DIPEA, DBU, K₂CO₃ or Cs₂CO₃ in a solvent such as DMF, dioxane or toluene, or alternatively with an alcohol under Mitsunobu reaction conditions using suitable diazodicarboxylate (DEAD, DIAD and the like) and phosphine such as PBu₃ or PPh₃ in an appropriate solvent such as THF, DCM, toluene to afford final triazolopyrimidine derivatives I.

The compounds of formula I wherein R² is a sulfur containing group as defined above (e.g. a sulfanyl) can be conveniently oxidized with m-CPBA to afford a sulfone of formula I.

The invention also relates to a process for the preparation of a compound of formula (I) comprising one of the following steps:

(a) the reaction of a compound of formula (A1)

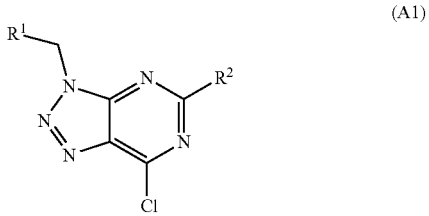

(A1)

in the presence of a compound of formula (A2)

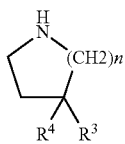

(A2)

wherein $R^2$ is isopropyl, cycloalkyl or alkenyl and $R^1$, $R^3$, $R^4$ and n are as defined above;

(b) the reaction of a compound of formula (B)

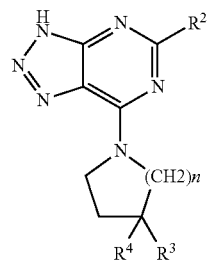

(B)

in the presence of $R^1CH_2X$ wherein X is a halogen, a hydroxyl or a sulfonate group, wherein $R^2$ is isopropyl, cycloalkyl or alkenyl and wherein $R^3$ to $R^4$ and n are as defined above; or (c) the reaction of a compound of formula (C)

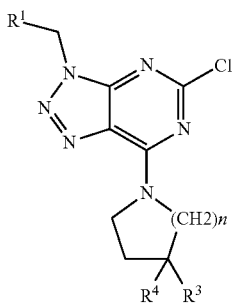

(C)

in the presence of $R^2$—H wherein $R^2$ is piperidinyl, alkylamino, azetidinyl, pyrrolidinyl, cycloalkylamino, alkyloxetanylamino, morpholinyl, (cycloalkyl)(alkyl)amino, haloalkyloxy, alkoxy, cycloalkylalkoxy, cycloalkyloxy, oxetanyloxy, alkyloxetanylalkyloxy, alkynyloxy, alkoxyalkoxy, hydroxyalkyloxy, alkylsulfanyl, haloalkylsulfanyl, alkylsulfonyl, hydroxyalkylsulfanyl, hydroxyalkylsulfonyl or alkoxyalkylsulfonyl and wherein $R^1$, $R^3$, $R^4$ and n are as defined above.

Step (a) is preferably carried out in the presence of an appropriate base such as triethylamine, DIPEA or DBU.

Step (a) is preferably carried out in a suitable solvent such as acetonitrile, methanol, toluene or DMF.

Step (b) is preferably carried out in the presence of a suitable base such as DIPEA, DBU, $K_2CO_3$ or $Cs_2CO_3$.

Step (b) is preferably carried out in a solvent such as DMF, dioxane or toluene.

When X is a hydroxyl group, step (b) can be carried out under Mitsunobu reaction conditions using suitable diazodicarboxylate (e.g. DEAD, DIAD) and phosphine such as $PBu_3$ or $PPh_3$. The reaction can be done in an appropriate solvent such as THF, DCM or toluene.

Step (c) can be carried out in the presence or absence of a base (e.g. DBU, DIPEA, NaH or $Cs_2CO_3$).

Step (c) can be carried out in the presence of a solvent (DCM, THF, dioxane, DMF).

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention also relates in particular to:

The use of a compound of formula (I) for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis;

The use of a compound according of formula (I) for the preparation of a medicament for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis;

A compound of formula (I) for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis; and A method for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis, which method comprises administering an effective amount of a compound of formula (I) to a patient in need thereof.

The invention particularly relates to a compound of formula (I) for the treatment or prophylaxis of ischemia, reperfusion injury, liver fibrosis or kidney fibrosis, in particular ischemia or reperfusion injury.

The invention is further directed to a compound of formula (I), when manufactured according to a process according to the invention.

The invention will now be illustrated by the following examples which have no limiting character.

EXAMPLES

Example 1

3-[(2-Chlorophenyl)methyl]-5-cyclobutyl-7-(3,3-difluoropyrrolidin-1-yl)triazolo[4,5-d]pyrimidine

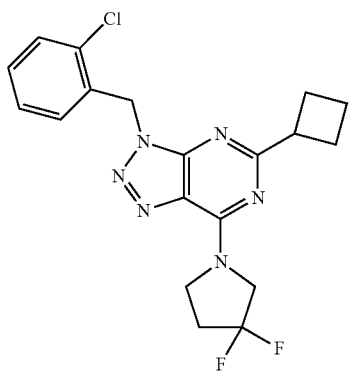 [SMILES: FC1(F)CCN(c2nc(C3CCC3)nc3c2nnn3Cc2ccccc2Cl)C1]

a) 5-Amino-1-(2-chlorobenzyl)-1H-1,2,3-triazole-4-carboxamide

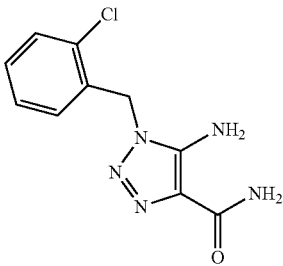 [SMILES: NC(=O)c1nnn(Cc2ccccc2Cl)c1N]

A mixture of 1-(bromomethyl)-2-chlorobenzene (5 g, 24.3 mmol) and sodium azide (2.37 g, 36.5 mmol) in acetonitrile (48.7 mL) was refluxed for 3 h under $N_2$ atmosphere. Then, the mixture was filtered and concentrated in vacuo. The residue was diluted in DCM, washed with $H_2O$ and brine, dried over $Na_2SO_4$ and concentrated in vacuo to afford crude 1-(azidomethyl)-2-chlorobenzene. The residue was used for the next reaction without further purification. A mixture of the above crude residue, 2-cyanoacetamide (1.82 g, 21.7 mmol) and sodium ethanolate (1.47 g, 21.7 mmol) in ethanol (43.3 mL) was refluxed for 3 h under $N_2$ atmosphere. The mixture was concentrated in vacuo, diluted with 4M AcOH aq. and filtered. The residue was washed with $H_2O$ and dried in vacuo to the title compound as pale-orange solid (5.10 g, 94% for 2 steps). MS(m/e): 252.1 (MH$^+$).

b) 1-[(2-Chlorophenyl)methyl]-5-(cyclobutanecarbonylamino)triazole-4-carboxamide

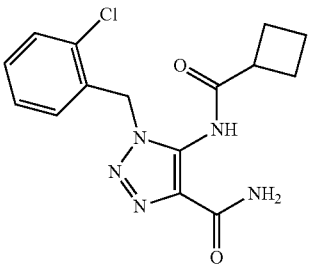 [SMILES: NC(=O)c1nnn(Cc2ccccc2Cl)c1NC(=O)C1CCC1]

A mixture of 5-Amino-1-(2-chlorobenzyl)-1H-1,2,3-triazole-4-carboxamide (1.1 g, crude) and cyclobutanecarbonyl chloride (777 mg, 748 µl, 6.56 mmol) in pyridine (30 mL) was heated to 80° C. for 5 h. After cooling to room temperature HCl (50 mL, 1M) was carefully added and the mixture was extracted with ethyl acetate (3×100 mL). The combined organic layers were dried with MgSO₄, filtered and evaporated to dryness. The residue was used in the consecutive step without further purification. MS(m/e): 333.7 (MH⁺).

c) 3-[(2-Chlorophenyl)methyl]-5-cyclobutyl-6H-triazolo[4,5-d]pyrimidin-7-one

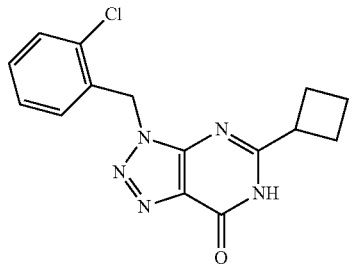 [SMILES: O=c1[nH]c(C2CCC2)nc2c1nnn2Cc1ccccc1Cl]

A mixture of 1-[(2-chlorophenyl)methyl]-5-(cyclobutanecarbonylamino)triazole-4-carboxamide (1.37 g, crude) and KHCO₃ (2.96 g, 29.6 mmol) in water (60 mL) was heated to reflux overnight. After cooling to room temperature NaHCO₃ aq. (50 mL, 1N) was added and the mixture was extracted with TBME (3×125 mL). The combined organic layers were dried with MgSO₄ and evaporated to dryness. The residue was subjected to purification by preparative HPLC on reversed phase eluting with a gradient formed from acetonitrile, water and NEt₃. After evaporation of the product containing fractions 182 mg (14%) of the title compound was isolated as white solid. MS(m/e): 357.2 (MH⁺).

d) 3-[(2-Chlorophenyl)methyl]-5-cyclobutyl-7-(3,3-difluoropyrrolidin-1-yl)triazolo[4,5-d]pyrimidine A mixture of 3-[(2-chlorophenyl)methyl]-5-cyclobutyl-6H-triazolo[4,5-d]pyrimidin-7-one (185 mg, 0.586 mmol), POCl₃ (2.7 g, 17.6 mmol) and N,N-diethylaniline (0.21 g, 1.41 mmol) at 0° C. was heated to 120° C. for 4 h. The mixture was evaporated, the residue poured into ice/water (100 mL) and extracted with DCM (2×200 mL). The combined organic layers were dried with MgSO₄ and evaporated. The residue was taken up in acetonitrile (10 mL) and 3,3-difluoropyrrolidine hydrochloride (295 mg, 2.05 mmol) was added and DIPEA (379 mg, 2.93 mmol) and the mixture was stirred for 2 days at room temperature. After evaporation of the mixture the residue was subjected to purification by preparative HPLC on reversed phase eluting with a gradient formed from acetonitrile, water and NEt₃. After evaporation of the product containing fractions 50 mg (21%) of the title compound was isolated as light yellow solid. MS(m/e): 405.2 (MH⁺).

Example 2

5-Cyclopropyl-7-(3,3-difluoropyrrolidin-1-yl)-3-[(4-methoxyphenyl)methyl]triazolo[4,5-d]pyrimidine

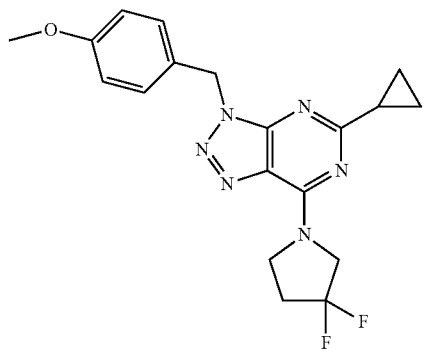 [SMILES: COc1ccc(Cn2nnc3c(N4CCC(F)(F)C4)nc(C4CC4)nc32)cc1]

a) 5-Amino-1-(4-methoxybenzyl)-1H-1,2,3-triazole-4-carboxamide

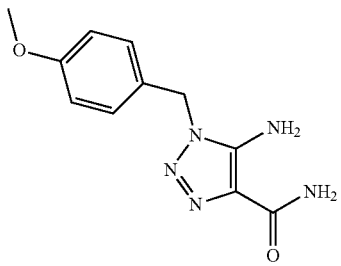 [SMILES: COc1ccc(Cn2nnc(C(N)=O)c2N)cc1]

A mixture of 1-(chloromethyl)-4-methoxybenzene (20 g, 128 mmol) and sodium azide (12.5 g, 192 mmol) in acetonitrile (250 mL) was refluxed for 5 h under N₂ atmosphere. The mixture was filtered and concentrated in vacuo. The residue was diluted with DCM, washed with H₂O and brine, dried over Na₂SO₄ and concentrated in vacuo to afford crude 1-(azidomethyl)-4-methoxybenzene. The residue was used for the next reaction without further purification.

A mixture of the above crude residue, 2-cyanoacetamide (10.8 g, 128 mmol) and sodium ethanolate (8.71 g, 128 mmol) in ethanol (250 mL) was refluxed for 21 h under N₂ atmosphere. The mixture was concentrated in vacuo, diluted with 4M AcOH aq. and filtered. The residue was washed with H₂O and dried in vacuo to afford 5-amino-1-(4-methoxybenzyl)-1H-1,2,3-triazole-4-carboxamide as pale-orange solid (26.5 g, 84% for 2 steps). MS(m/e): 248.1 (MH⁺).

b) 5-(Cyclopropanecarbonylamino)-1-[(4-methoxyphenyl)methyl]triazole-4-carboxamide

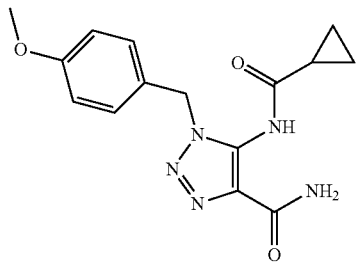 [SMILES: COc1ccc(Cn2nnc(C(N)=O)c2NC(=O)C2CC2)cc1]

A mixture of 5-amino-1-(4-methoxybenzyl)-1H-1,2,3-triazole-4-carboxamide (1 g, crude) and cyclopropanecarbonyl chloride (1.27 g, 12.1 mmol) in pyridine (8 mL) was heated to 80° C. for 3 h. The mixture was evaporated and methanol (8 mL) and NaOH aq. (1.5 mL) was added and heated to 80° C. for 1 h. The mixture was cooled and poured into HCl aq. (50 mL, 1M) and extracted with ethyl acetate (3×100 mL). The combined organic layers were dried with MgSO₄ an evaporated to yield the crude title compound which was used in the consecutive step without further purification. MS(m/e): 316.5 (MH⁺).

c) 5-Cyclopropyl-3-[(4-methoxyphenyl)methyl]-6H-triazolo[4,5-d]pyrimidin-7-one

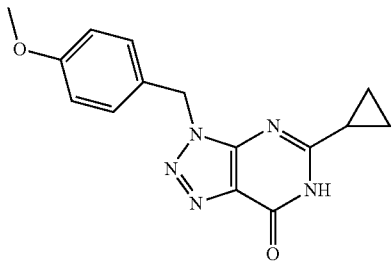 [SMILES: COc1ccc(Cn2nnc3c(=O)[nH]c(C4CC4)nc32)cc1]

A mixture of 5-(cyclopropanecarbonylamino)-1-[(4-methoxyphenyl)methyl]triazole-4-carboxamide (1 g, crude) and KHCO₃ aq. (2.36 g, 23.6 mmol) in 46 mL water was heated to reflux overnight. After cooling to room temperature the mixture was filtered and the light yellow solid dried. The filtrate was extracted with DCM (3×125 mL) and the combined organic layers were dried with MgSO₄ and evaporated. This residue was combined with the light yellow solid to yield the title compound as light yellow solid. MS(m/e): 298.5 (MH⁺).

d) 5-Cyclopropyl-7-(3,3-difluoropyrrolidin-1-yl)-3-[(4-methoxyphenyl)methyl]triazolo [4,5-d]pyrimidine A mixture of 5-cyclopropyl-3-[(4-methoxyphenyl)methyl]-6H-triazolo[4,5-d]pyrimidin-7-one (0.32 g, crude), POCl₃ (4.95 g, 32.3 mmol) and N,N-diethylaniline (0.385 g, 2.58 mmol) was heated to 120° C. for 4 h. The mixture was evaporated, the residue poured into ice/water (100 mL) and extracted with DCM (2×200 mL). The combined organic layers were dried with MgSO₄ and evaporated. The residue was taken up in acetonitrile (15 mL) and 3,3-difluoropyrrolidine hydrochloride (847 mg, 5.9 mmol) and DIPEA (693 mg, 5.36 mmol) was added and the mixture was stirred for 2 days at room temperature. After evaporation of the mixture the residue was subjected to purification by preparative HPLC on reversed phase eluting with a gradient formed from acetonitrile, water and NEt₃. After evaporation of the product containing fractions 160 mg (39%) of the title compound was isolated as light yellow solid. MS(m/e): 387.2 (MH⁺).

Example 3

3-[(2-Chlorophenyl)methyl]-7-(3,3-difluoropyrrolidin-1-yl)-5-isopropyl-triazolo[4,5-d]pyrimidine

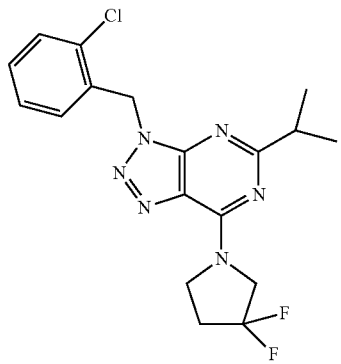 [SMILES: CC(C)c1nc(N2CCC(F)(F)C2)c2nnn(Cc3ccccc3Cl)c2n1]

a) 1-(2-Chloro-benzyl)-5-isobutyrylamino-1H-[1,2,3]triazole-4-carboxylic acid amide

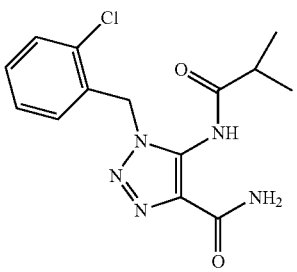 [SMILES: CC(C)C(=O)Nc1c(C(N)=O)nnn1Cc1ccccc1Cl]

A mixture of 5-amino-1-(2-chlorobenzyl)-1H-1,2,3-triazole-4-carboxamide (1 g, crude) and isobutyryl chloride (1.27 g, 12.1 mmol) in pyridine (8 mL) was heated to 80° C. for 3 h. The mixture was evaporated and methanol (8 mL) and NaOH aq. (1.5 mL) was added and heated to 80° C. for 1 h. The mixture was cooled and poured into HCl aq. (50 mL, 1M) and extracted with ethyl acetate (3×100 mL). The combined organic layers were dried with MgSO₄ an evaporated to yield the crude title compound as light yellow solid which was used in the consecutive step without further purification. MS(m/e): 322.5 (MH⁺).

b) 3-[(2-Chlorophenyl)methyl]-5-isopropyl-6H-triazolo[4,5-d]pyrimidin-7-one

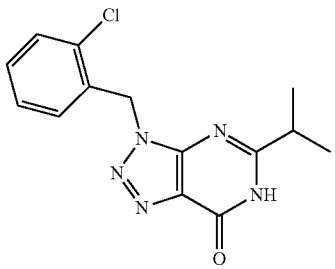 [SMILES: CC(C)c1nc2c(nnn2Cc2ccccc2Cl)c(=O)[nH]1]

A mixture of 1-(2-chloro-(benzyl)-5-isobutyrylamino-1H-[1,2,3]triazole-4-carboxylic acid amide (1.37 g, crude) and KHCO$_3$ (4.37 g, 43.6 mmol) in water (50 mL) was heated to 120° C. overnight. After cooling to room temperature with mixture was filtered and the residue dried to yield the crude title compound as white powder. MS(m/e): 304.5 (MH$^+$).

c) 3-[(2-Chlorophenyl)methyl]-7-(3,3-difluoropyrrolidin-1-yl)-5-isopropyl-triazolo[4,5-d]pyrimidine

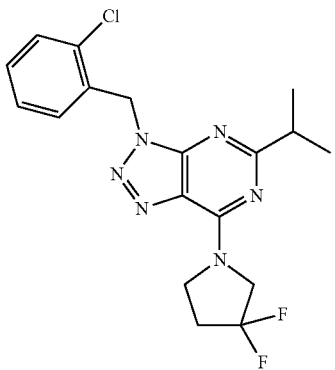 [SMILES: CC(C)c1nc(N2CCC(F)(F)C2)c2nnn(Cc3ccccc3Cl)c2n1]

A mixture of 3-[(2-chlorophenyl)methyl]-5-isopropyl-6H-triazolo[4,5-d]pyrimidin-7-one (0.74 g, crude), POCl$_3$ (8.97 g, 58.5 mmol) and N,N-diethylaniline (0.698 g, 4.68 mmol) was heated to 120° C. for 2 h. The mixture was evaporated, the residue poured into ice/water (100 mL) and extracted with DCM (2×200 mL). The combined organic layers were dried with MgSO$_4$ and evaporated. The residue was taken up in acetonitrile (10 mL) and 3,3-difluoropyrrolidine hydrochloride (1.53 g, 10.6 mmol) and DIPEA (1.25 g, 9.68 mmol) was added and the mixture was stirred for 2 days at room temperature. After evaporation of the mixture the residue was subjected to purification by preparative HPLC on reversed phase eluting with a gradient formed from acetonitrile, water and NEt$_3$. After evaporation of the product containing fractions 154 mg (20%) of the title compound was isolated as yellow oil. MS(m/e): 393.2 (MH$^+$).

Example 4

3-[(2-Chlorophenyl)methyl]-5-cyclopropyl-7-(3,3-difluoropyrrolidin-1-yl)triazolo[4,5-d]pyrimidine

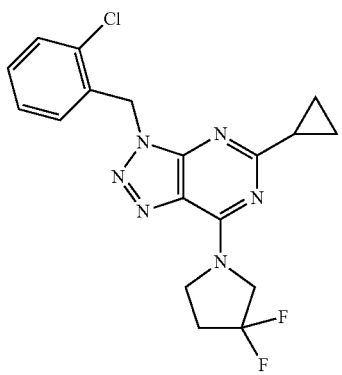 [SMILES: FC1(F)CCN(c2nc(C3CC3)nc3c2nnn3Cc2ccccc2Cl)C1]

a) 5-Cyclopropyl-7-(3,3-difluoropyrrolidin-1-yl)-3H-triazolo[4,5-d]pyrimidine

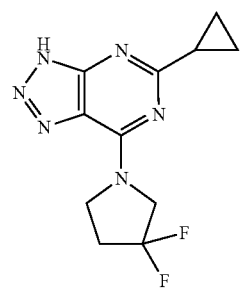 [SMILES: FC1(F)CCN(c2nc(C3CC3)nc3[nH]nnc23)C1]

A mixture of 5-cyclopropyl-7-(3,3-difluoropyrrolidin-1-yl)-3-(4-methoxybenzyl)-3H-[1,2,3]triazolo[4,5-d]pyrimidine (example 2) (0.16 g, 0.41 mmol) and TFA (2 mL) was heated to 80° C. for 2 h. The mixture was evaporated and the residue was poured into NaHCO$_3$ aq. (20 mL, 1M) and extracted with ethyl acetate (3×20 mL). The combined organic layers were dried with MgSO$_4$, filtered and evaporated to yield the crude title compound as orange solid which was used in the consecutive step without further purification. MS(m/e): 267.1 (MH$^+$).

b) 3-[(2-Chlorophenyl)methyl]-5-cyclopropyl-7-(3,3-difluoropyrrolidin-1-yl)triazolo[4,5-d]pyrimidine A mixture of 5-cyclopropyl-7-(3,3-difluoropyrrolidin-1-yl)-3H-triazolo[4,5-d]pyrimidine (55 mg, crude), 1-(bromomethyl)-2-chlorobenzene (85 mg, 0.413 mmol) and DBU (94 mg, 0.62 mmol) in DMF (3 mL) was heated to 80° C. for 12 h. After cooling to room temperature the mixture was subjected to purification by preparative HPLC on reversed phase eluting with a gradient formed from acetonitrile, water and NEt$_3$. After evaporation of the product containing fractions 8.1 mg (10%, 2 steps) of the title compound was isolated as dark green solid. MS(m/e): 391.2 (MH$^+$).

Example 5

3-[[5-Cyclopropyl-7-(3,3-difluoropyrrolidin-1-yl)triazolo[4,5-d]pyrimidin-3-yl]methyl]-4-methyl-1,2,5-oxadiazole

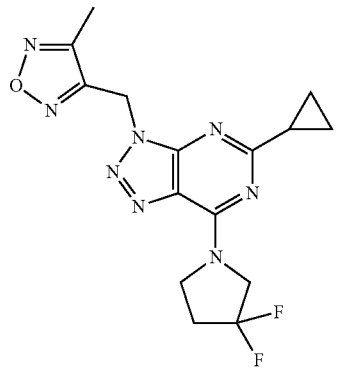 [SMILES: Cc1nonc1Cn1nnc2c(N3CCC(F)(F)C3)nc(C3CC3)nc21]

In analogy to the procedure described for the synthesis of 3-[(2-chlorophenyl)methyl]-5-cyclopropyl-7-(3,3-difluoropyrrolidin-1-yl)triazolo[4,5-d]pyrimidine (example 4) the title compound was prepared from 5-cyclopropyl-7-(3,3-difluoropyrrolidin-1-yl)-3H-[1,2,3]triazolo[4,5-d]pyrimidine and 3-(bromomethyl)-4-methyl-1,2,5-oxadiazole as light brown solid. MS(m/e): 363.2 (MH+).

Example 6

(3S)-1-[3-[(2-Chlorophenyl)methyl]-5-prop-1-en-2-yltriazolo[4,5-d]pyrimidin-7-yl]pyrrolidin-3-ol

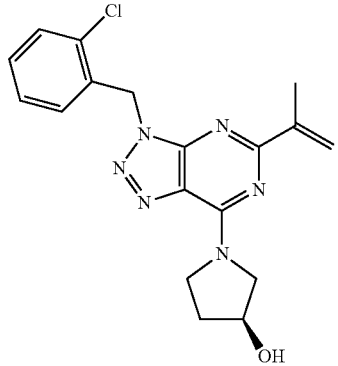 [SMILES: C=C(C)c1nc(N2CC[C@H](O)C2)c2nnn(Cc3ccccc3Cl)c2n1]

a) 3-[(2-Chlorophenyl)methyl]-5-(1-hydroxy-1-methyl-ethyl)-6H-triazolo[4,5-d]pyrimidin-7-one

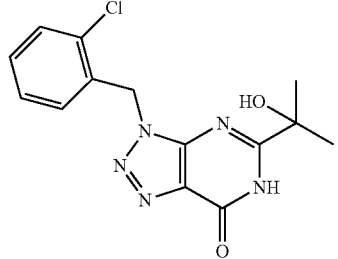 [SMILES: CC(C)(O)c1nc2c(nnn2Cc2ccccc2Cl)c(=O)[nH]1]

A mixture of 5-Amino-1-(2-chlorobenzyl)-1H-1,2,3-triazole-4-carboxamide (3 g, 11.9 mmol) and 1-chloro-2-methyl-1-oxopropan-2-yl acetate (5.89 g, 35.8 mmol) in pyridine (20 mL) was heated to 80° C. and stirred for 3 h. After cooling to room temperature the mixture was evaporated and poured into HCl aq. (50 mL, 1M) and extracted with ethyl acetate (3×100 mL). The combined organic layers were dried with MgSO₄, filtered and evaporated. KHCO₃ (9.79 g, 97.8 mmol) and water (150 mL) was added and the mixture was heated to 120° C. for 24 h. After cooling to room temperature the mixture was extracted with DCM (2×200 mL). The combined organic layers were dried with MgSO₄, filtered and evaporated to yield 1.4 g (4.47 mmol, 37%) of the title compound as yellow oil. MS(m/e): 361.2 (MH+).

b) (3S)-1-[3-[(2-Chlorophenyl)methyl]-5-prop-1-en-2-yltriazolo[4,5-d]pyrimidin-7-yl]pyrrolidin-3-ol A mixture of 3-[(2-chlorophenyl)methyl]-5-(1-hydroxy-1-methyl-ethyl)-6H-triazolo[4,5-d]pyrimidin-7-one (1.18 g, 3.7 mmol) and NaH (193 mg, suspension in oil, 4.82 mmol) and (bromomethyl)benzene (951 mg, 5.56 mmol) in DMF (20 mL) at 0° C. was stirred to room temperature and continued for 4 h. The mixture was poured into HCl aq. (20 mL, 1M) and extracted with DCM (3×100 mL). The combined organic layers were dried with MgSO₄, filtered and evaporated. POCl₃ (28.2 g, 184 mmol) and N,N-diethylamine (1.32 g, 8.83 mmol) was added at 0° C. and the mixture was heated to 120° C. for 4 h. The mixture was evaporated and poured into ice/water (100 mL) and extracted with DCM (2×200 mL). The combined organic layers were dried with MgSO₄, filtered and evaporated to yield 2.5 g of the crude chlorinated intermediate. 205 mg of the crude intermediate were dissolved in acetonitrile (5 mL) and DIPEA (148 mg, 1.15 mmol) and (S)-pyrrolidin-3-ol (37.5 mg, 0.43 mmol) were added and the mixture was stirred at room temperature for 6 h. The mixture was subjected to purification by preparative HPLC on reversed phase eluting with a gradient formed from acetonitrile, water and NEt₃. After evaporation of the product containing fractions 20 mg (0.054 mmol) of the title compound was isolated as light green solid. MS(m/e): 371.2 (MH+).

Example 7

3-[(2-Chlorophenyl)methyl]-5,7-di(piperidin-1-yl)triazolo[4,5-d]pyrimidine

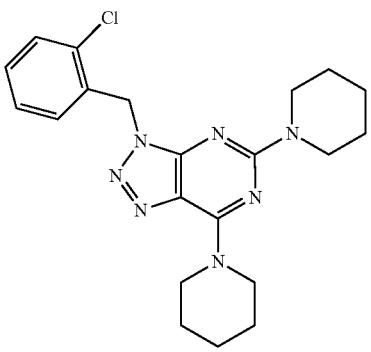 [SMILES: Clc1ccccc1Cn1nnc2c(N3CCCCC3)nc(N3CCCCC3)nc21]

a) 3-[(2-Chlorophenyl)methyl]-4H-triazolo[4,5-d]pyrimidine-5,7-dione

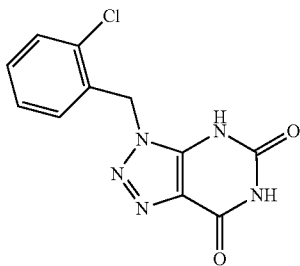 [SMILES: O=c1[nH]c(=O)c2nnn(Cc3ccccc3Cl)c2[nH]1]

A mixture of 5-amino-1-(2-chlorobenzyl)-1H-1,2,3-triazole-4-carboxamide (8 g, 25.4 mmol), sodium ethoxide (4.5 g, 66.1 mmol) and diethyl carbonate (4.51 g, 38.1 mmol) in ethanol (60 mL) was heated to reflux overnight. After cooling to room temperature the mixture was filtered and the precipitate was filtered, washed with ethanol and dried to yield 10 g (25.2 mmol, 99%) of the title compound as white solid. MS(m/e): 278.0 (MH$^+$).

b) 3-[(2-chlorophenyl)methyl]-5,7-di(piperidin-1-yl)triazolo[4,5-d]pyrimidine A mixture of 3-[(2-chlorophenyl)methyl]-4H-triazolo[4,5-d]pyrimidine-5,7-dione (146 mg, 0.368 mmol), POCl$_3$ (1.98 g, 13 mmol) and N,N-diethylaniline (110 mg, 0.736 mmol) was heated to 120° C. for 3 h. After cooling to room temperature the mixture was poured into ice/water (25 mL) and extracted with ethyl acetate (2×25 mL). The combined organic layers were evaporated to yield crude 5,7-dichloro-3-[(2-chlorophenyl)methyl]triazolo[4,5-d]pyrimidine which was used in the consecutive step without further purification.

A mixture of crude 5,7-dichloro-3-[(2-chlorophenyl)methyl]triazolo[4,5-d]pyrimidine (86 mg) and piperidine (186 mg, 2.19 mmol) in chloroform (1 mL) was stirred at room temperature for 1 h. The mixture was subjected to purification by preparative HPLC on reversed phase eluting with a gradient formed from acetonitrile, water and NEt$_3$. After evaporation of the product containing fractions 27 mg (0.065 mmol) of the title compound was isolated as white solid. MS(m/e): 412.2 (MH$^+$).

Example 8

3-[(2-Chlorophenyl)methyl]-7-(3,3-difluoropyrrolidin-1-yl)-N-ethyltriazolo[4,5-d]pyrimidin-5-amine

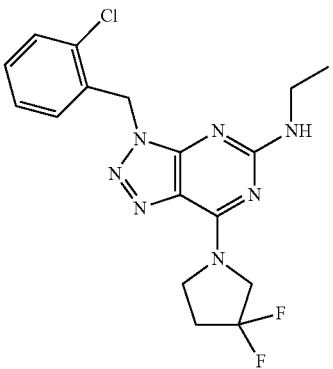 [SMILES: CCNc1nc(N2CCC(F)(F)C2)c2nnn(Cc3ccccc3Cl)c2n1]

a) 5-Chloro-3-[(2-chlorophenyl)methyl]-7-(3,3-difluoropyrrolidin-1-yl)triazolo[4,5-d]pyrimidine

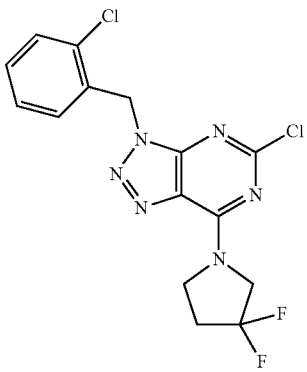 [SMILES: FC1(F)CCN(c2nc(Cl)nc3c2nnn3Cc2ccccc2Cl)C1]

A mixture of 5,7-dichloro-3-[(2-chlorophenyl)methyl]triazolo[4,5-d]pyrimidine (1.7 g, 5.4 mmol), DIPEA (3.49 g, 27 mmol) and 3,3-difluoropyrrolidine hydrochloride (1.09 g, 7.57 mmol) in DCM (0.4 mL) was stirred at 0° C. for 3 h. Isolute was added and the absorbed mixture was subjected to purification by flash column chromatography on silica eluting with a gradient formed from ethyl acetate and heptane to yield after evaporation of the product containing fractions 421 mg (1.09 mmol, 20%) of the title compound as yellow oil. MS(m/e): 385.1 (MH$^+$).

b) 3-[(2-Chlorophenyl)methyl]-7-(3,3-difluoropyrrolidin-1-yl)-N-ethyltriazolo[4,5-d]pyrimidin-5-amine A mixture of 5-chloro-3-[(2-chlorophenyl)methyl]-7-(3,3-difluoropyrrolidin-1-yl)triazolo[4,5-d]pyrimidine (27 mg, 0.07 mmol), DIPEA (90 mg, 0.7 mmol) and ethylamine (16 mg, 0.35 mmol) in DMF (1 mL) was stirred at 110° C. overnight and evaporated to dryness. The residue was subjected to purification by preparative HPLC on reversed phase eluting with a gradient formed from acetonitrile, water and formic acid. After evaporation of the product containing fractions 13.8 mg (50%) of the title compound was isolated. MS(m/e): 394.2 (MH$^+$).

Example 9

5-(Azetidin-1-yl)-3-[(2-chlorophenyl)methyl]-7-(3,3-difluoropyrrolidin-1-yl)triazolo[4,5-d]pyrimidine

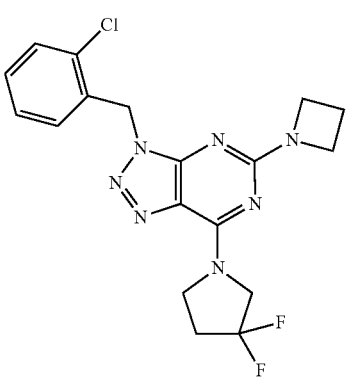 [SMILES: FC1(F)CCN(c2nc(N3CCC3)nc3c2nnn3Cc2ccccc2Cl)C1]

In analogy to the procedure described for the synthesis of 3-[(2-chlorophenyl)methyl]-7-(3,3-difluoropyrrolidin-1-yl)-N-ethyltriazolo[4,5-d]pyrimidin-5-amine (example 8) the title compound was prepared from 5-chloro-3-[(2-chlorophenyl)methyl]-7-(3,3-difluoropyrrolidin-1-yl)triazolo[4,5-d]pyrimidine and azetidine. MS(m/e): 406.2 (MH+).

Example 10

3-[(2-Chlorophenyl)methyl]-7-(3,3-difluoropyrrolidin-1-yl)-5-pyrrolidin-1-yltriazolo[4,5-d]pyrimidine

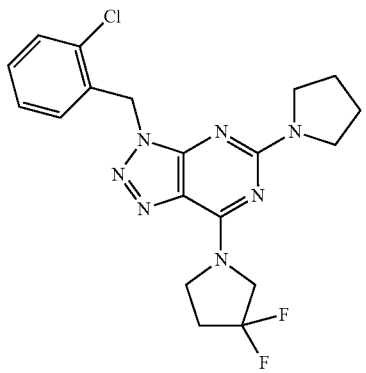 [SMILES: FC1(F)CCN(c2nc(N3CCCC3)nc3c2nnn3Cc2ccccc2Cl)C1]

In analogy to the procedure described for the synthesis of 3-[(2-chlorophenyl)methyl]-7-(3,3-difluoropyrrolidin-1-yl)-N-ethyltriazolo[4,5-d]pyrimidin-5-amine (example 8) the title compound was prepared from 5-chloro-3-[(2-chlorophenyl)methyl]-7-(3,3-difluoropyrrolidin-1-yl)triazolo[4,5-d]pyrimidine and pyrrolidine. MS(m/e): 420.3 (MH+).

Example 11

3-[(2-Chlorophenyl)methyl]-N-cyclobutyl-7-(3,3-difluoropyrrolidin-1-yl)triazolo[4,5-d]pyrimidin-5-amine

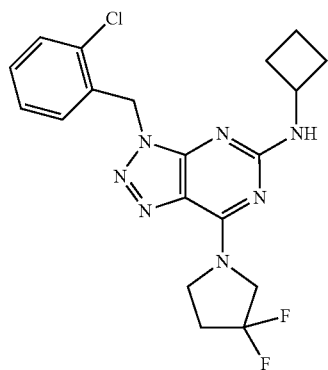 [SMILES: FC1(F)CCN(c2nc(NC3CCC3)nc3c2nnn3Cc2ccccc2Cl)C1]

In analogy to the procedure described for the synthesis of 3-[(2-chlorophenyl)methyl]-7-(3,3-difluoropyrrolidin-1-yl)-N-ethyltriazolo[4,5-d]pyrimidin-5-amine (example 8) the title compound was prepared from 5-chloro-3-[(2-chlorophenyl)methyl]-7-(3,3-difluoropyrrolidin-1-yl)triazolo[4,5-d]pyrimidine and cyclobutylamine. MS(m/e): 420.3 (MH+).

Example 12

N-tert-Butyl-3-[(2-chlorophenyl)methyl]-7-(3,3-difluoropyrrolidin-1-yl)triazolo[4,5-d]pyrimidin-5-amine

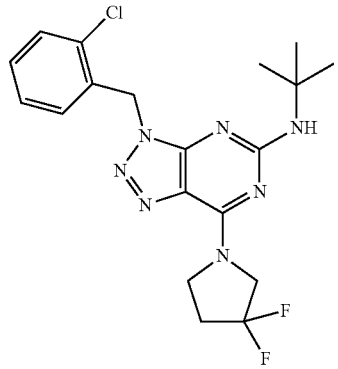 [SMILES: CC(C)(C)Nc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-N-ethyltriazolo[4,5-d]pyrimidin-5-amine (example 8) the title compound was prepared from 5-chloro-3-[(2-chlorophenyl)methyl]-7-(3,3-difluoropyrrolidin-1-yl)triazolo[4,5-d]pyrimidine and 2-methylpropan-2-amine. MS(m/e): 422.3 (MH+).

Example 13

3-[(2-Chlorophenyl)methyl]-7-(3,3-difluoropyrrolidin-1-yl)-N-(3-methyloxetan-3-yl)triazolo[4,5-d]pyrimidin-5-amine

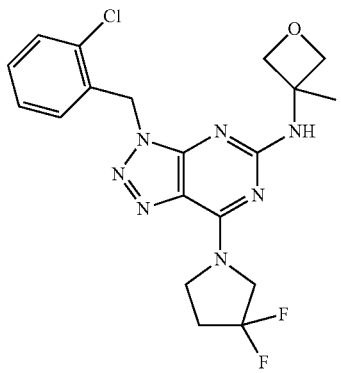 [SMILES: CC1(Nc2nc(N3CCC(F)(F)C3)c3nnn(Cc4ccccc4Cl)c3n2)COC1]

In analogy to the procedure described for the synthesis of 3-[(2-chlorophenyl)methyl]-7-(3,3-difluoropyrrolidin-1-yl)-N-ethyltriazolo[4,5-d]pyrimidin-5-amine (example 8) the title compound was prepared from 5-chloro-3-[(2-chlorophenyl)methyl]-7-(3,3-difluoropyrrolidin-1-yl)triazolo[4,5-d]pyrimidine and 3-methyloxetan-3-amine. MS(m/e): 436.3 (MH+).

Example 14

4-[3-[(2-Chlorophenyl)methyl]-7-(3,3-difluoropyrrolidin-1-yl)triazolo[4,5-d]pyrimidin-5-yl]morpholine

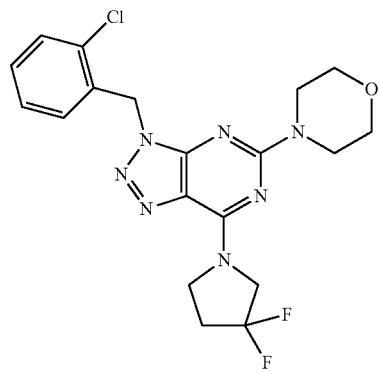 [SMILES: FC1(F)CCN(c2nc(N3CCOCC3)nc3c2nnn3Cc2ccccc2Cl)C1]

In analogy to the procedure described for the synthesis of 3-[(2-chlorophenyl)methyl]-7-(3,3-difluoropyrrolidin-1-yl)-N-ethyltriazolo[4,5-d]pyrimidin-5-amine (example 8) the title compound was prepared from 5-chloro-3-[(2-chlorophenyl)methyl]-7-(3,3-difluoropyrrolidin-1-yl)triazolo[4,5-d]pyrimidine and morpholine. MS(m/e): 436.3 (MH$^+$).

Example 15

N-tert-Butyl-3-[(2-chlorophenyl)methyl]-7-(3,3-difluoropyrrolidin-1-yl)-N-methyltriazolo[4,5-d]pyrimidin-5-amine

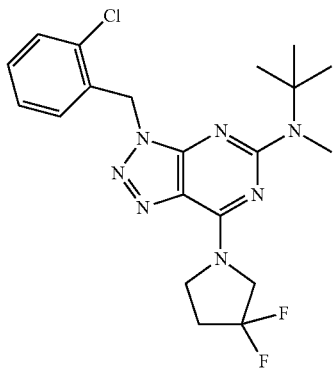 [SMILES: CN(c1nc(N2CCC(F)(F)C2)c2nnn(Cc3ccccc3Cl)c2n1)C(C)(C)C]

In analogy to the procedure described for the synthesis of 3-[(2-chlorophenyl)methyl]-7-(3,3-difluoropyrrolidin-1-yl)-N-ethyltriazolo[4,5-d]pyrimidin-5-amine (example 8) the title compound was prepared from 5-chloro-3-[(2-chlorophenyl)methyl]-7-(3,3-difluoropyrrolidin-1-yl)triazolo[4,5-d]pyrimidine and tert-butyl-methyl-amine. MS(m/e): 436.3 (MH$^+$).

Example 16

3-[(2-Chlorophenyl)methyl]-7-(3,3-difluoropyrrolidin-1-yl)-N-(2,2-dimethylpropyl) triazolo[4,5-d]pyrimidin-5-amine

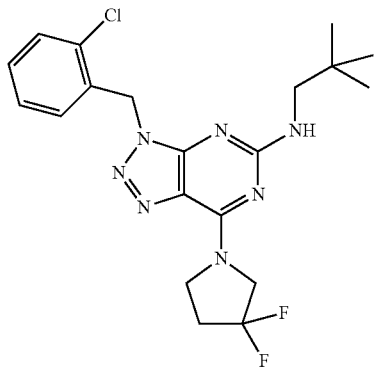 [SMILES: CC(C)(C)CNc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-N-ethyltriazolo[4,5-d]pyrimidin-5-amine (example 8) the title compound was prepared from 5-chloro-3-[(2-chlorophenyl)methyl]-7-(3,3-difluoropyrrolidin-1-yl)triazolo[4,5-d]pyrimidine and 2,2-dimethylpropan-1-amine. MS(m/e): 436.3 (MH$^+$).

Example 17

3-[(2-Chlorophenyl)methyl]-7-(3,3-difluoropyrrolidin-1-yl)-N-(oxetan-3-yl)triazolo[4,5-d]pyrimidin-5-amine

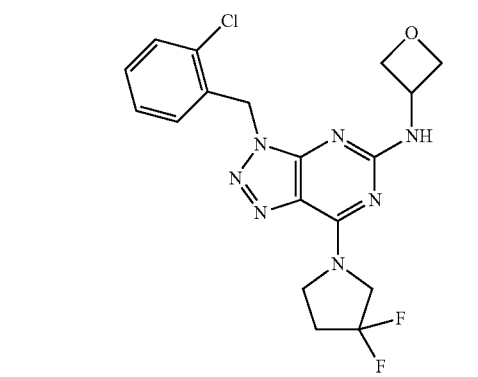 [SMILES: FC1(F)CCN(c2nc(NC3COC3)nc3c2nnn3Cc2ccccc2Cl)C1]

In analogy to the procedure described for the synthesis of 3-[(2-chlorophenyl)methyl]-7-(3,3-difluoropyrrolidin-1-yl)-N-ethyltriazolo[4,5-d]pyrimidin-5-amine (example 8) the title compound was prepared from 5-chloro-3-[(2-chlorophenyl)methyl]-7-(3,3-difluoropyrrolidin-1-yl)triazolo[4,5-d]pyrimidine and oxetan-3-amine hydrochloride. MS(m/e): 422.2 (MH$^+$).

Example 18

3-[(2-Chlorophenyl)methyl]-N-cyclobutyl-7-(3,3-difluoropyrrolidin-1-yl)-N-methyltriazolo[4,5-d]pyrimidin-5-amine

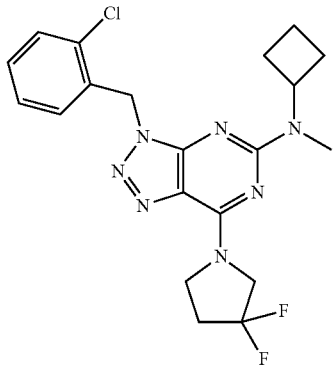 [SMILES: CN(c1nc(N2CCC(F)(F)C2)c2nnn(Cc3ccccc3Cl)c2n1)C1CCC1]

In analogy to the procedure described for the synthesis of 3-[(2-chlorophenyl)methyl]-7-(3,3-difluoropyrrolidin-1-yl)-N-ethyltriazolo[4,5-d]pyrimidin-5-amine (example 8) the title compound was prepared from 5-chloro-3-[(2-chlorophenyl)methyl]-7-(3,3-difluoropyrrolidin-1-yl)triazolo[4,5-d]pyrimidine and N-methylcyclobutanamine hydrochloride. MS(m/e): 434.3 (MH$^+$).

Example 19

(3S)-1-[5-(tert-Butylamino)-3-[(4-methoxyphenyl)methyl]triazolo[4,5-d]pyrimidin-7-yl]pyrrolidin-3-ol

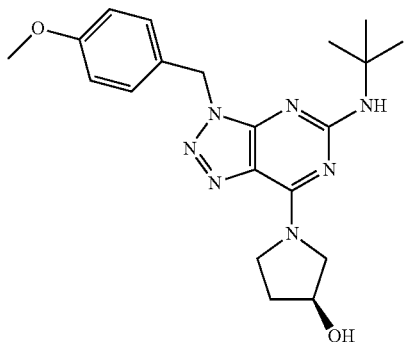 [SMILES: COc1ccc(Cn2nnc3c(N4CC[C@H](O)C4)nc(NC(C)(C)C)nc32)cc1]

a) 3-[(4-methoxyphenyl)methyl]-4H-triazolo[4,5-d]pyrimidine-5,7-dione

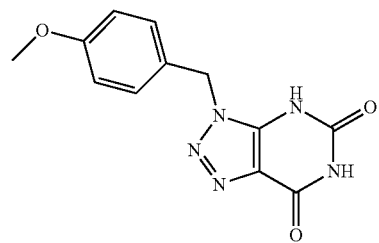 [SMILES: COc1ccc(Cn2nnc3c(=O)[nH]c(=O)[nH]c32)cc1]

A mixture of 5-amino-1-(4-methoxybenzyl)-1H-1,2,3-triazole-4-carboxamide (7.6 g, 30.7 mmol), sodium ethoxide (3.76 g, 55.3 mmol) and diethyl carbonate (4.72 g, 39.9 mmol) in ethanol (97.1 mL) was heated to reflux overnight. After cooling to room temperature the mixture was filtered and the precipitate was washed with ethanol to yield after drying 8.54 g (51%) of the title compound as white solid. MS(m/e): 272.0 (MH$^+$).

b) (3S)-1-[5-Chloro-3-[(4-methoxyphenyl)methyl]triazolo[4,5-d]pyrimidin-7-yl]pyrrolidin-3-ol

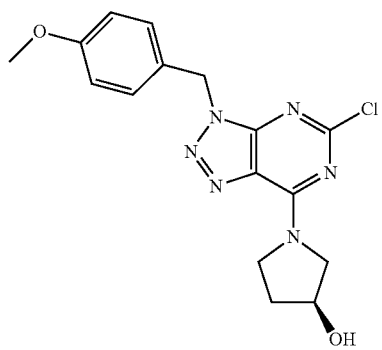 [SMILES: COc1ccc(Cn2nnc3c(N4CC[C@H](O)C4)nc(Cl)nc32)cc1]

A mixture of 3-[(4-methoxyphenyl)methyl]-4H-triazolo[4,5-d]pyrimidine-5,7-dione (5.2 g, 9.52 mmol), POCl$_3$ (73 g, 476 mmol) and N.N-diethylamine (2.56 g, 1.7 mmol) was heated to 120° C. for 4 h. The mixture was evaporated and the residue poured into ice/water (100 mL) and extracted with DCM (2×600 mL). The combined organic layers were dried with MgSO4, filtered and evaporated to yield crude 5,7-dichloro-3-[(4-methoxyphenyl)methyl]triazolo[4,5-d]pyrimidine which was used in the consecutive step without further purification.

A mixture of the crude 5,7-dichloro-3-[(4-methoxyphenyl)methyl]triazolo[4,5-d]pyrimidine (2.95 g), DIPEA (9.83 g, 76.1 mmol) and (S)-pyrrolidin-3-ol (1.82 g, 20.9 mmol) in DCM (150 mL) was stirred at room temperature for 30 min. The mixture was poured into water (150 mL) and extracted with DCM (2×125 mL). The combined organic layers were dried with MgSO$_4$, filtered and evaporated to yield the crude title compound as dark brown foam which was used in the consecutive step without further purification. MS(m/e): 361.3 (MH$^+$).

c) (3S)-1-[5-(tert-butylamino)-3-[(4-methoxyphenyl)methyl]triazolo[4,5-d]pyrimidin-7-yl]pyrrolidin-3-ol In analogy to the procedure described for the synthesis of 3-[(2-chlorophenyl)methyl]-7-(3,3-difluoropyrrolidin-1-yl)-N-ethyltriazolo[4,5-d]pyrimidin-5-amine (example 8) the title compound was prepared from (3S)-1-[5-chloro-3-[(4-methoxyphenyl)methyl]triazolo[4,5-d]pyrimidin-7-yl]pyrrolidin-3-ol and 2-methylpropan-2-amine. MS(m/e): 398.5 (MH$^+$).

Example 20

N-tert-Butyl-7-(3,3-difluoropyrrolidin-1-yl)-3-[(4-methoxyphenyl)methyl]triazolo [4,5-d]pyrimidin-5-amine

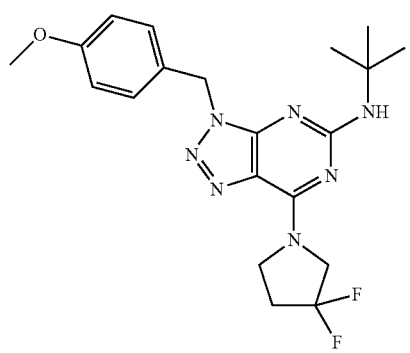 [SMILES: COc1ccc(Cn2nnc3c(N4CCC(F)(F)C4)nc(NC(C)(C)C)nc32)cc1]

a) 5-Chloro-7-(3,3-difluoropyrrolidin-1-yl)-3-[(4-methoxyphenyl)methyl]triazolo[4,5-d]pyrimidine

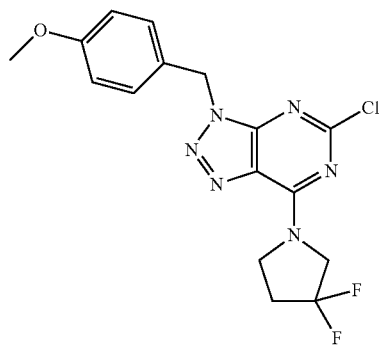 [SMILES: COc1ccc(Cn2nnc3c(N4CCC(F)(F)C4)nc(Cl)nc32)cc1]

In analogy to the procedure described for the synthesis of (3S)-1-[5-chloro-3-[(4-methoxyphenyl)methyl]triazolo[4,5-d]pyrimidin-7-yl]pyrrolidin-3-ol (example 19, step b) the title compounds was prepared from the crude 5,7-dichloro-3-[(4-methoxyphenyl)methyl]triazolo[4,5-d]pyrimidine and 3,3-difluoropyrrolidine hydrochloride as light brown solid. MS(m/e): 381.3 (MH+).

b) N-tert-Butyl-7-(3,3-difluoropyrrolidin-1-yl)-3-[(4-methoxyphenyl)methyl]triazolo[4,5-d]pyrimidin-5-amine In analogy to the procedure described for the synthesis of 3-[(2-chlorophenyl)methyl]-7-(3,3-difluoropyrrolidin-1-yl)-N-ethyltriazolo[4,5-d]pyrimidin-5-amine (example 8) the title compound was prepared from 5-chloro-7-(3,3-difluoropyrrolidin-1-yl)-3-[(4-methoxyphenyl)methyl]triazolo[4,5-d]pyrimidine and tert-butylamine as light yellow foam. MS(m/e): 418.5 (MH+).

Example 21

N-[(3S)-1-[5-(tert-Butylamino)-3-[(4-methoxyphenyl)methyl]triazolo[4,5-d]pyrimidin-7-yl]pyrrolidin-3-yl]acetamide

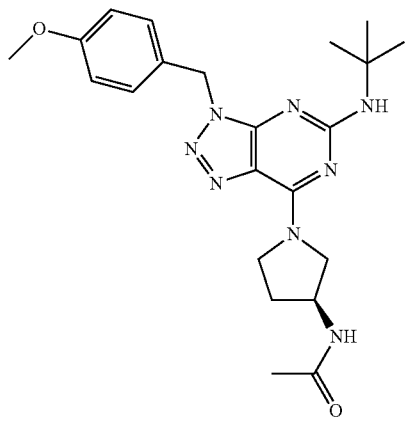 [SMILES: COc1ccc(Cn2nnc3c(N4CC[C@H](NC(C)=O)C4)nc(NC(C)(C)C)nc32)cc1]

a) N-[(3S)-1-[5-Chloro-3-[(4-methoxyphenyl)methyl]triazolo[4,5-d]pyrimidin-7-yl]pyrrolidin-3-yl]acetamide

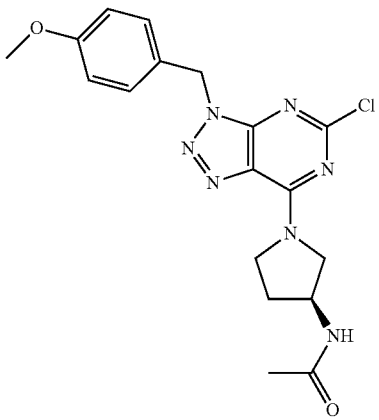 [SMILES: COc1ccc(Cn2nnc3c(N4CC[C@H](NC(C)=O)C4)nc(Cl)nc32)cc1]

In analogy to the procedure described for the synthesis of (3S)-1-[5-chloro-3-[(4-methoxyphenyl)methyl]triazolo[4,5-d]pyrimidin-7-yl]pyrrolidin-3-ol (example 19, step b) the title compounds was prepared from the crude 5,7-dichloro-3-[(4-methoxyphenyl)methyl]triazolo[4,5-d]pyrimidine and (S)—N-(pyrrolidin-3-yl)acetamide as light brown solid. MS(m/e): 402.4 (MH+).

b) N-[(3S)-1-[5-(tert-Butylamino)-3-[(4-methoxyphenyl)methyl]triazolo[4,5-d]pyrimidin-7-yl]pyrrolidin-3-yl]acetamide In analogy to the procedure described for the synthesis of 3-[(2-chlorophenyl)methyl]-7-(3,3-difluoropyrrolidin-1-yl)-N-ethyltriazolo[4,5-d]pyrimidin-5-amine (example 8) the title compound was prepared from N-[(3S)-1-[5-chloro-3-[(4-methoxyphenyl)methyl]triazolo [4,5-d]pyrimidin-7-yl]

pyrrolidin-3-yl]acetamide and tert-butylamine as light yellow foam. MS(m/e): 439.5 (MH⁺).

Example 22

N-tert-Butyl-7-(3,3-difluoropyrrolidin-1-yl)-3-[[2-(trifluoromethyl)phenyl]methyl]triazolo[4,5-d]pyrimidin-5-amine

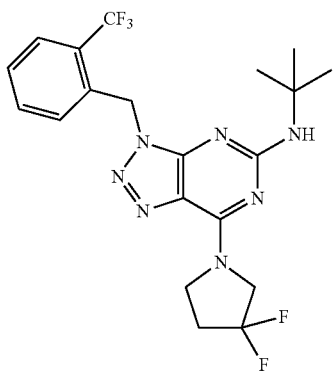 [SMILES: CC(C)(C)Nc1nc(N2CCC(F)(F)C2)c2nnn(Cc3ccccc3C(F)(F)F)c2n1]

a) N-tert-Butyl-7-(3,3-difluoropyrrolidin-1-yl)-3H-triazolo[4,5-d]pyrimidin-5-amine

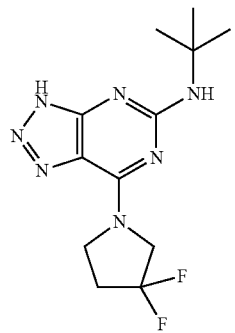 [SMILES: CC(C)(C)Nc1nc(N2CCC(F)(F)C2)c2nn[nH]c2n1]

N-tert-butyl-7-(3,3-Difluoropyrrolidin-1-yl)-3-[(4-methoxyphenyl)methyl]triazolo[4,5-d]pyrimidin-5-amine (example 20) was hydrogenated over Pd/C in methanol to yield the title compound which was used in the consecutive step without further purification.

b) N-tert-Butyl-7-(3,3-difluoropyrrolidin-1-yl)-3-[[2-(trifluoromethyl)phenyl]methyl]triazolo[4,5-d]pyrimidin-5-amine A mixture of N-tert-butyl-7-(3,3-difluoropyrrolidin-1-yl)-3H-triazolo[4,5-d]pyrimidin-5-amine (25 mg, 0.08 mmol), NEt₃ (14.6 mg, 0.144 mmol) and 1-(bromomethyl)-2-(trifluoromethyl)benzene (26.8 mg, 0.112 mmol) in 2 mL DMF was stirred at room temperature for 5 h. The mixture was subjected to purification by preparative HPLC on reversed phase eluting with a gradient formed from acetonitrile, water and NEt₃. After evaporation of the product containing fractions 5.2 mg (14%) of the title compound was isolated. MS(m/e): 456.4 (MH⁺).

Example 23

N-tert-Butyl-7-(3,3-difluoropyrrolidin-1-yl)-3-[(2-methyl sulfonylphenyl)methyl]triazolo[4,5-d]pyrimidin-5-amine

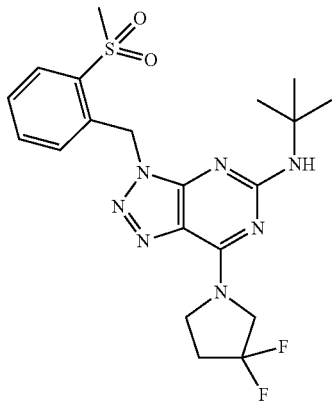 [SMILES: CC(C)(C)Nc1nc(N2CCC(F)(F)C2)c2nnn(Cc3ccccc3S(C)(=O)=O)c2n1]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from N-tert-butyl-7-(3,3-difluoropyrrolidin-1-yl)-3H-triazolo[4,5-d]pyrimidin-5-amine and 1-(bromomethyl)-2-(methylsulfonyl)benzene. MS(m/e): 466.4 (MH⁺).

Example 24

N-tert-Butyl-3-[(3-chloropyridin-2-yl)methyl]-7-(3,3-difluoropyrrolidin-1-yl)triazolo[4,5-d]pyrimidin-5-amine

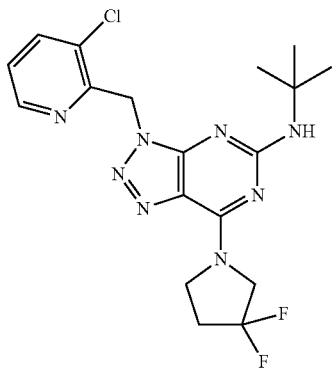

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from N-tert-butyl-7-(3,3-difluoropyrrolidin-1-yl)-3H-triazolo[4,5-d]pyrimidin-5-amine and 3-chloro-2-(chloromethyl)pyridine. MS(m/e): 423.3 (MH⁺).

Example 25

N-tert-Butyl-7-(3,3-difluoropyrrolidin-1-yl)-3-[(1-methyltetrazol-5-yl)methyl]triazolo [4,5-d]pyrimidin-5-amine

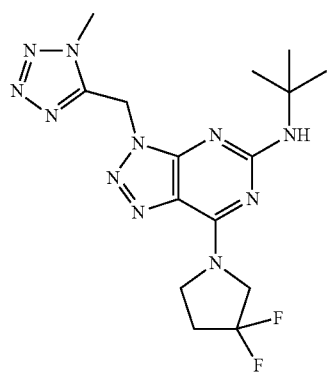 [SMILES: Cn1nnnc1Cn1nnc2c(N3CCC(F)(F)C3)nc(NC(C)(C)C)nc21]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from N-tert-butyl-7-(3,3-difluoropyrrolidin-1-yl)-3H-triazolo[4,5-d]pyrimidin-5-amine and 5-(chloromethyl)-1-methyl-1H-tetrazole. MS(m/e): 394.4 (MH$^+$).

Example 26

N-tert-Butyl-7-(3,3-difluoropyrrolidin-1-yl)-3-[(4-methyl-1,2,5-oxadiazol-3-yl)methyl]triazolo[4,5-d]pyrimidin-5-amine

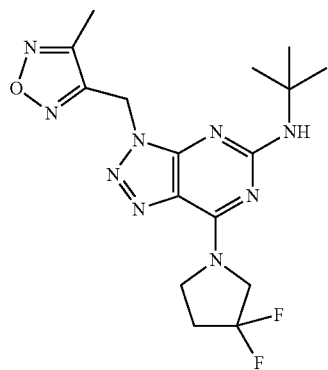 [SMILES: Cc1nonc1Cn1nnc2c(N3CCC(F)(F)C3)nc(NC(C)(C)C)nc21]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from N-tert-butyl-7-(3,3-difluoropyrrolidin-1-yl)-3H-triazolo[4,5-d]pyrimidin-5-amine and 3-(bromomethyl)-4-methyl-1,2,5-oxadiazole. MS(m/e): 394.4 (MH$^+$).

Example 27

N-[(3S)-1-[5-(tert-Butylamino)-3-[(3-chloropyridin-2-yl)methyl]triazolo[4,5-d]pyrimidin-7-yl]pyrrolidin-3-yl]acetamide

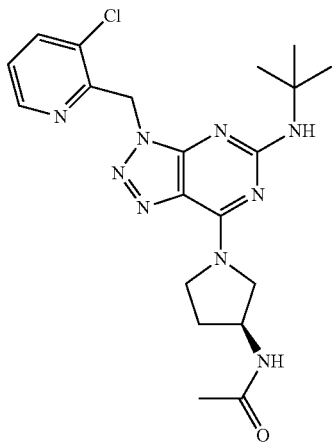 [SMILES: CC(=O)N[C@H]1CCN(c2nc(NC(C)(C)C)nc3c2nnn3Cc2ncccc2Cl)C1]

a) N-[(3S)-1-[5-(tert-Butylamino)-3H-triazolo[4,5-d]pyrimidin-7-yl]pyrrolidin-3-yl]acetamide

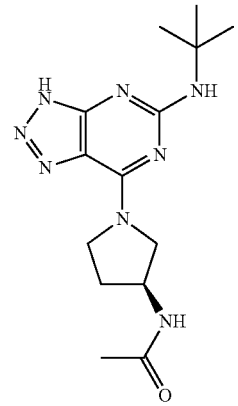 [SMILES: CC(=O)N[C@H]1CCN(c2nc(NC(C)(C)C)nc3[nH]nnc23)C1]

N-[(3S)-1-[5-(tert-Butylamino)-3-[(4-methoxyphenyl)methyl]triazolo[4,5-d]pyrimidin-7-yl]pyrrolidin-3-yl]acetamide (example 21) was hydrogenated over Pd/C in methanol to yield the title compound which was used in the consecutive step without further purification.

b) N-[(3S)-1-[5-(tert-Butylamino)-3-[(3-chloropyridin-2-yl)methyl]triazolo[4,5-d]pyrimidin-7-yl]pyrrolidin-3-yl]acetamide In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from N-[(3S)-1-[5-(tert-butylamino)-3H-triazolo[4,5-d]pyrimidin-7-yl]pyrrolidin-3-yl]acetamide and 3-chloro-2-(chloromethyl)pyridine. MS(m/e): 444.4 (MH$^+$).

Example 28

(3S)-1-[5-(tert-Butylamino)-3-[(2-chlorophenyl)methyl]triazolo[4,5-d]pyrimidin-7-yl]pyrrolidin-3-ol

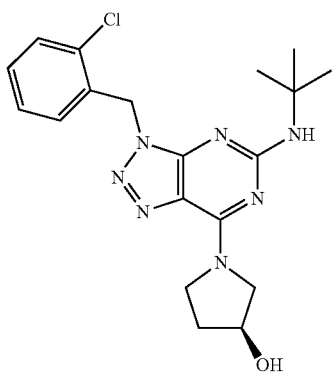

a) (3S)-1-[5-(tert-Butylamino)-3H-triazolo[4,5-d]pyrimidin-7-yl]pyrrolidin-3-ol

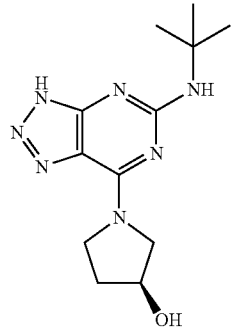 [SMILES: CC(C)(C)Nc1nc(N2CC[C@H](O)C2)c2nn[nH]c2n1]

(3S)-1-[5-(tert-Butylamino)-3-[(4-methoxyphenyl)methyl]triazolo[4,5-d]pyrimidin-7-yl]pyrrolidin-3-ol (example 19) was hydrogenated over Pd/C in methanol to yield the title compound which was used in the consecutive step without further purification.

b) (3S)-1-[5-(tert-Butylamino)-3-[(2-chlorophenyl)methyl]triazolo[4,5-d]pyrimidin-7-yl]pyrrolidin-3-ol In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from (3S)-1-[5-(tert-butylamino)-3H-triazolo[4,5-d]pyrimidin-7-yl]pyrrolidin-3-ol and 1-(bromomethyl)-2-chlorobenzene. MS(m/e): 402.3 (MH$^+$).

Example 29

(3S)-1-[5-(tert-Butylamino)-3-[(1-methyltetrazol-5-yl)methyl]triazolo[4,5-d]pyrimidin-7-yl]pyrrolidin-3-ol

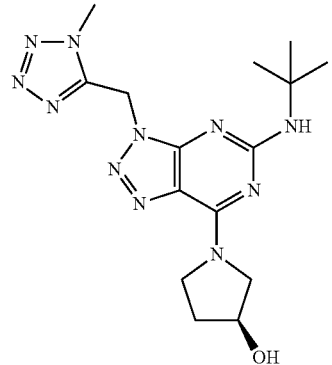 [SMILES: Cn1nnnc1Cn1nnc2c(N3CC[C@H](O)C3)nc(NC(C)(C)C)nc21]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from (3S)-1-[5-(tert-butylamino)-3H-triazolo[4,5-d]pyrimidin-7-yl]pyrrolidin-3-ol and 5-(chloromethyl)-1-methyl-1H-tetrazole. MS(m/e): 374.3 (MH$^+$).

Example 30

(3S)-1-[5-(tert-Butylamino)-3-[(4-methoxyphenyl)methyl]triazolo[4,5-d]pyrimidin-7-yl]-3-methylpyrrolidin-3-ol

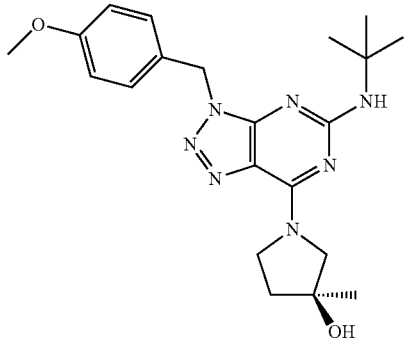 [SMILES: COc1ccc(Cn2nnc3c(N4CC[C@](C)(O)C4)nc(NC(C)(C)C)nc32)cc1]

a) (3S)-1-[5-Chloro-3-[(4-methoxyphenyl)methyl]triazolo[4,5-d]pyrimidin-7-yl]-3-methyl-pyrrolidin-3-ol

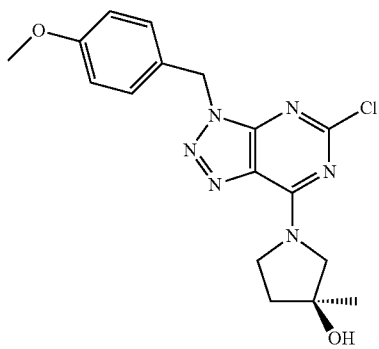 [SMILES: COc1ccc(Cn2nnc3c(N4CC[C@](C)(O)C4)nc(Cl)nc32)cc1]

In analogy to the procedure described for the synthesis of (3S)-1-[5-chloro-3-[(4-methoxyphenyl)methyl]triazolo[4,5-d]pyrimidin-7-yl]pyrrolidin-3-ol (example 19, step b) the title compounds was prepared from the crude 5,7-dichloro-3-[(4-methoxyphenyl) methyl]triazolo[4,5-d]pyrimidine and 3-methylpyrrolidin-3-ol. The two enantiomers were separated by preparative HPLC on chiral phase. MS(m/e): 375.4 (MH+).

b) (3S)-1-[5-(tert-Butylamino)-3-[(4-methoxyphenyl)methyl]triazolo[4,5-d]pyrimidin-7-yl]-3-methyl-pyrrolidin-3-ol In analogy to the procedure described for the synthesis of 3-[(2-chlorophenyl)methyl]-7-(3,3-difluoropyrrolidin-1-yl)-N-ethyltriazolo[4,5-d]pyrimidin-5-amine (example 8) the title compound was prepared from (3S)-1-[5-chloro-3-[(4-methoxyphenyl)methyl]triazolo[4,5-d]pyrimidin-7-yl]-3-methyl-pyrrolidin-3-ol and tert-butylamine. MS(m/e): 412.3 (MH+).

Example 31

(3R)-1-[5-(tert-Butylamino)-3-[(4-methoxyphenyl)methyl]triazolo[4,5-d]pyrimidin-7-yl]-3-methylpyrrolidin-3-ol

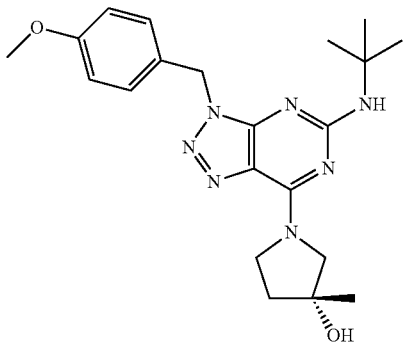 [SMILES: COc1ccc(Cn2nnc3c(N4CC[C@@](C)(O)C4)nc(NC(C)(C)C)nc32)cc1]

In analogy to the procedure described for the synthesis of 3-[(2-chlorophenyl)methyl]-7-(3,3-difluoropyrrolidin-1-yl)-N-ethyltriazolo[4,5-d]pyrimidin-5-amine (example 8) the title compound was prepared from (3R)-1-[5-chloro-3-[(4-methoxyphenyl)methyl]triazolo[4,5-d]pyrimidin-7-yl]-3-methyl-pyrrolidin-3-ol (isolated as described in example 30) and tert-butylamine. MS(m/e): 412.3 (MH+).

Example 32

(3S)-1-[3-[(2-Chlorophenyl)methyl]-5-morpholino-triazolo[4,5-d]pyrimidin-7-yl]-3-methyl-pyrrolidin-3-ol

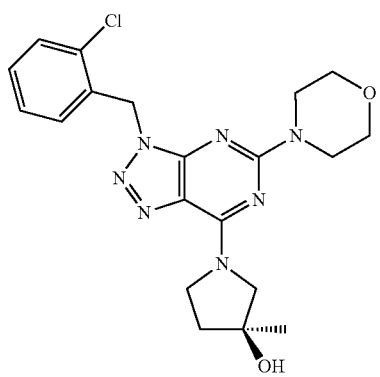 [SMILES: C[C@]1(O)CCN(c2nc(N3CCOCC3)nc3c2nnn3Cc2ccccc2Cl)C1]

a) (3S)-1-[3-[(4-Methoxyphenyl)methyl]-5-morpholino-triazolo[4,5-d]pyrimidin-7-yl]-3-methyl-pyrrolidin-3-ol

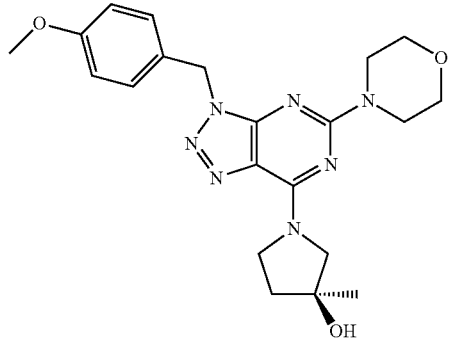 [SMILES: COc1ccc(Cn2nnc3c(N4CC[C@](C)(O)C4)nc(N4CCOCC4)nc32)cc1]

In analogy to the procedure described for the synthesis of 3-[(2-chlorophenyl)methyl]-7-(3,3-difluoropyrrolidin-1-yl)-N-ethyltriazolo[4,5-d]pyrimidin-5-amine (example 8) the title compound was prepared from (3S)-1-[5-chloro-3-[(4-methoxyphenyl)methyl]triazolo[4,5-d]pyrimidin-7-yl]-3-methyl-pyrrolidin-3-ol and morpholine. MS(m/e): 426.4 (MH+).

b) (3S)-3-Methyl-1-(5-morpholino-3H-triazolo[4,5-d]pyrimidin-7-yl)pyrrolidin-3-ol

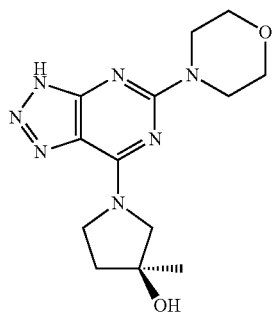 [SMILES: C[C@]1(O)CCN(c2nc(N3CCOCC3)nc3[nH]nnc23)C1]

(3S)-1-[3-[(4-methoxyphenyl)methyl]-5-morpholino-triazolo[4,5-d]pyrimidin-7-yl]-3-methyl-pyrrolidin-3-ol (0.45 g, 1 mmol) in TFA (3.87 mL) was heated to 80° C. for 4 h and evaporated. The crude product was used in the consecutive step without further purification. MS(m/e): 306.2 (MH+).

c) (3S)-1-[3-[(2-Chlorophenyl)methyl]-5-morpholino-triazolo[4,5-d]pyrimidin-7-yl]-3-methyl-pyrrolidin-3-ol In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from (3S)-3-methyl-1-(5-morpholino-3H-triazolo[4,5-d]pyrimidin-7-yl)pyrrolidin-3-ol and 1-(bromomethyl)-2-chlorobenzene. MS(m/e): 430.3 (MH+).

Example 33

(3S)-3-Methyl-1-[5-morpholin-4-yl-3-[[2-(trifluoromethyl)phenyl]methyl]triazolo[4,5-d]pyrimidin-7-yl]pyrrolidin-3-ol

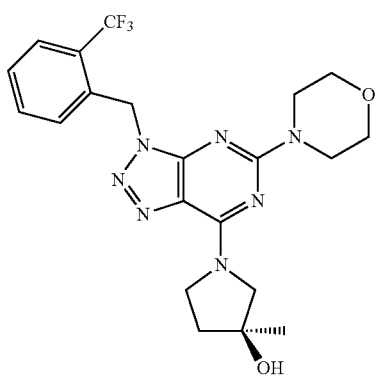 [SMILES: C[C@]1(O)CCN(c2nc(N3CCOCC3)nc3c2nnn3Cc2ccccc2C(F)(F)F)C1]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from (3S)-3-methyl-1-(5-morpholino-3H-triazolo[4,5-d]pyrimidin-7-yl)pyrrolidin-3-ol and 1-(bromomethyl)-2-(trifluoromethyl)benzene. MS(m/e): 464.4 (MH$^+$).

Example 34

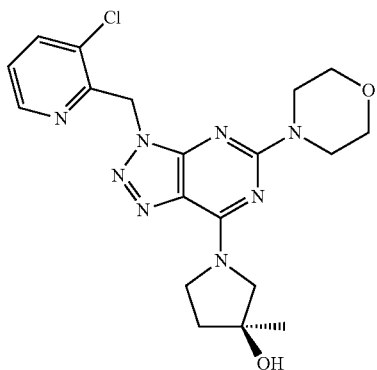

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from (3S)-3-methyl-1-(5-morpholino-3H-triazolo[4,5-d]pyrimidin-7-yl)pyrrolidin-3-ol and 3-chloro-2-(chloromethyl)pyridine. MS(m/e): 431.3 (MH$^+$).

Example 35

(3S)-3-Methyl-1-[3-[(3-methyl-1,2,4-oxadiazol-5-yl)methyl]-5-morpholin-4-yltriazolo[4,5-d]pyrimidin-7-yl]pyrrolidin-3-ol

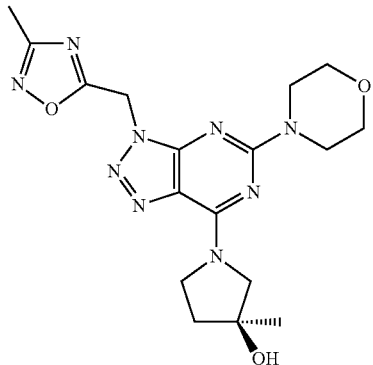 [SMILES: Cc1noc(Cn2nnc3c(N4CC[C@](C)(O)C4)nc(N4CCOCC4)nc32)n1]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from (3S)-3-methyl-1-(5-morpholino-3H-triazolo[4,5-d]pyrimidin-7-yl)pyrrolidin-3-ol and 5-(chloromethyl)-3-methyl-1,2,4-oxadiazole. MS(m/e): 402.3 (MH$^+$).

Example 36

(3R)-1-[3-[(2-Chlorophenyl)methyl]-5-morpholin-4-yltriazolo[4,5-d]pyrimidin-7-yl]-3-methylpyrrolidin-3-ol

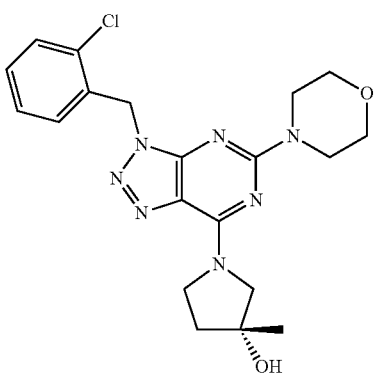 [SMILES: C[C@@]1(O)CCN(c2nc(N3CCOCC3)nc3c2nnn3Cc2ccccc2Cl)C1]

a) (3R)-1-[3-[(4-Methoxyphenyl)methyl]-5-morpholino-triazolo[4,5-d]pyrimidin-7-yl]-3-methyl-pyrrolidin-3-ol

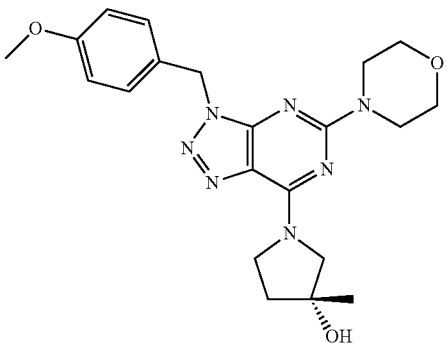 [SMILES: COc1ccc(Cn2nnc3c(N4CC[C@@](C)(O)C4)nc(N4CCOCC4)nc32)cc1]

In analogy to the procedure described for the synthesis of 3-[(2-chlorophenyl)methyl]-7-(3,3-difluoropyrrolidin-1-yl)-N-ethyltriazolo[4,5-d]pyrimidin-5-amine (example 8) the title compound was prepared from (3R)-1-[5-chloro-3-[(4-methoxyphenyl)methyl]triazolo[4,5-d]pyrimidin-7-yl]-3-methyl-pyrrolidin-3-ol and morpholine. MS(m/e): 426.4 (MH⁺).

b) (3R)-3-Methyl-1-(5-morpholino-3H-triazolo[4,5-d]pyrimidin-7-yl)pyrrolidin-3-ol

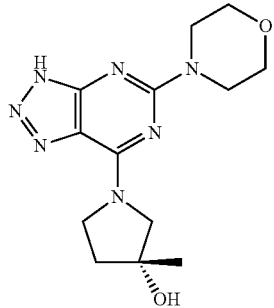 [SMILES: C[C@@]1(O)CCN(c2nc(N3CCOCC3)nc3[nH]nnc23)C1]

(3R)-1-[3-[(4-Methoxyphenyl)methyl]-5-morpholino-triazolo[4,5-d]pyrimidin-7-yl]-3-methyl-pyrrolidin-3-ol (0.45 g, 1 mmol) in TFA (3.87 mL) was heated to 80° C. for 4 h and evaporated. The crude product was used in the consecutive step without further purification. MS(m/e): 306.2 (MH⁺).

c) (3R)-1-[3-[(2-Chlorophenyl)methyl]-5-morpholino-triazolo[4,5-d]pyrimidin-7-yl]-3-methyl-pyrrolidin-3-ol In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from (3R)-3-methyl-1-(5-morpholino-3H-triazolo[4,5-d]pyrimidin-7-yl)pyrrolidin-3-ol and 1-(bromomethyl)-2-chlorobenzene. MS(m/e): 430.3 (MH⁺).

Example 37

(3R)-3-Methyl-1-[5-morpholin-4-yl-3-[[2-(trifluoromethyl)phenyl]methyl]triazolo[4,5-d]pyrimidin-7-yl]pyrrolidin-3-ol

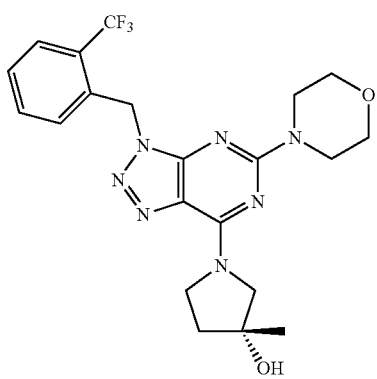 [SMILES: C[C@@]1(O)CCN(c2nc(N3CCOCC3)nc3c2nnn3Cc2ccccc2C(F)(F)F)C1]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from (3R)-3-methyl-1-(5-morpholino-3H-triazolo[4,5-d]pyrimidin-7-yl)pyrrolidin-3-ol and 1-(bromomethyl)-2-(trifluoromethyl)benzene. MS(m/e): 464.3 (MH⁺).

Example 38

(3R)-3-Methyl-1-[3-[(2-methylsulfonylphenyl)methyl]-5-morpholin-4-yltriazolo[4,5-d]pyrimidin-7-yl]pyrrolidin-3-ol

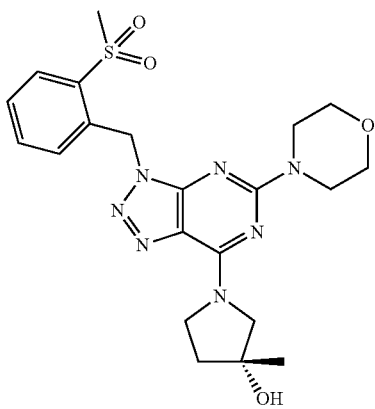 [SMILES: C[C@@]1(O)CCN(c2nc(N3CCOCC3)nc3c2nnn3Cc2ccccc2S(C)(=O)=O)C1]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from (3R)-3-methyl-1-(5-morpholino-3H-triazolo[4,5-d]pyrimidin-7-yl)pyrrolidin-3-ol and 1-(bromomethyl)-2-(methyl sulfonyl)benzene. MS(m/e): 474.3 (MH⁺).

Example 39

(3R)-3-Methyl-1-[3-[(3-methyl-1,2,4-oxadiazol-5-yl)methyl]-5-morpholin-4-yltriazolo[4,5-d]pyrimidin-7-yl]pyrrolidin-3-ol

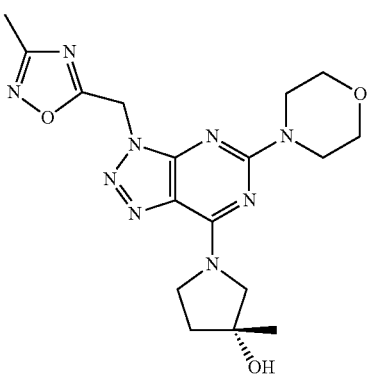 [SMILES: Cc1noc(Cn2nnc3c(N4CC[C@@](C)(O)C4)nc(N4CCOCC4)nc32)n1]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from (3R)-3-methyl-1-(5-morpholino-3H-triazolo[4,5-d]pyrimidin-7-yl)pyrrolidin-3-ol and 5-(chloromethyl)-3-methyl-1,2,4-oxadiazole. MS(m/e): 402.3 (MH+).

Example 40

3-[(2-Chlorophenyl)methyl]-7-(3,3-difluoropyrrolidin-1-yl)-5-(2,2,2-trifluoroethoxy) triazolo[4,5-d]pyrimidine

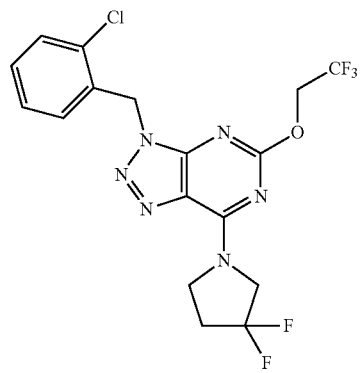 [SMILES: FC(F)(F)COc1nc(N2CCC(F)(F)C2)c2nnn(Cc3ccccc3Cl)c2n1]

A mixture of 5-chloro-3-[(2-chlorophenyl)methyl]-7-(3,3-difluoropyrrolidin-1-yl)triazolo[4,5-d]pyrimidine (example 8, step a) (38.5 mg, 0.1 mmol), 2,2,2-Trifluoroethanol (99 mg, 1 mmol) and NaH (suspension in oil, 20 mg, 5 mmol) in DMF (1 mL) was stirred at 110° C. for 6 h. After cooling to room temperature formic acid was added and the mixture was subjected to purification by preparative HPLC on reversed phase eluting with a gradient formed from acetonitrile, water and formic acid. After evaporation of the product containing fractions 29.3 mg (65%) of the title compound was isolated. MS(m/e): 449.2 (MH+).

Example 41

3-[(2-Chlorophenyl)methyl]-7-(3,3-difluoropyrrolidin-1-yl)-5-(1,1,1-trifluoropropan-2-yloxy)triazolo[4,5-d]pyrimidine

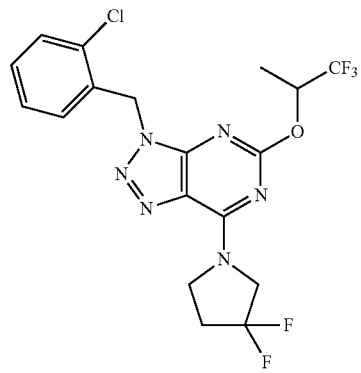 [SMILES: CC(Oc1nc(N2CCC(F)(F)C2)c2nnn(Cc3ccccc3Cl)c2n1)C(F)(F)F]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-3-[(2-chlorophenyl)methyl]-7-(3,3-difluoropyrrolidin-1-yl)triazolo[4,5-d]pyrimidine and 1,1,1-trifluoropropan-2-ol. MS(m/e): 463.2 (MH+).

3-[(2-Chlorophenyl)methyl]-7-(3,3-difluoropyrrolidin-1-yl)-5-[(2S)-1,1,1-trifluoropropan-2-yl]oxytriazolo[4,5-d]pyrimidine

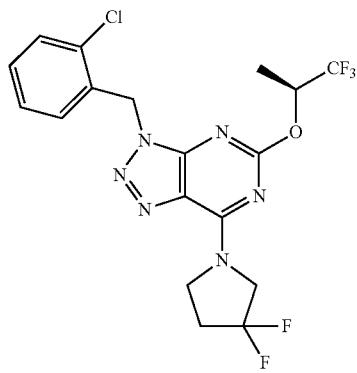 [SMILES: C[C@H](Oc1nc(N2CCC(F)(F)C2)c2nnn(Cc3ccccc3Cl)c2n1)C(F)(F)F]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-3-[(2-chlorophenyl)methyl]-7-(3,3-difluoropyrrolidin-1-yl)triazolo[4,5-d]pyrimidine and (S)-1,1,1-trifluoropropan-2-ol. MS(m/e): 463.3 (MH+).

Example 43

3-[(2-Chlorophenyl)methyl]-5-(2,2-difluoroethoxy)-7-(3,3-difluoropyrrolidin-1-yl)triazolo[4,5-d]pyrimidine

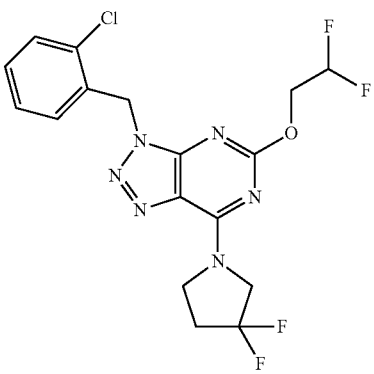 [SMILES: FC(F)COc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-3-[(2-chlorophenyl)methyl]-7-(3,3-difluoropyrrolidin-1-yl)triazolo[4,5-d]pyrimidine and 2,2-difluoroethanol. MS(m/e): 431.3 (MH+).

Example 44

3-[(2-Chlorophenyl)methyl]-7-(3,3-difluoropyrrolidin-1-yl)-5-ethoxytriazolo[4,5-d]pyrimidine

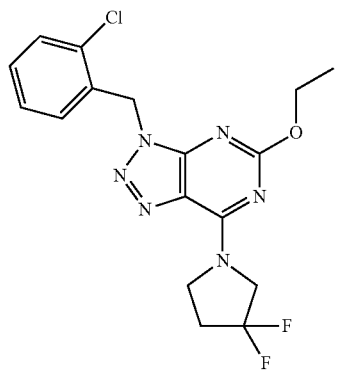 [SMILES: CCOc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-3-[(2-chlorophenyl)methyl]-7-(3,3-difluoropyrrolidin-1-yl)triazolo[4,5-d]pyrimidine and ethanol with the use of $Cs_2CO_3$ instead of NaH. MS(m/e): 395.3 (MH$^+$).

Example 45

5-Butoxy-3-[(2-chlorophenyl)methyl]-7-(3,3-difluoropyrrolidin-1-yl)triazolo[4,5-d]pyrimidine

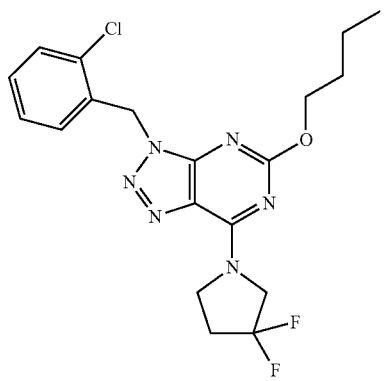 [SMILES: CCCCOc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-3-[(2-chlorophenyl)methyl]-7-(3,3-difluoropyrrolidin-1-yl)triazolo[4,5-d]pyrimidine and butanol with the use of $Cs_2CO_3$ instead of NaH. MS(m/e): 423.3 (MH$^+$).

Example 46

3-[(2-Chlorophenyl)methyl]-7-(3,3-difluoropyrrolidin-1-yl)-5-(2-fluoroethoxy) triazolo[4,5-d]pyrimidine

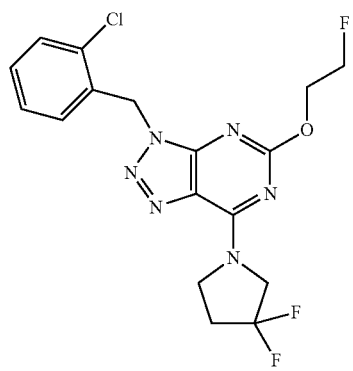 [SMILES: FCCOc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-3-[(2-chlorophenyl)methyl]-7-(3,3-difluoropyrrolidin-1-yl)triazolo[4,5-d]pyrimidine and 2-fluoroethanol with the use of $Cs_2CO_3$ instead of NaH. MS(m/e): 413.2 (MH$^+$).

Example 47

3-[(2-Chlorophenyl)methyl]-5-(cyclopropylmethoxy)-7-(3,3-difluoropyrrolidin-1-yl)triazolo[4,5-d]pyrimidine

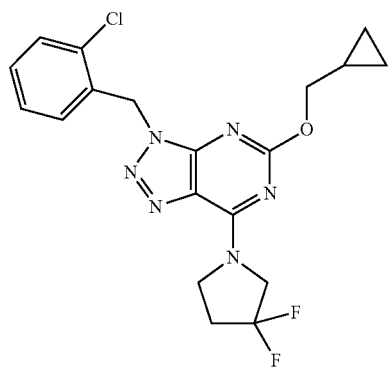 [SMILES: FC1(F)CCN(c2nc(OCC3CC3)nc3c2nnn3Cc2ccccc2Cl)C1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-3-[(2-chlorophenyl)methyl]-7-(3,3-difluoropyrrolidin-1-yl)triazolo[4,5-d]pyrimidine and cyclopropylmethanol with the use of $Cs_2CO_3$ instead of NaH. MS(m/e): 421.3 (MH$^+$).

Example 48

3-[(2-Chlorophenyl)methyl]-5-cyclobutyloxy-7-(3,3-difluoropyrrolidin-1-yl)triazolo[4,5-d]pyrimidine

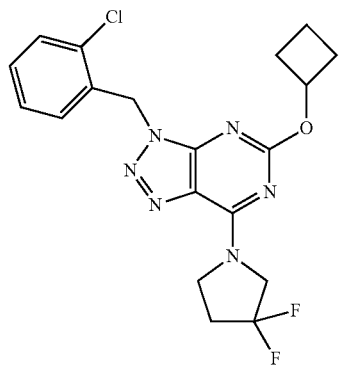 [SMILES: FC1(F)CCN(c2nc(OC3CCC3)nc3c2nnn3Cc2ccccc2Cl)C1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-3-[(2-chlorophenyl)methyl]-7-(3,3-difluoropyrrolidin-1-yl)triazolo[4,5-d]pyrimidine and cyclobutanol with the use of $Cs_2CO_3$ instead of NaH. MS(m/e): 421.3 (MH$^+$).

Example 49

3-[(2-Chlorophenyl)methyl]-7-(3,3-difluoropyrrolidin-1-yl)-5-(oxetan-3-yloxy)triazolo [4,5-d]pyrimidine

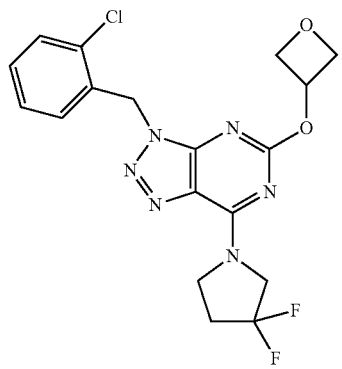

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-3-[(2-chlorophenyl)methyl]-7-(3,3-difluoropyrrolidin-1-yl)triazolo[4,5-d]pyrimidine and oxetan-3-ol with the use of $Cs_2CO_3$ instead of NaH. MS(m/e): 423.3 (MH$^+$).

Example 50

3-[(2-Chlorophenyl)methyl]-7-(3,3-difluoropyrrolidin-1-yl)-5-[(3-methyloxetan-3-yl)methoxy]triazolo[4,5-d]pyrimidine

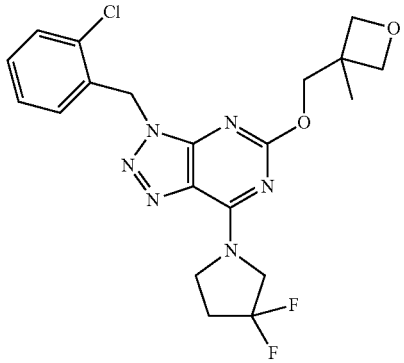 [SMILES: CC1(COc2nc(N3CCC(F)(F)C3)c3nnn(Cc4ccccc4Cl)c3n2)COC1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-3-[(2-chlorophenyl)methyl]-7-(3,3-difluoropyrrolidin-1-yl)triazolo[4,5-d]pyrimidine and (3-methyloxetan-3-yl)methanol with the use of $Cs_2CO_3$ instead of NaH. MS(m/e): 451.3 (MH$^+$).

Example 51

3-[(2-Chlorophenyl)methyl]-7-(3,3-difluoropyrrolidin-1-yl)-5-[(2R)-1,1,1-trifluoropropan-2-yl]oxytriazolo[4,5-d]pyrimidine

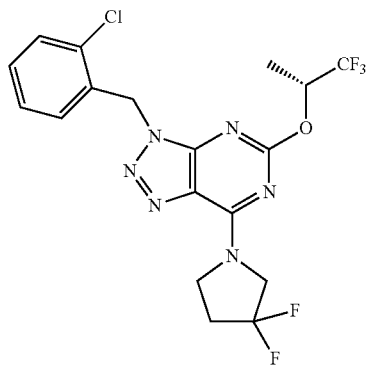 [SMILES: C[C@@H](Oc1nc(N2CCC(F)(F)C2)c2nnn(Cc3ccccc3Cl)c2n1)C(F)(F)F]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-3-[(2-chlorophenyl)methyl]-7-(3,3-difluoropyrrolidin-1-yl)triazolo[4,5-d]pyrimidine and (R)-1,1,1-trifluoropropan-2-ol with the use of $Cs_2CO_3$ instead of NaH. MS(m/e): 463.3 (MH$^+$).

Example 52

3-[(2-Chlorophenyl)methyl]-7-(3,3-difluoropyrrolidin-1-yl)-5-(2,2-dimethylpropoxy) triazolo[4,5-d]pyrimidine

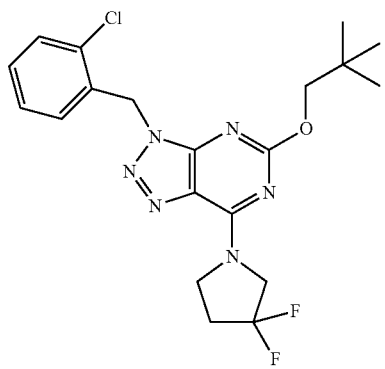 [SMILES: CC(C)(C)COc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-3-[(2-chlorophenyl)methyl]-7-(3,3-difluoropyrrolidin-1-yl)triazolo[4,5-d]pyrimidine and 2,2-dimethylpropan-1-ol with the use of $Cs_2CO_3$ instead of NaH. MS(m/e): 437.3 (MH$^+$).

Example 53

3-[(2-Chlorophenyl)methyl]-5-(2,2-difluoropropoxy)-7-(3,3-difluoropyrrolidin-1-yl)triazolo[4,5-d]pyrimidine

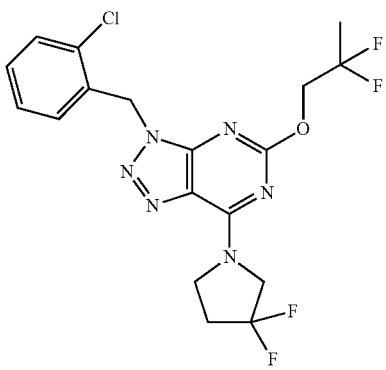 [SMILES: CC(F)(F)COc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-3-[(2-chlorophenyl)methyl]-7-(3,3-difluoropyrrolidin-1-yl)triazolo[4,5-d]pyrimidine and 2,2-difluoropropan-1-ol with the use of $Cs_2CO_3$ instead of NaH. MS(m/e): 445.3 (MH$^+$).

Example 54

3-[(2-Chlorophenyl)methyl]-7-(3,3-difluoropyrrolidin-1-yl)-5-(2-methylpropoxy) triazolo[4,5-d]pyrimidine

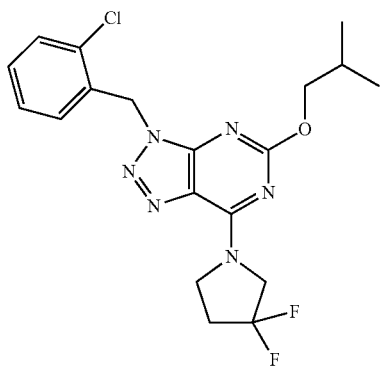 [SMILES: CC(C)COc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-3-[(2-chlorophenyl)methyl]-7-(3,3-difluoropyrrolidin-1-yl)triazolo[4,5-d]pyrimidine and 2-methylpropan-1-ol with the use of $Cs_2CO_3$ instead of NaH. MS(m/e): 423.3 (MH$^+$).

Example 55

3-[(2-Chlorophenyl)methyl]-7-(3,3-difluoropyrrolidin-1-yl)-5-propan-2-yloxytriazolo [4,5-d]pyrimidine

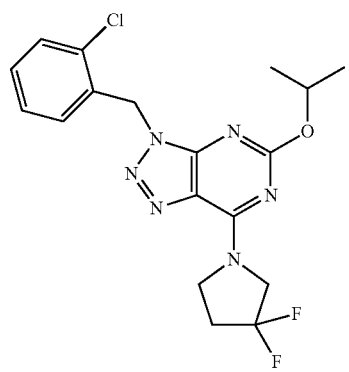 [SMILES: CC(C)Oc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-3-[(2-chlorophenyl)methyl]-7-(3,3-difluoropyrrolidin-1-yl)triazolo[4,5-d]pyrimidine and propan-2-ol with the use of $Cs_2CO_3$ instead of NaH. MS(m/e): 409.3 (MH$^+$).

Example 56

3-[(2-Chlorophenyl)methyl]-7-(3,3-difluoropyrrolidin-1-yl)-5-prop-2-ynoxytriazolo [4,5-d]pyrimidine

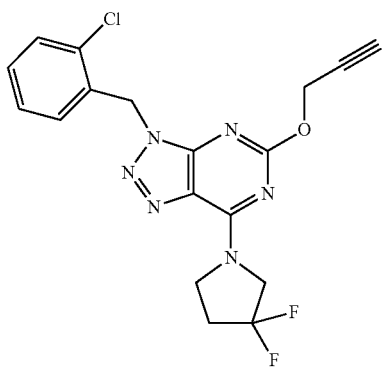 [SMILES: C#CCOc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-3-[(2-chlorophenyl)methyl]-7-(3,3-difluoropyrrolidin-1-yl)triazolo[4,5-d]pyrimidine and prop-2-yn-1-ol with the use of $Cs_2CO_3$ instead of NaH. MS(m/e): 405.2 (MH$^+$).

Example 57

3-[(2-Chlorophenyl)methyl]-7-(3,3-difluoropyrrolidin-1-yl)-5-(1-methoxypropan-2-yloxy)triazolo[4,5-d]pyrimidine

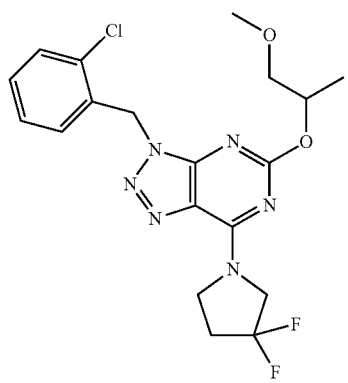 [SMILES: COCC(C)Oc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-3-[(2-chlorophenyl)methyl]-7-(3,3-difluoropyrrolidin-1-yl)triazolo[4,5-d]pyrimidine and 1-methoxypropan-2-ol with the use of $Cs_2CO_3$ instead of NaH. MS(m/e): 439.3 (MH$^+$).

Example 58

1-[3-[(2-Chlorophenyl)methyl]-7-(3,3-difluoropyrrolidin-1-yl)triazolo[4,5-d]pyrimidin-5-yl]oxy-2-methylpropan-2-ol

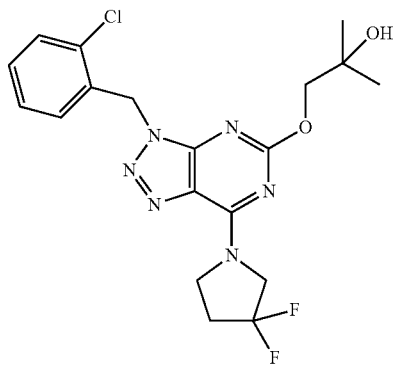 [SMILES: CC(C)(O)COc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-3-[(2-chlorophenyl)methyl]-7-(3,3-difluoropyrrolidin-1-yl)triazolo[4,5-d]pyrimidine and 2-methylpropane-1,2-diol with the use of $Cs_2CO_3$ instead of NaH. MS(m/e): 439.3 (MH$^+$).

Example 59

3-[(2-Chlorophenyl)methyl]-7-(3,3-difluoropyrrolidin-1-yl)-5-propoxytriazolo[4,5-d]pyrimidine

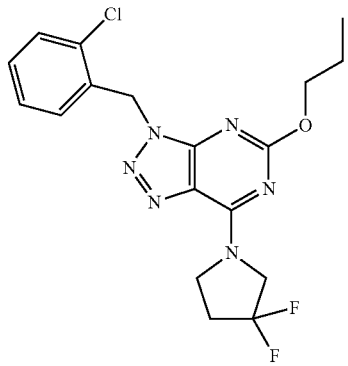 [SMILES: CCCOc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-3-[(2-chlorophenyl)methyl]-7-(3,3-difluoropyrrolidin-1-yl)triazolo[4,5-d]pyrimidine and propanol with the use of $Cs_2CO_3$ instead of NaH. MS(m/e): 409.3 (MH$^+$).

Example 60

(3S)-1-[3-[(2-Chlorophenyl)methyl]-5-(2,2,2-trifluoroethoxy)triazolo[4,5-d]pyrimidin-7-yl]pyrrolidin-3-ol

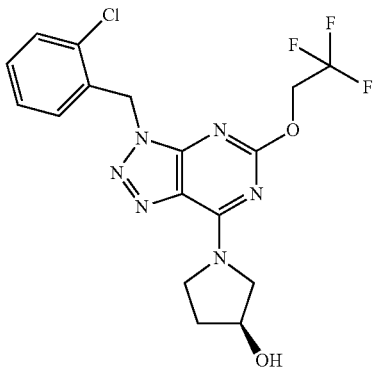 [SMILES: O[C@H]1CCN(c2nc(OCC(F)(F)F)nc3c2nnn3Cc2ccccc2Cl)C1]

a) (3S)-1-[3-[(4-Methoxyphenyl)methyl]-5-(2,2,2-trifluoroethoxy)triazolo[4,5-d]pyrimidin-7-yl]pyrrolidin-3-ol

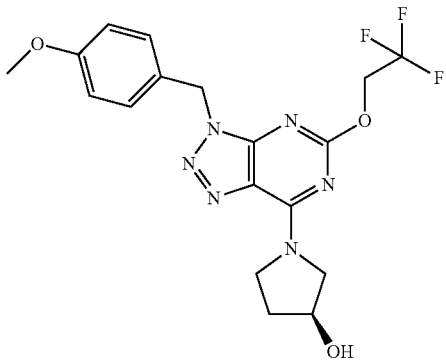 [SMILES: COc1ccc(Cn2nnc3c(N4CC[C@H](O)C4)nc(OCC(F)(F)F)nc32)cc1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from (3S)-1-[5-chloro-3-[(4-methoxyphenyl)methyl]triazolo[4,5-d]pyrimidin-7-yl]pyrrolidin-3-ol (example 19, step b) and 1,1,1-trifluoropropan-2-ol. MS(m/e): 425.4 (MH$^+$).

b) (3S)-1-[5-(2,2,2-Trifluoroethoxy)-3H-triazolo[4,5-d]pyrimidin-7-yl]pyrrolidin-3-ol

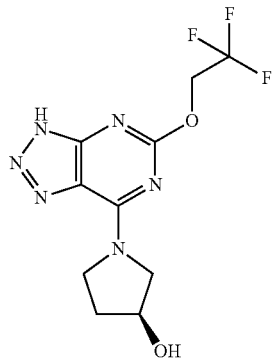 [SMILES: O[C@H]1CCN(c2nc(OCC(F)(F)F)nc3[nH]nnc23)C1]

(3R)-1-[3-[(4-Methoxyphenyl)methyl]-5-morpholino-triazolo[4,5-d]pyrimidin-7-yl]-3-methyl-pyrrolidin-3-ol (0.45 g, 1 mmol) in TFA (3.87 mL) was heated to 80° C. for overnight and concentrated. The intermediately built ester was cleaved by NaOH (1M) and extracted with ethyl acetate. The combined organic layers were evaporated. The crude product was used in the consecutive step without further purification. MS(m/e): 306.2 (MH$^+$).

c) (3S)-1-[3-[(2-Chlorophenyl)methyl]-5-(2,2,2-trifluoroethoxy)triazolo[4,5-d]pyrimidin-7-yl]pyrrolidin-3-ol In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from (3S)-1-[5-(2,2,2-trifluoroethoxy)-3H-triazolo[4,5-d]pyrimidin-7-yl]pyrrolidin-3-ol and 1-(bromomethyl)-2-chlorobenzene. MS(m/e): 429.4 (MH$^+$).

Example 61

(3S)-1-[5-(2,2,2-Trifluoroethoxy)-3-[[2-(trifluoromethyl)phenyl]methyl]triazolo[4,5-d]pyrimidin-7-yl]pyrrolidin-3-ol

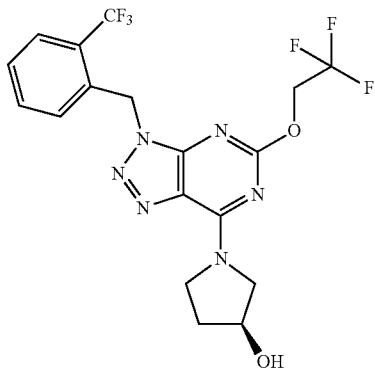 [SMILES: O[C@H]1CCN(c2nc(OCC(F)(F)F)nc3c2nnn3Cc2ccccc2C(F)(F)F)C1]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from (3S)-1-[5-(2,2,2-trifluoroethoxy)-3H-triazolo[4,5-d]pyrimidin-7-yl]pyrrolidin-3-ol and 1-(bromomethyl)-2-(trifluoromethyl)benzene. MS(m/e): 463.4 (MH$^+$).

Example 62

(3S)-1-[3-[(2-Chlorophenyl)methyl]-5-propan-2-yloxytriazolo[4,5-d]pyrimidin-7-yl]pyrrolidin-3-ol

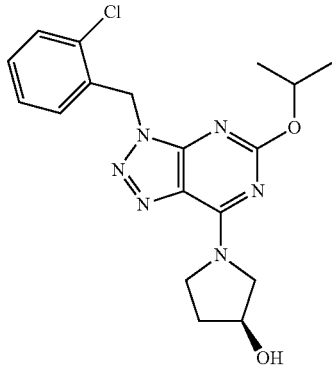 [SMILES: CC(C)Oc1nc(N2CC[C@H](O)C2)c2nnn(Cc3ccccc3Cl)c2n1]

a) (3S)-1-[5-Isopropoxy-3-[(4-methoxyphenyl)methyl]triazolo[4,5-d]pyrimidin-7-yl]pyrrolidin-3-ol

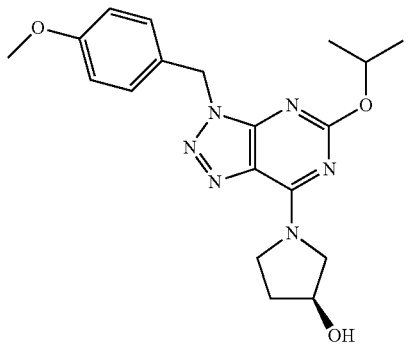 [SMILES: COc1ccc(Cn2nnc3c(N4CC[C@H](O)C4)nc(OC(C)C)nc32)cc1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from (3S)-1-[5-chloro-3-[(4-methoxyphenyl)methyl]triazolo[4,5-d]pyrimidin-7-yl]pyrrolidin-3-ol (example 19, step b) and propan-2-ol. MS(m/e): 385.4 (MH$^+$).

b) [(3S)-1-(5-Isopropoxy-3H-triazolo[4,5-d]pyrimidin-7-yl)pyrrolidin-3-yl]2,2,2-trifluoroacetate

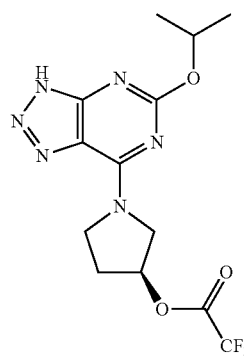

(3S)-1-[5-Isopropoxy-3-[(4-methoxyphenyl)methyl]triazolo[4,5-d]pyrimidin-7-yl]pyrrolidin-3-ol in TFA was heated to 70° C. for overnight and evaporated. The crude product was used in the consecutive step without further purification.

c) (3S)-1-[3-[(2-Chlorophenyl)methyl]-5-propan-2-yloxytriazolo[4,5-d]pyrimidin-7-yl]pyrrolidin-3-ol In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from [(3S)-1-(5-isopropoxy-3H-triazolo[4,5-d]pyrimidin-7-yl)pyrrolidin-3-yl]2,2,2-trifluoroacetate and 1-(bromomethyl)-2-chlorobenzene. MS(m/e): 389.3 (MH$^+$).

Example 63

(3S)-1-[3-[(2-Methylsulfonylphenyl)methyl]-5-propan-2-yloxytriazolo[4,5-d]pyrimidin-7-yl]pyrrolidin-3-ol

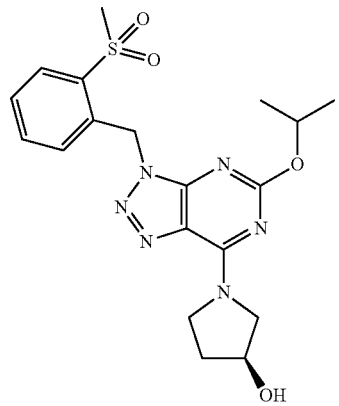 [SMILES: CC(C)Oc1nc(N2CC[C@H](O)C2)c2nnn(Cc3ccccc3S(C)(=O)=O)c2n1]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from [(3S)-1-(5-isopropoxy-3H-triazolo[4,5-d]pyrimidin-7-yl)pyrrolidin-3-yl]2,2,2-trifluoroacetate and 1-(bromomethyl)-2-(methylsulfonyl)benzene. MS(m/e): 433.3 (MH$^+$).

Example 64

(3S)-1-[3-[(1-Methyltetrazol-5-yl)methyl]-5-propan-2-yloxytriazolo[4,5-d]pyrimidin-7-yl]pyrrolidin-3-ol

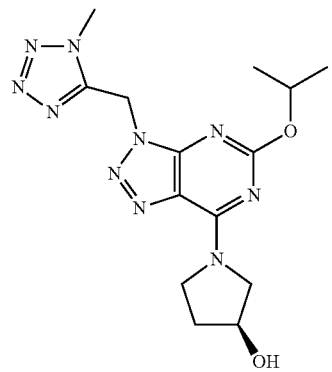 [SMILES: CC(C)Oc1nc(N2CC[C@H](O)C2)c2nnn(Cc3nnnn3C)c2n1]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from [(3S)-1-(5-isopropoxy-3H-triazolo[4,5-d]pyrimidin-7-yl)pyrrolidin-3-yl]2,2,2-trifluoroacetate and 5-(chloromethyl)-1-methyl-1H-tetrazole. MS(m/e): 361.3 (MH$^+$).

Example 65

7-(3,3-Difluoropyrrolidin-1-yl)-5-(2,2-dimethyl-propoxy)-3-[(1-methyltetrazol-5-yl)methyl]triazolo[4,5-d]pyrimidine

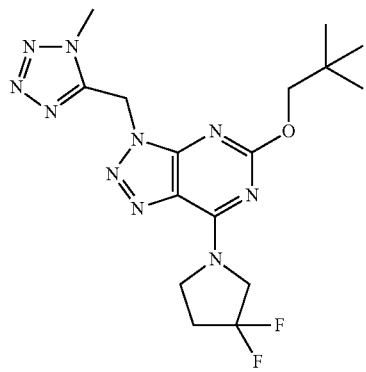 [SMILES: Cn1nnnc1Cn1nnc2c(N3CCC(F)(F)C3)nc(OCC(C)(C)C)nc21]

a) 7-(3,3-Difluoropyrrolidin-1-yl)-5-(2,2-dimethyl-propoxy)-3-[(4-methoxyphenyl)methyl]triazolo[4,5-d]pyrimidine

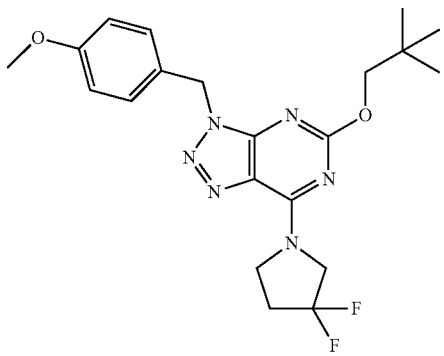 [SMILES: COc1ccc(Cn2nnc3c(N4CCC(F)(F)C4)nc(OCC(C)(C)C)nc32)cc1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-7-(3,3-difluoropyrrolidin-1-yl)-3-[(4-methoxyphenyl)methyl]triazolo[4,5-d]pyrimidine (example 20, step a) and 2,2-dimethylpropan-1-ol with the use of Cs$_2$CO$_3$ instead of NaH. MS(m/e): 433.2 (MH$^+$).

b) 7-(3,3-Difluoropyrrolidin-1-yl)-5-(2,2-dimethyl-propoxy)-3H-triazolo[4,5-d]pyrimidine

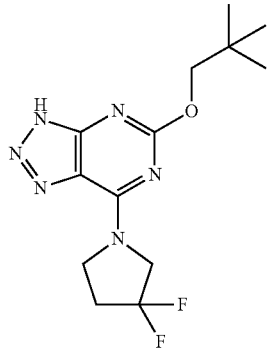 [SMILES: CC(C)(C)COc1nc(N2CCC(F)(F)C2)c2nn[nH]c2n1]

7-(3,3-Difluoropyrrolidin-1-yl)-5-(2,2-dimethyl-propoxy)-3-[(4-methoxyphenyl)methyl]triazolo[4,5-d]pyrimidine in TFA was heated to 80° C. for 3 h and evaporated. The crude product was used in the consecutive step without further purification. MS(m/e): 313.3 (MH$^+$).

c) 7-(3,3-Difluoropyrrolidin-1-yl)-5-(2,2-dimethyl-propoxy)-3-[(1-methyltetrazol-5-yl)methyl]triazolo[4,5-d]pyrimidine In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from 7-(3,3-difluoropyrrolidin-1-yl)-5-(2,2-dimethylpropoxy)-3H-triazolo[4,5-d]pyrimidine and 5-(chloromethyl)-1-methyl-1H-tetrazole. MS(m/e): 409.4 (MH$^+$).

Example 66

7-(3,3-Difluoropyrrolidin-1-yl)-5-(2,2-dimethyl-propoxy)-3-[(2-methyl sulfonylphenyl) methyl]triazolo[4,5-d]pyrimidine

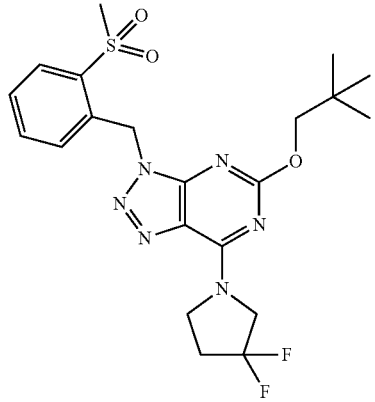 [SMILES: CC(C)(C)COc1nc(N2CCC(F)(F)C2)c2nnn(Cc3ccccc3S(C)(=O)=O)c2n1]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from 7-(3,3-difluoropyrrolidin-1-yl)-5-(2,2-dimethylpropoxy)-3H-triazolo[4,5-d]pyrimidine and 1-(bromomethyl)-2-(methylsulfonyl)benzene. MS(m/e): 481.4 (MH$^+$).

Example 67

3-[[7-(3,3-Difluoropyrrolidin-1-yl)-5-(2,2-dimethyl-propoxy)triazolo[4,5-d]pyrimidin-3-yl]methyl]-4-methyl-1,2,5-oxadiazole

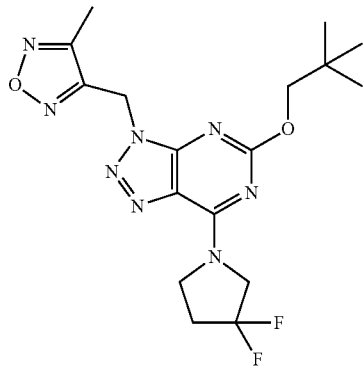 [SMILES: Cc1nonc1Cn1nnc2c(N3CCC(F)(F)C3)nc(OCC(C)(C)C)nc21]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from 7-(3,3-difluoropyrrolidin-1-yl)-5-(2,2-dimethylpropoxy)-3H-triazolo[4,5-d]pyrimidine and 3-(chloromethyl)-4-methyl-1,2,5-oxadiazole. MS(m/e): 409.4 (MH⁺).

Example 68

7-(3,3-Difluoropyrrolidin-1-yl)-3-[[2-(trifluoromethyl)phenyl]methyl]-5-[(2S)-1,1,1-trifluoropropan-2-yl]oxytriazolo[4,5-d]pyrimidine

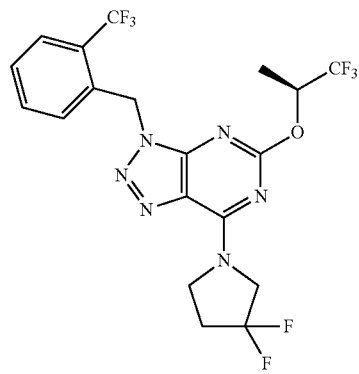

a) 7-(3,3-Difluoropyrrolidin-1-yl)-3-[(4-methoxyphenyl)methyl]-5-[(1 S)-2,2,2-trifluoro-1-methyl-ethoxy]triazolo[4,5-d]pyrimidine

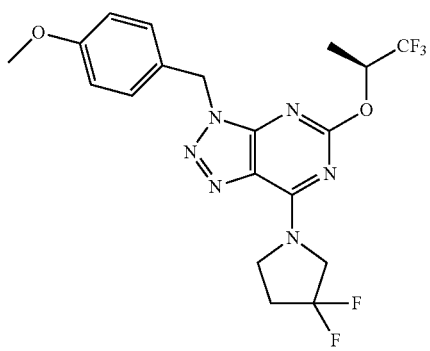 [SMILES: COc1ccc(Cn2nnc3c(N4CCC(F)(F)C4)nc(O[C@@H](C)C(F)(F)F)nc32)cc1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from 5-chloro-7-(3,3-difluoropyrrolidin-1-yl)-3-[(4-methoxyphenyl)methyl]triazolo[4,5-d]pyrimidine (example 20, step a) and (S)-1,1,1-trifluoropropan-2-ol with the use of Cs₂CO₃ instead of NaH. MS(m/e): 459.4 (MH⁺).

b) 7-(3,3-Difluoropyrrolidin-1-yl)-5-[(1 S)-2,2,2-trifluoro-1-methyl-ethoxy]-3H-triazolo[4,5-d]pyrimidine

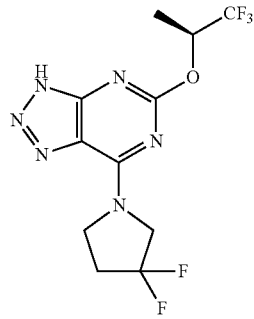 [SMILES: C[C@H](Oc1nc(N2CCC(F)(F)C2)c2nn[nH]c2n1)C(F)(F)F]

7-(3,3-Difluoropyrrolidin-1-yl)-3-[(4-methoxyphenyl)methyl]-5-[(1 S)-2,2,2-trifluoro-1-methyl-ethoxy]triazolo[4,5-d]pyrimidine in TFA was heated to 80° C. for 2 h and evaporated. The mixture was poured into NaHCO₃ aq. (1M) and extracted with ethyl acetate. The combined organic layers were filtered and evaporated. The crude product was used in the consecutive step without further purification.

c) 7-(3,3-Difluoropyrrolidin-1-yl)-3-[[2-(trifluoromethyl)phenyl]methyl]-5-[(2S)-1,1,1-trifluoropropan-2-yl]oxytriazolo[4,5-d]pyrimidine In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from 7-(3,3-difluoropyrrolidin-1-yl)-5-[(1 S)-2,2,2-trifluoro-1-methyl-ethoxy]-3H-triazolo[4,5-d]pyrimidine and 1-(bromomethyl)-2-(trifluoromethyl)benzene. MS(m/e): 497.4 (MH⁺).

Example 69

7-(3,3-Difluoropyrrolidin-1-yl)-3-[(2-methyl sulfonylphenyl)methyl]-5-[(2S)-1,1,1-trifluoropropan-2-yl]oxytriazolo[4,5-d]pyrimidine

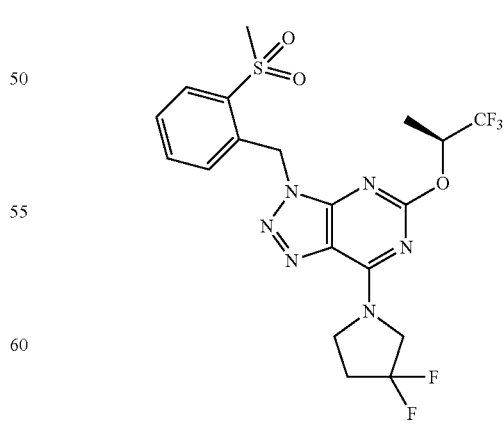

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from 7-(3,3-difluoropyrrolidin-1-yl)-5-[(1 S)-2,2,2-trifluoro-1-methylethoxy]-3H-triazolo[4,5-d]pyrimidine and 1-(bromomethyl)-2-(methylsulfonyl)benzene. MS(m/e): 507.4 (MH⁺).

Example 70

3-[(3-Chloropyridin-2-yl)methyl]-7-(3,3-difluoropyrrolidin-1-yl)-5-[(2S)-1,1,1-trifluoropropan-2-yl]oxytriazolo[4,5-d]pyrimidine

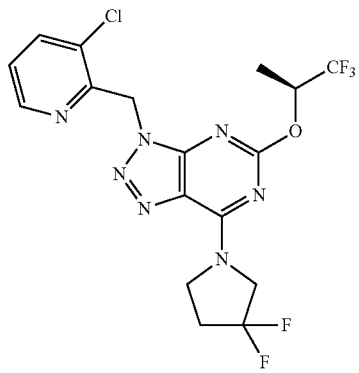 [SMILES: C[C@H](Oc1nc(N2CCC(F)(F)C2)c2nnn(Cc3ncccc3Cl)c2n1)C(F)(F)F]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from 7-(3,3-difluoropyrrolidin-1-yl)-5-[(1 S)-2,2,2-trifluoro-1-methylethoxy]-3H-triazolo[4,5-d]pyrimidine and 3-chloro-2-(chloromethyl)pyridine. MS(m/e): 464.3 (MH⁺).

Example 71

2-[[7-(3,3-Difluoropyrrolidin-1-yl)-5-[(2S)-1,1,1-trifluoropropan-2-yl]oxytriazolo[4,5-d]pyrimidin-3-yl]methyl]-5-methyl-1,3,4-oxadiazole

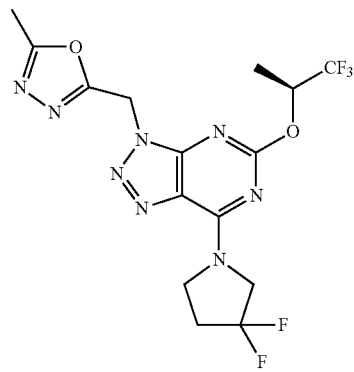 [SMILES: Cc1nnc(Cn2nnc3c(N4CCC(F)(F)C4)nc(O[C@@H](C)C(F)(F)F)nc32)o1]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from 7-(3,3-difluoropyrrolidin-1-yl)-5-[(1 S)-2,2,2-trifluoro-1-methylethoxy]-3H-triazolo[4,5-d]pyrimidine and 2-(chloromethyl)-5-methyl-1,3,4-oxadiazole. MS(m/e): 435.4 (MH⁺).

Example 72

5-[[7-(3,3-Difluoropyrrolidin-1-yl)-5-[(2S)-1,1,1-trifluoropropan-2-yl]oxytriazolo[4,5-d]pyrimidin-3-yl]methyl]-3-methyl-1,2,4-oxadiazole

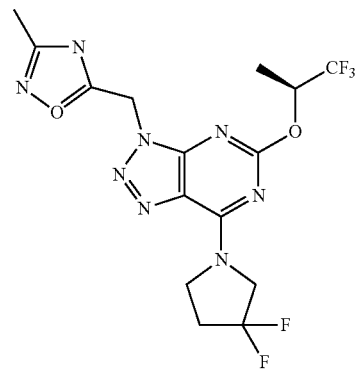

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from 7-(3,3-difluoropyrrolidin-1-yl)-5-[(1S)-2,2,2-trifluoro-1-methylethoxy]-3H-triazolo[4,5-d]pyrimidine and 5-(chloromethyl)-3-methyl-1,2,4-oxadiazole. MS(m/e): 435.4 (MH⁺).

Example 73

7-(3,3-Difluoropyrrolidin-1-yl)-3-[(1-methyltetrazol-5-yl)methyl]-5-[(2S)-1,1,1-trifluoropropan-2-yl]oxytriazolo[4,5-d]pyrimidine

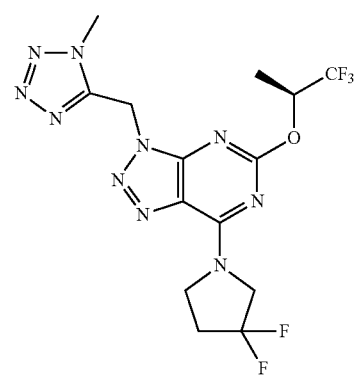 [SMILES: C[C@H](Oc1nc(N2CCC(F)(F)C2)c2nnn(Cc3nnnn3C)c2n1)C(F)(F)F]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from 7-(3,3-difluoropyrrolidin-1-yl)-5-[(1S)-2,2,2-trifluoro-1-methylethoxy]-3H-triazolo[4,5-d]pyrimidine and 5-(chloromethyl)-1-methyl-1H-tetrazole. MS(m/e): 435.4 (MH⁺).

Example 74

3-[[7-(3,3-Difluoropyrrolidin-1-yl)-5-[(2S)-1,1,1-trifluoropropan-2-yl]oxytriazolo[4,5-d]pyrimidin-3-yl]methyl]-4-methyl-1,2,5-oxadiazole

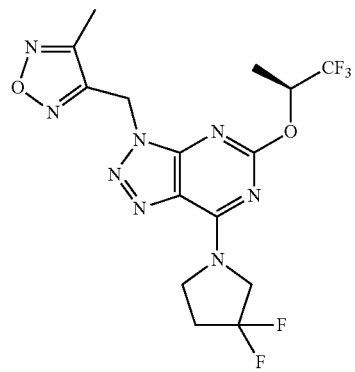 [SMILES: Cc1nonc1Cn1nnc2c(N3CCC(F)(F)C3)nc(O[C@@H](C)C(F)(F)F)nc21]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from 7-(3,3-difluoropyrrolidin-1-yl)-5-[(1 S)-2,2,2-trifluoro-1-methylethoxy]-3H-triazolo[4,5-d]pyrimidine and 3-(bromomethyl)-4-methyl-1,2,5-oxadiazole. MS(m/e): 435.4 (MH+).

Example 75

7-(3,3-Difluoropyrrolidin-1-yl)-5-[(2S)-1,1,1-trifluoropropan-2-yl]oxy-3-(3,3,3-trifluoropropyl)triazolo[4,5-d]pyrimidine

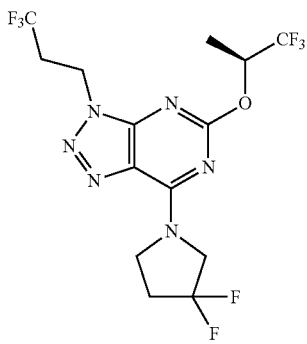 [SMILES: C[C@H](Oc1nc(N2CCC(F)(F)C2)c2nnn(CCC(F)(F)F)c2n1)C(F)(F)F]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from 7-(3,3-difluoropyrrolidin-1-yl)-5-[(1 S)-2,2,2-trifluoro-1-methylethoxy]-3H-triazolo[4,5-d]pyrimidine and 3-bromo-1,1,1-trifluoropropane. MS(m/e): 435.4 (MH+).

Example 76

3-[(1-Cyclopropyltetrazol-5-yl)methyl]-7-(3,3-difluoropyrrolidin-1-yl)-5-[(2S)-1,1,1-trifluoropropan-2-yl]oxytriazolo[4,5-d]pyrimidine

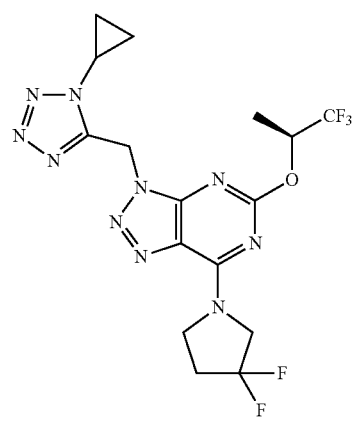 [SMILES: C[C@H](Oc1nc(N2CCC(F)(F)C2)c2nnn(Cc3nnnn3C3CC3)c2n1)C(F)(F)F]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from 7-(3,3-difluoropyrrolidin-1-yl)-5-[(1S)-2,2,2-trifluoro-1-methylethoxy]-3H-triazolo[4,5-d]pyrimidine and 5-(chloromethyl)-1-cyclopropyl-1H-tetrazole. MS(m/e): 461.4 (MH+).

Example 77

N-[(3S)-1-[3-[(2-Chlorophenyl)methyl]-5-(2,2-dimethylpropoxy)triazolo[4,5-d]pyrimidin-7-yl]pyrrolidin-3-yl]acetamide

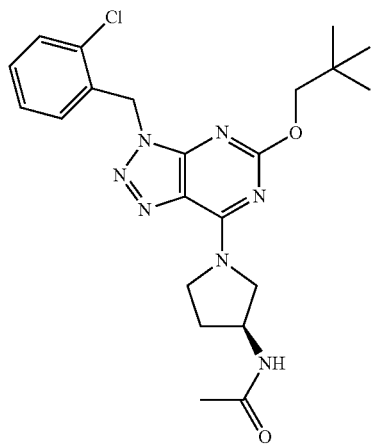 [SMILES: CC(=O)N[C@H]1CCN(c2nc(OCC(C)(C)C)nc3c2nnn3Cc2ccccc2Cl)C1]

a) N-[(3S)-1-[5-(2,2-Dimethylpropoxy)-3-[(4-methoxyphenyl)methyl]triazolo[4,5-d]pyrimidin-7-yl]pyrrolidin-3-yl]acetamide

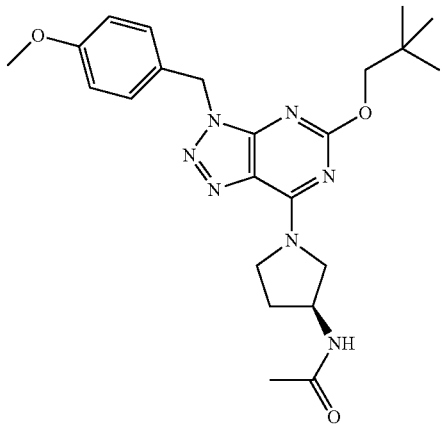 [SMILES: COc1ccc(Cn2nnc3c(N4CC[C@H](NC(C)=O)C4)nc(OCC(C)(C)C)nc32)cc1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from N-[(3S)-1-[5-chloro-3-[(4-methoxyphenyl)methyl]triazolo[4,5-d]pyrimidin-7-yl]pyrrolidin-3-yl]acetamide (example 21, step a) and 2,2-dimethylpropan-1-ol. MS(m/e): 254.4 (MH$^+$).

b) N-[(3S)-1-[5-(2,2-Dimethylpropoxy)-3H-triazolo[4,5-d]pyrimidin-7-yl]pyrrolidin-3-yl]acetamide

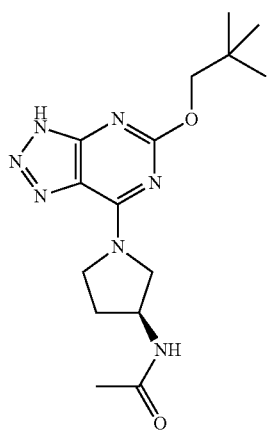 [SMILES: CC(=O)N[C@H]1CCN(c2nc(OCC(C)(C)C)nc3[nH]nnc23)C1]

N-[(3S)-1-[5-(2,2-Dimethylpropoxy)-3-[(4-methoxyphenyl)methyl]triazolo[4,5-d]pyrimidin-7-yl]pyrrolidin-3-yl]acetamide was hydrogenated over Pd/C in methanol to yield the title compound which was used in the consecutive step without further purification.

c) N-[(3S)-1-[3-[(2-Chlorophenyl)methyl]-5-(2,2-dimethylpropoxy)triazolo[4,5-d]pyrimidin-7-yl]pyrrolidin-3-yl]acetamide In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from N-[(3S)-1-[5-(2,2-dimethylpropoxy)-3H-triazolo[4,5-d]pyrimidin-7-yl]pyrrolidin-3-yl]acetamide and 1-(bromomethyl)-2-chlorobenzene. MS(m/e): 458.4 (MH$^+$).

Example 78

N-[(3S)-1-[3-[(3-Chloropyridin-2-yl)methyl]-5-(2,2-dimethylpropoxy)triazolo[4,5-d]pyrimidin-7-yl]pyrrolidin-3-yl]acetamide

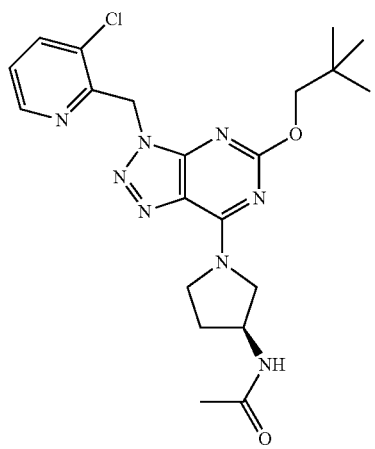 [SMILES: CC(=O)N[C@H]1CCN(c2nc(OCC(C)(C)C)nc3c2nnn3Cc2ncccc2Cl)C1]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from N-[(3S)-1-[5-(2,2-dimethylpropoxy)-3H-triazolo[4,5-d]pyrimidin-7-yl]pyrrolidin-3-yl]acetamide and 3-chloro-2-(chloromethyl)pyridine. MS(m/e): 459.4 (MH$^+$).

Example 79

N-[(3S)-1-[5-(2,2-Dimethylpropoxy)-3-[(4-methyl-1,2,5-oxadiazol-3-yl)methyl]triazolo[4,5-d]pyrimidin-7-yl]pyrrolidin-3-yl]acetamide

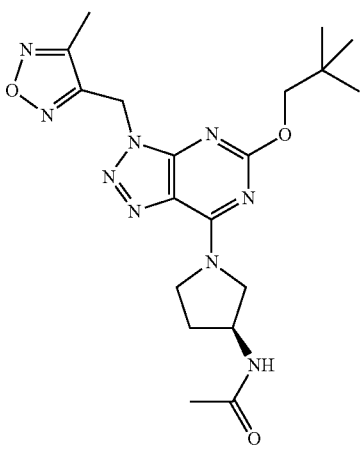 [SMILES: CC(=O)N[C@H]1CCN(c2nc(OCC(C)(C)C)nc3c2nnn3Cc2nonc2C)C1]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from N-[(3S)-1-[5-(2,2-dimethylpropoxy)-3H-triazolo[4,5-d]pyrimidin-7-yl]pyrrolidin-3-yl]acetamide and 3-(bromomethyl)-4-methyl-1,2,5-oxadiazole. MS(m/e): 430.4 (MH⁺).

Example 80

N-[(3S)-1-[3-[(2-Chlorophenyl)methyl]-5-[(2S)-1,1,1-trifluoropropan-2-yl]oxytriazolo [4,5-d]pyrimidin-7-yl]pyrrolidin-3-yl]acetamide

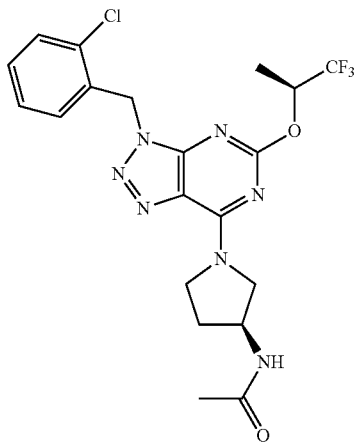 [SMILES: CC(=O)N[C@H]1CCN(c2nc(O[C@@H](C)C(F)(F)F)nc3c2nnn3Cc2ccccc2Cl)C1]

a) N-[(3S)-1-[3-[(4-Methoxyphenyl)methyl]-5-[(1 S)-2,2,2-trifluoro-1-methyl-ethoxy]triazolo[4,5-d]pyrimidin-7-yl]pyrrolidin-3-yl]acetamide

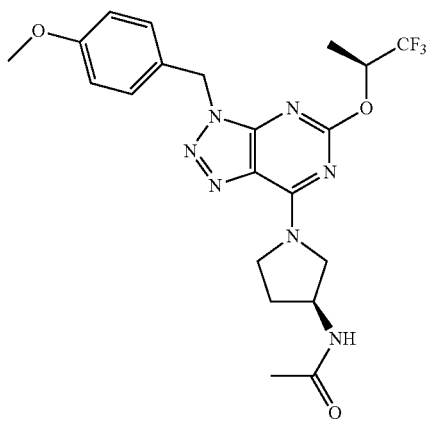 [SMILES: COc1ccc(Cn2nnc3c(N4CC[C@H](NC(C)=O)C4)nc(O[C@@H](C)C(F)(F)F)nc32)cc1]

In analogy to the procedure described for the synthesis of 3-[(2-chlorophenyl)methyl]-7-(3,3-difluoropyrrolidin-1-yl)-5-(2,2,2-trifluoroethoxy)triazolo[4,5-d]pyrimidine (example 40) the title compound was prepared from N-[(3S)-1-[5-chloro-3-[(4-methoxyphenyl)methyl]triazolo[4,5-d]pyrimidin-7-yl]pyrrolidin-3-yl]acetamide (example 21, step a) and (S)-1,1,1-trifluoropropan-2-ol. MS(m/e): 480.5 (MH⁺).

b) N-[(3S)-1-[5-[(1S)-2,2,2-Trifluoro-1-methyl-ethoxy]-3H-triazolo[4,5-d]pyrimidin-7-yl]pyrrolidin-3-yl]acetamide

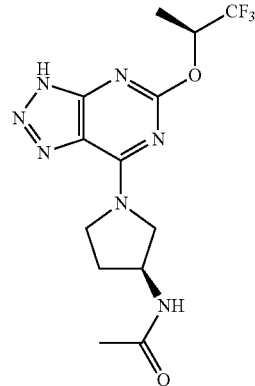 [SMILES: CC(=O)N[C@H]1CCN(c2nc(O[C@@H](C)C(F)(F)F)nc3[nH]nnc23)C1]

N-[(3S)-1-[3-[(4-Methoxyphenyl)methyl]-5-[(1 S)-2,2,2-trifluoro-1-methyl-ethoxy]triazolo[4,5-d]pyrimidin-7-yl]pyrrolidin-3-yl]acetamide was hydrogenated over Pd/C in methanol to yield the title compound which was used in the consecutive step without further purification.

c) N-[(3S)-1-[3-[(2-Chlorophenyl)methyl]-5-[(2 S)-1,1,1-trifluoropropan-2-yl]oxytriazolo [4,5-d] pyrimidin-7-yl]pyrrolidin-3-yl]acetamide In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from N-[(3S)-1-[5-[(1S)-2,2,2-trifluoro-1-methyl-ethoxy]-3H-triazolo[4,5-d]pyrimidin-7-yl]pyrrolidin-3-yl]acetamide and 1-(bromomethyl)-2-chlorobenzene. MS(m/e): 484.4 (MH⁺).

Example 81

N-[(3S)-1-[3-[[2-(Trifluoromethyl)phenyl]methyl]-5-[(2S)-1,1,1-trifluoropropan-2-yl]oxytriazolo[4,5-d]pyrimidin-7-yl]pyrrolidin-3-yl]acetamide

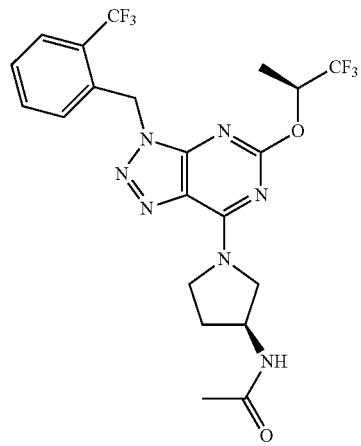 [SMILES: CC(=O)N[C@H]1CCN(c2nc(O[C@@H](C)C(F)(F)F)nc3c2nnn3Cc2ccccc2C(F)(F)F)C1]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from N-[(3S)-1-[5-[(1S)-2,2,2-trifluoro-1-methyl-ethoxy]-3H-triazolo[4,5-d]pyrimidin-7-yl]pyrrolidin-3-yl]acetamide and 1-(bromomethyl)-2-(trifluoromethyl)benzene. MS(m/e): 528.5 (MH+).

Example 82

3-[(2-Chlorophenyl)methyl]-7-(3,3-difluoropyrrolidin-1-yl)-5-ethylsulfanyltriazolo [4,5-d]pyrimidine

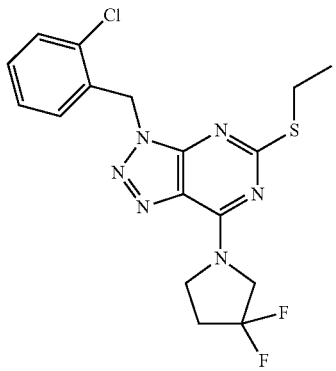 [SMILES: CCSc1nc(N2CCC(F)(F)C2)c2nnn(Cc3ccccc3Cl)c2n1]

A mixture of 5-chloro-3-[(2-chlorophenyl)methyl]-7-(3,3-difluoropyrrolidin-1-yl)triazolo[4,5-d]pyrimidine (example 8, step a) (77 mg, 0.2 mmol), DIPEA (90.5 mg, 0.7 mmol) and ethanethiol (62.5 mg, 1 mmol) in DMF (3 mL) was stirred at 110° C. overnight. The mixture was concentrated and the residue was subjected to purification by preparative HPLC on reversed phase eluting with a gradient formed from acetonitrile, water and formic acid. The product containing fractions were evaporated to yield 62.3 mg (50%) of the title compound. MS(m/e): 411.2 (MH+).

Example 83

3-[(2-Chlorophenyl)methyl]-7-(3,3-difluoropyrrolidin-1-yl)-5-(2,2,2-trifluoroethyl sulfanyl)triazolo[4,5-d]pyrimidine

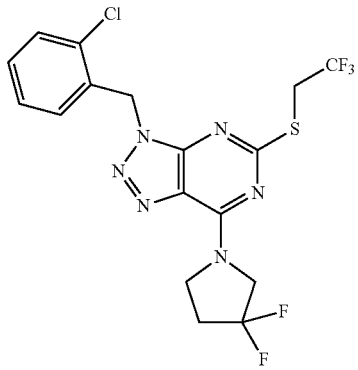 [SMILES: FC(F)(F)CSc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-ethylsulfanyltriazolo[4,5-d]pyrimidine (example 82) the title compound was prepared from 5-chloro-3-[(2-chlorophenyl)methyl]-7-(3,3-difluoropyrrolidin-1-yl)triazolo[4,5-d]pyrimidine (example 8, step a) and 2,2,2-trifluoroethanethiol. MS(m/e): 465.2 (MH+).

Example 84

3-[(2-Chlorophenyl)methyl]-7-(3,3-difluoropyrrolidin-1-yl)-5-propan-2-ylsulfanyltriazolo[4,5-d]pyrimidine

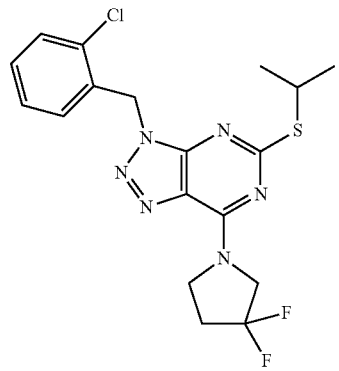 [SMILES: CC(C)Sc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-ethylsulfanyltriazolo[4,5-d]pyrimidine (example 82) the title compound was prepared from 5-chloro-3-[(2-chlorophenyl)methyl]-7-(3,3-difluoropyrrolidin-1-yl)triazolo[4,5-d]pyrimidine (example 8, step a) and propane-2-thiol. MS(m/e): 425.3 (MH+).

Example 85

5-tert-Butylsulfanyl-3-[(2-chlorophenyl)methyl]-7-(3,3-difluoropyrrolidin-1-yl)triazolo[4,5-d]pyrimidine

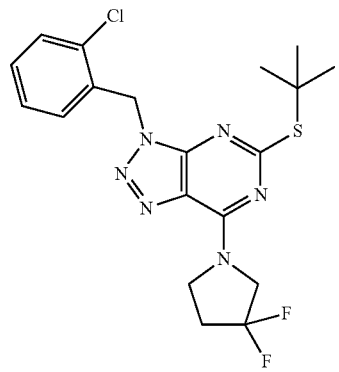 [SMILES: CC(C)(C)Sc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-ethylsulfanyltriazolo[4,5-d]pyrimidine (example 82) the title compound was prepared from 5-chloro-3-[(2-chlorophenyl)methyl]-7-(3,3-difluoropyrrolidin-1-yl)triazolo[4,5-d]pyrimidine (example 8, step a) and 2-methylpropane-2-thiol. MS(m/e): 439.3 (MH⁺).

Example 86

3-[(2-Chlorophenyl)methyl]-7-(3,3-difluoropyrrolidin-1-yl)-5-ethylsulfonyltriazolo [4,5-d]pyrimidine

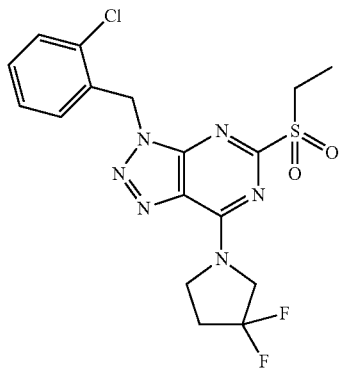 [SMILES: CCS(=O)(=O)c1nc(N2CCC(F)(F)C2)c2nnn(Cc3ccccc3Cl)c2n1]

A mixture of 3-[(2-chlorophenyl)methyl]-7-(3,3-difluoropyrrolidin-1-yl)-5-ethylsulfanyltriazolo[4,5-d]pyrimidine (example 82) (79.4 mg, 0.2 mmol) and 3-chlorobenzoperoxoic acid (80 mg, 0.46 mmol) in DCM (2 mL) was stirred at room temperature for 4 h. The mixture was evaporated and the residue was subjected to purification by preparative HPLC on reversed phase eluting with a gradient formed from acetonitrile, water and formic acid. The product containing fractions were evaporated to yield 26 mg (29%) of the title compound. MS(m/e): 443.2 (MH⁺).

Example 87

5-Benzylsulfonyl-3-[(2-chlorophenyl)methyl]-7-(3,3-difluoropyrrolidin-1-yl)triazolo [4,5-d]pyrimidine

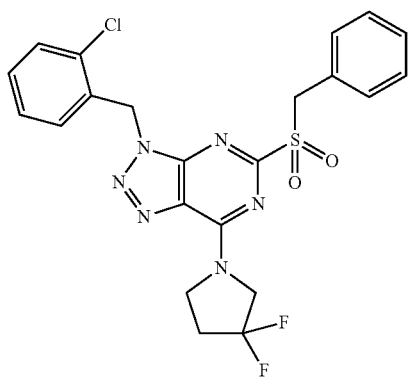 [SMILES: O=S(=O)(Cc1ccccc1)c1nc(N2CCC(F)(F)C2)c2nnn(Cc3ccccc3Cl)c2n1]

a) 5-Benzylsulfanyl-3-[(2-chlorophenyl)methyl]-7-(3,3-difluoropyrrolidin-1-yl)triazolo[4,5-d]pyrimidine

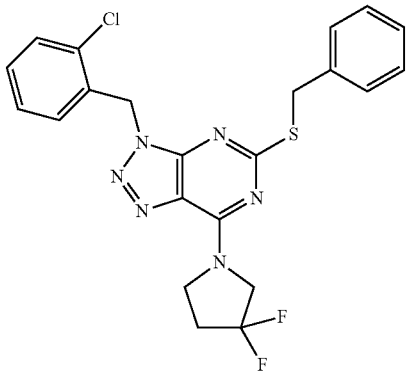 [SMILES: FC1(F)CCN(c2nc(SCc3ccccc3)nc3c2nnn3Cc2ccccc2Cl)C1]

In analogy to the procedure described for the synthesis of 3-[(2-chlorophenyl)methyl]-7-(3,3-difluoropyrrolidin-1-yl)-5-ethylsulfanyltriazolo[4,5-d]pyrimidine (example 82) the title compound was prepared from 5-chloro-3-[(2-chlorophenyl)methyl]-7-(3,3-difluoropyrrolidin-1-yl)triazolo[4,5-d]pyrimidine (example 8, step a) and phenylmethanethiol. MS(m/e): 473.2 (MH⁺).

b) 5-Benzylsulfonyl-3-[(2-chlorophenyl)methyl]-7-(3,3-difluoropyrrolidin-1-yl)triazolo[4,5-d]pyrimidine In analogy to the procedure described for the synthesis of 3-[(2-chlorophenyl)methyl]-7-(3,3-difluoropyrrolidin-1-yl)-5-ethylsulfonyltriazolo[4,5-d]pyrimidine (example 86) the title compound was prepared from 5-benzylsulfanyl-3-[(2-chlorophenyl)methyl]-7-(3,3-difluoropyrrolidin-1-yl)triazolo[4,5-d]pyrimidine through oxidation with MCPBA. MS(m/e): 505.2 (MH⁺).

Example 88

3-[(2-Chlorophenyl)methyl]-7-(3,3-difluoropyrrolidin-1-yl)-5-propan-2-ylsulfonyltriazolo[4,5-d]pyrimidine

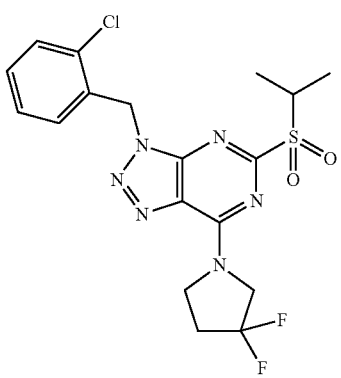 [SMILES: CC(C)S(=O)(=O)c1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-

5-ethylsulfonyltriazolo[4,5-d]pyrimidine (example 86) the title compound was prepared from 3-[(2-chlorophenyl)methyl]-7-(3,3-difluoropyrrolidin-1-yl)-5-propan-2-ylsulfanyltriazolo[4,5-d]pyrimidine through oxidation with MCPBA. MS(m/e): 457.3 (MH+).

Example 89

2-[3-[(2-Chlorophenyl)methyl]-7-(3,3-difluoropyrrolidin-1-yl)triazolo[4,5-d]pyrimidin-5-yl]sulfanylethanol

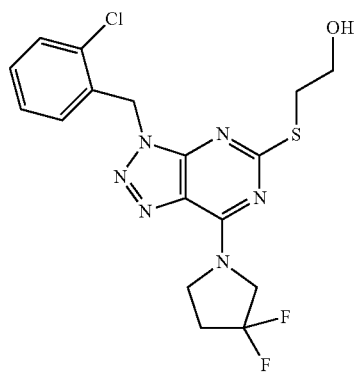 [SMILES: OCCSc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-ethylsulfanyltriazolo[4,5-d]pyrimidine (example 82) the title compound was prepared from 5-chloro-3-[(2-chlorophenyl)methyl]-7-(3,3-difluoropyrrolidin-1-yl)triazolo[4,5-d]pyrimidine (example 8, step a) and 2-mercaptoethanol. MS(m/e): 427.2 (MH+).

Example 90

1-[3-[(2-Chlorophenyl)methyl]-7-(3,3-difluoropyrrolidin-1-yl)triazolo[4,5-d]pyrimidin-5-yl]sulfanylpropan-2-ol

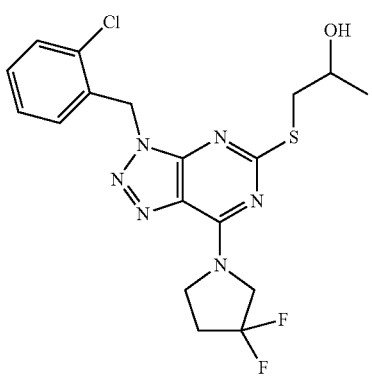 [SMILES: CC(O)CSc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-ethylsulfanyltriazolo[4,5-d]pyrimidine (example 82) the title compound was prepared from 5-chloro-3-[(2-chlorophenyl)methyl]-7-(3,3-difluoropyrrolidin-1-yl)triazolo[4,5-d]pyrimidine (example 8, step a) and 1-mercaptopropan-2-ol. MS(m/e): 441.2 (MH+).

Example 91

5-Butylsulfanyl-3-[(2-chlorophenyl)methyl]-7-(3,3-difluoropyrrolidin-1-yl)triazolo [4,5-d]pyrimidine

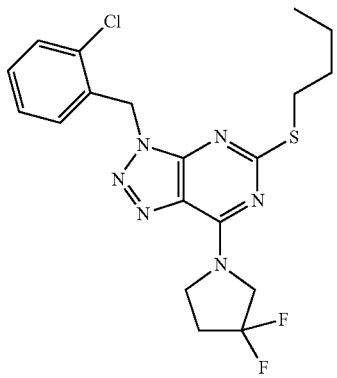 [SMILES: CCCCSc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-ethylsulfanyltriazolo[4,5-d]pyrimidine (example 82) the title compound was prepared from 5-chloro-3-[(2-chlorophenyl)methyl]-7-(3,3-difluoropyrrolidin-1-yl)triazolo[4,5-d]pyrimidine (example 8, step a) and butane-1-thiol at elevated temperature in DMF. MS(m/e): 439.2 (MH+).

Example 92

3-[(2-Chlorophenyl)methyl]-7-(3,3-difluoropyrrolidin-1-yl)-5-(2-methylpropylsulfanyl)triazolo[4,5-d]pyrimidine

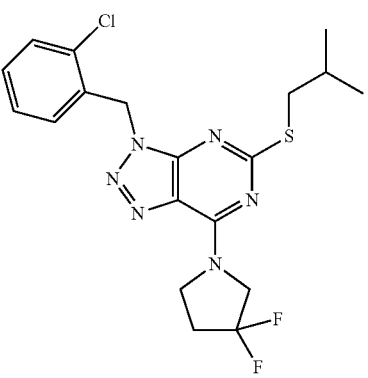 [SMILES: CC(C)CSc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-ethylsulfanyltriazolo[4,5-d]pyrimidine (example 82) the title compound was prepared from 5-chloro-3-[(2-chlorophenyl)methyl]-7-(3,3-difluoropyrrolidin-1-yl)triazolo[4,5-d]pyrimidine (example 8, step a) and 2-methylpropane-1-thiol at elevated temperature in DMF. MS(m/e): 439.2 (MH+).

Example 93

5-Butylsulfonyl-3-[(2-chlorophenyl)methyl]-7-(3,3-difluoropyrrolidin-1-yl)triazolo [4,5-d]pyrimidine

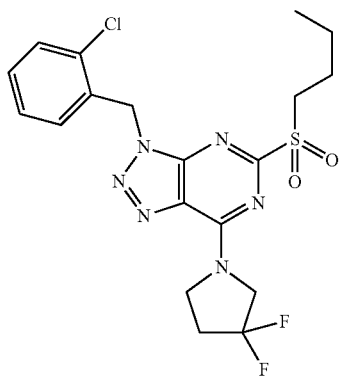 [SMILES: CCCCS(=O)(=O)c1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-ethylsulfonyltriazolo[4,5-d]pyrimidine (example 86) the title compound was prepared from 5-butylsulfanyl-3-[(2-chlorophenyl)methyl]-7-(3,3-difluoropyrrolidin-1-yl)triazolo[4,5-d]pyrimidine through oxidation with MCPBA. MS(m/e): 471.3 (MH$^+$).

Example 94

3-[(2-Chlorophenyl)methyl]-7-(3,3-difluoropyrrolidin-1-yl)-5-(2-methylpropylsulfonyl)triazolo[4,5-d]pyrimidine

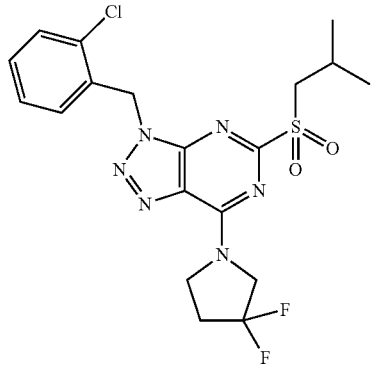 [SMILES: CC(C)CS(=O)(=O)c1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-ethylsulfonyltriazolo[4,5-d]pyrimidine (example 86) the title compound was prepared from 3-[(2-chlorophenyl)methyl]-7-(3,3-difluoropyrrolidin-1-yl)-5-(2-methylpropylsulfanyl)triazolo[4,5-d]pyrimidine through oxidation with MCPBA. MS(m/e): 471.3 (MH$^+$).

Example 95

1-[3-[(2-Chlorophenyl)methyl]-7-(3,3-difluoropyrrolidin-1-yl)triazolo[4,5-d]pyrimidin-5-yl]sulfonylpropan-2-ol

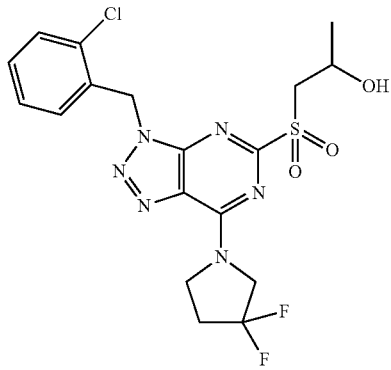 [SMILES: CC(O)CS(=O)(=O)c1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-ethylsulfonyltriazolo[4,5-d]pyrimidine (example 86) the title compound was prepared from 3-[(2-chlorophenyl)methyl]-7-(3,3-difluoropyrrolidin-1-yl)-5-(2-methylpropylsulfanyl)triazolo[4,5-d]pyrimidine through oxidation with MCPBA. MS(m/e): 473.2 (MH$^+$).

Example 96

3-[(2-Chlorophenyl)methyl]-7-(3,3-difluoropyrrolidin-1-yl)-5-(2-methoxyethylsulfonyl)triazolo[4,5-d]pyrimidine

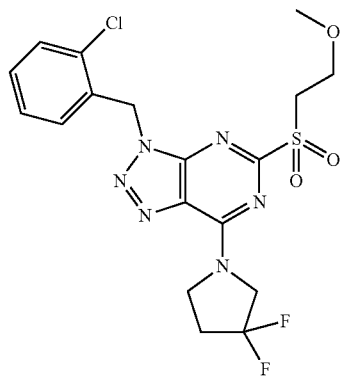 [SMILES: COCCS(=O)(=O)c1nc(N2CCC(F)(F)C2)c2nnn(Cc3ccccc3Cl)c2n1]

a) 3-[(2-Chlorophenyl)methyl]-7-(3,3-difluoropyrrolidin-1-yl)-5-(2-methoxyethylsulfanyl)triazolo[4,5-d]pyrimidine

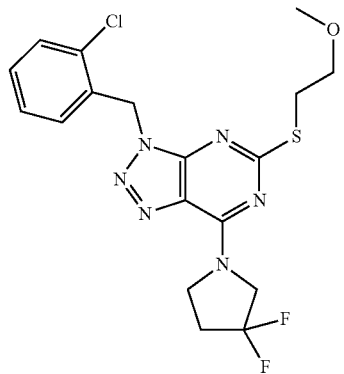 [SMILES: COCCSc1nc(N2CCC(F)(F)C2)c2nnn(Cc3ccccc3Cl)c2n1]

In analogy to the procedure described for the synthesis of 3-[(2-chlorophenyl)methyl]-7-(3,3-difluoropyrrolidin-1-yl)-5-ethylsulfanyltriazolo[4,5-d]pyrimidine (example 82) the title compound was prepared from 5-chloro-3-[(2-chlorophenyl)methyl]-7-(3,3-difluoropyrrolidin-1-yl)triazolo[4,5-d]pyrimidine (example 8, step a) and 2-methoxyethanethiol at elevated temperature in DMF. MS(m/e): 441.2 (MH⁺).

b) 3-[(2-Chlorophenyl)methyl]-7-(3,3-difluoropyrrolidin-1-yl)-5-(2-methoxyethylsulfonyl)triazolo[4,5-d]pyrimidine In analogy to the procedure described for the synthesis of 3-[(2-chlorophenyl)methyl]-7-(3,3-difluoropyrrolidin-1-yl)-5-ethylsulfonyltriazolo[4,5-d]pyrimidine (example 86) the title compound was prepared from 3-[(2-chlorophenyl)methyl]-7-(3,3-difluoropyrrolidin-1-yl)-5-(2-methoxyethylsulfanyl)triazolo[4,5-d]pyrimidine through oxidation with MCPBA. MS(m/e): 473.2 (MH⁺).

Example 97

N-[(3S)-1-[5-(tert-butylamino)-3-[(2-chlorophenyl)methyl]triazolo[4,5-d]pyrimidin-7-yl]pyrrolidin-3-yl]acetamide

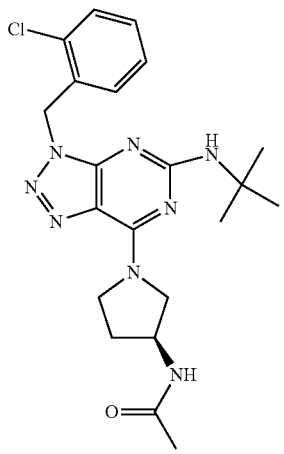 [SMILES: CC(=O)N[C@H]1CCN(c2nc(NC(C)(C)C)nc3c2nnn3Cc2ccccc2Cl)C1]

In analogy to the procedure described for the synthesis of N-tert-butyl-7-(3,3-difluoropyrrolidin-1-yl)-3-[[2-(trifluoromethyl)phenyl]methyl]triazolo[4,5-d]pyrimidin-5-amine (example 22) the title compound was prepared from N-[(3S)-1-[5-(tert-butylamino)-3H-triazolo[4,5-d]pyrimidin-7-yl]pyrrolidin-3-yl]acetamide and 1-(bromomethyl)-2-chlorobenzene. MS(m/e): 443.4 (MH⁺).

Example 98

Pharmacological Tests

The following tests were carried out in order to determine the activity of the compounds of formula I:

Radioligand Binding Assay

The affinity of the compounds of the invention for cannabinoid CB1 receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively Binding was performed in binding buffer (50 mM Tris, 5 mM MgCl2, 2.5 mM EDTA, and 0.5% (wt/vol) fatty acid free BSA, pH 7.4 for CB1 receptor and 50 mM Tris, 5 mM MgCl₂, 2.5 mM EGTA, and 0.1% (wt/vol) fatty acid free BSA, pH 7.4 for CB2 receptor) in a total volume of 0.2 ml for 1 h at 30° C. shaking. The reaction was terminated by rapid filtration through microfiltration plates coated with 0.5% polyethylenimine (UniFilter GF/B filter plate; Packard). Bound radioactivity was analyzed for Ki using nonlinear regression analysis (Activity Base, ID Business Solution, Limited), with the Kd values for [3H]CP55, 940 determined from saturation experiments. The compounds of formula (I) show an excellent affinity for the CB2 receptor with affinities below 10 μM, more particularly of 1 nM to 3 μM and most particularly of 1 nM to 100 nM.

cAMP Assay

CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1×HT supplement, with 10% fetal calf serum and incubated at 5% CO₂ and 37° C. in a humidified incubator. The growth medium was exchanged with Krebs Ringer Bicarbonate buffer with 1 mM IBMX and incubated at 30° C. for 30 min. Compounds were added to a final assay volume of 100 μl and incubated for 30 min at 30° C. Using the cAMP-Nano-TRF detection kit the assay (Roche Diagnostics) was stopped by the addition of 50 μl lysis reagent (Tris, NaCl, 1.5% Triton X100, 2.5% NP40, 10% NaN₃) and 50 μl detection solutions (20 μM mAb Alexa700-cAMP 1:1, and 48 μM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The FRET signal is calculated as follows: FRET=T730-Alexa730-P(T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 μM to 0.13 nM cAMP.

EC₅₀ values were determined using Activity Base analysis (ID Business Solution, Limited). The EC₅₀ values for a wide range of cannabinoid agonists generated from this assay were in agreement with the values published in the scientific literature.

The compounds of the invention are CB2 receptor agonists with EC₅₀ below 1 μM and selectivity versus CB1 in the corresponding assay of at least 10 fold. Particular compound of the invention are CB2 receptor agonists with EC₅₀ below 0.05 μM and selectivity versus CB1 in the corresponding assay of at least 500 fold.

For example, the following compounds showed the following human EC₅₀ values in the functional cAMP assay described above:

| Example | CB2 hcAMP EC50 uM | CB1 hcAMP EC50 uM |
|---|---|---|
| 1 | 0.001 | >10 |
| 2 | 0.0064 | >10 |

| Example | CB2 hcAMP EC50 uM | CB1 hcAMP EC50 uM |
|---|---|---|
| 3 | 0.0005 | 0.77 |
| 4 | 0.001 | 0.75 |
| 5 | 0.001 | >10 |
| 6 | 0.0036 | >10 |
| 7 | 0.0092 | >10 |
| 8 | 0.0045 | >10 |
| 9 | 0.0016 | 0.363 |
| 10 | 0.0029 | 0.217 |
| 11 | 0.0026 | >10 |
| 12 | 0.0009 | 0.365 |
| 13 | 0.0125 | >10 |
| 14 | 0.0035 | >10 |
| 15 | 0.0022 | 0.336 |
| 16 | 0.0031 | >10 |
| 17 | 0.0266 | >10 |
| 18 | 0.0081 | 0.967 |
| 19 | 0.0274 | >10 |
| 20 | 0.0203 | >10 |
| 21 | 0.1411 | >10 |
| 22 | 0.0021 | >10 |
| 23 | 0.0011 | 0.487 |
| 24 | 0.0034 | >10 |
| 25 | 0.0075 | >10 |
| 26 | 0.001 | >10 |
| 27 | 0.2674 | >10 |
| 28 | 0.0023 | >10 |
| 29 | 0.0486 | >10 |
| 30 | 0.0899 | >10 |
| 31 | 0.056 | >10 |
| 32 | 0.0096 | >10 |
| 33 | 0.0072 | >10 |
| 34 | 0.0453 | >10 |
| 35 | 0.0108 | >10 |
| 36 | 0.2204 | >10 |
| 37 | 0.0236 | >10 |
| 38 | 0.3118 | >10 |
| 39 | 0.3014 | >10 |
| 40 | 0.0061 | >10 |
| 41 | 0.0085 | >10 |
| 42 | 0.0033 | >10 |
| 43 | 0.0264 | >10 |
| 44 | 0.004 | >10 |
| 45 | 0.0012 | >10 |
| 46 | 0.0053 | >10 |
| 47 | 0.0036 | >10 |
| 48 | 0.0017 | >10 |
| 49 | 0.0219 | >10 |
| 50 | 0.0028 | >10 |
| 51 | 0.0021 | >10 |
| 52 | 0.0008 | >10 |
| 53 | 0.0055 | >10 |
| 54 | 0.0012 | >10 |
| 55 | 0.0012 | >10 |
| 56 | 0.011 | >10 |
| 57 | 0.0088 | >10 |
| 58 | 0.0157 | >10 |
| 59 | 0.0009 | >10 |
| 60 | 0.0008 | >10 |
| 61 | 0.0075 | >10 |
| 62 | 0.0148 | >10 |
| 63 | 0.1898 | >10 |
| 64 | 0.1735 | >10 |
| 65 | 0.0119 | >10 |
| 66 | 0.0039 | >10 |
| 67 | 0.0017 | >10 |
| 68 | 0.0004 | >10 |
| 69 | 0.0032 | >10 |
| 70 | 0.0051 | >10 |
| 71 | 0.2135 | >10 |
| 72 | 0.0674 | >10 |
| 73 | 0.0423 | >10 |
| 74 | 0.0018 | >10 |
| 75 | 0.0043 | >10 |
| 76 | 0.0177 | >10 |
| 77 | 0.0582 | >10 |
| 78 | 0.1676 | >10 |
| 79 | 0.0727 | >10 |
| 80 | 0.1594 | >10 |
| 81 | 0.0789 | >10 |
| 82 | 0.0007 | 0.183 |
| 83 | 0.0019 | >10 |
| 84 | 0.0023 | 0.08 |
| 85 | 0.0009 | 0.108 |
| 86 | 0.0866 | >10 |
| 87 | 0.083 | >10 |
| 88 | 0.0017 | >10 |
| 89 | 0.0074 | >10 |
| 90 | 0.0156 | >10 |
| 91 | 0.0069 | >10 |
| 92 | 0.0025 | >10 |
| 93 | 0.0088 | >10 |
| 94 | 0.0028 | >10 |
| 95 | 0.0644 | >10 |
| 96 | 0.0051 | >10 |
| 97 | 0.038 | >10 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula (I) | 3.0 mg |
|---|---|
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:
1. A compound of formula (I)

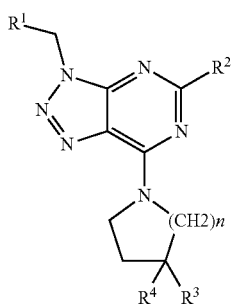

wherein
$R^1$ is haloalkyl, halophenyl, alkoxyphenyl, alkyl-1,2,5-oxadiazolyl, haloalkylphenyl, alkylsulfonylphenyl, halopyridinyl or alkyltetrazolyl;
$R^2$ is cycloalkyl, isopropyl, alkenyl, piperidinyl, alkylamino, azetidinyl, pyrrolidinyl, cycloalkylamino, alkyloxetanylamino, morpholinyl, (cycloalkyl)(alkyl) amino, haloalkyloxy, alkoxy, cycloalkylalkoxy, cycloalkyloxy, oxetanyloxy, alkyloxetanylalkyloxy, alkynyloxy, alkoxyalkoxy, hydroxyalkyloxy, alkylsulfanyl, haloalkylsulfanyl, alkylsulfonyl, hydroxyalkylsulfanyl, hydroxyalkylsulfonyl or alkoxyalkylsulfonyl;
$R^3$ and $R^4$ are independently selected from hydrogen, halogen, hydroxyl, alkylcarbonylamino and alkyl, provided that $R^3$ and $R^4$ are not both hydrogen at the same time; and
n is 1 or 2;
or a pharmaceutically acceptable salt or ester thereof;
provided that (S)-1-[3-(4-Methoxy-benzyl)-5-(2,2,2-trifluoro-ethoxy)-3H-[1,2,3]triazolo[4,5-d]pyrimidin-7-yl]-pyrrolidin-3-ol is excluded.

2. A compound according to claim 1, wherein $R^1$ is halophenyl, haloalkylphenyl or alkylsulfonylphenyl.

3. A compound according to claim 1, wherein $R^1$ is chlorophenyl, trifluoromethylphenyl or methylsulfonylphenyl.

4. A compound according to claim 1, wherein $R^2$ is cycloalkyl, isopropyl, alkylamino, alkoxy, haloalkyloxy or alkylsulfanyl.

5. A compound according to claim 1, wherein $R^2$ is cyclobutyl, isopropyl, tert.-butylamino, pentyloxy, isopropyloxy, trifluoroethyloxy, trifluoropropyloxy, ethylsulfanyl or tert.-butylsulfanyl.

6. A compound according to claim 1, wherein $R^3$ and $R^4$ are independently selected from hydrogen, halogen and hydroxyl.

7. A compound according to claim 1, wherein one of $R^3$ and $R^4$ is hydrogen and the other one is hydroxyl, or wherein $R^3$ and $R^4$ are both halogen at the same time.

8. A compound according to claim 1, wherein one of $R^3$ and $R^4$ is hydrogen and the other one is hydroxyl, or wherein $R^3$ and $R^4$ are both fluorine at the same time.

9. A compound according to claim 1 selected from:
3-[(2-chlorophenyl)methyl]-5-cyclobutyl-7-(3,3-difluoropyrrolidin-1-yl)triazolo[4,5-d]pyrimidine;
5-cyclopropyl-7-(3,3-difluoropyrrolidin-1-yl)-3-[(4-methoxyphenyl)methyl]triazolo[4,5-d]pyrimidine;
3-[(2-chlorophenyl)methyl]-7-(3,3-difluoropyrrolidin-1-yl)-5-propan-2-yltriazolo[4,5-d]pyrimidine;
3-[(2-chlorophenyl)methyl]-5-cyclopropyl-7-(3,3-difluoropyrrolidin-1-yl)triazolo[4,5-d]pyrimidine;
3-[[5-cyclopropyl-7-(3,3-difluoropyrrolidin-1-yl)triazolo[4,5-d]pyrimidin-3-yl]methyl]-4-methyl-1,2,5-oxadiazole;
(3S)-1-[3-[(2-chlorophenyl)methyl]-5-prop-1-en-2-yltriazolo[4,5-d]pyrimidin-7-yl]pyrrolidin-3-ol;
3-[(2-chlorophenyl)methyl]-5,7-di(piperidin-1-yl)triazolo[4,5-d]pyrimidine;
3-[(2-chlorophenyl)methyl]-7-(3,3-difluoropyrrolidin-1-yl)-N-ethyltriazolo[4,5-d]pyrimidin-5-amine;
5-(azetidin-1-yl)-3-[(2-chlorophenyl)methyl]-7-(3,3-difluoropyrrolidin-1-yl)triazolo[4,5-d]pyrimidine;
3-[(2-chlorophenyl)methyl]-7-(3,3-difluoropyrrolidin-1-yl)-5-pyrrolidin-1-yltriazolo[4,5-d]pyrimidine;
3-[(2-chlorophenyl)methyl]-N-cyclobutyl-7-(3,3-difluoropyrrolidin-1-yl)triazolo[4,5-d]pyrimidin-5-amine;
N-tert-butyl-3-[(2-chlorophenyl)methyl]-7-(3,3-difluoropyrrolidin-1-yl)triazolo[4,5-d]pyrimidin-5-amine;
3-[(2-chlorophenyl)methyl]-7-(3,3-difluoropyrrolidin-1-yl)-N-(3-methyloxetan-3-yl)triazolo[4,5-d]pyrimidin-5-amine;
4-[3-[(2-chlorophenyl)methyl]-7-(3,3-difluoropyrrolidin-1-yl)triazolo[4,5-d]pyrimidin-5-yl]morpholine;
N-tert-butyl-3-[(2-chlorophenyl)methyl]-7-(3,3-difluoropyrrolidin-1-yl)-N-methyltriazolo[4,5-d]pyrimidin-5-amine;
3-[(2-chlorophenyl)methyl]-7-(3,3-difluoropyrrolidin-1-yl)-N-(2,2-dimethylpropyl)triazolo[4,5-d]pyrimidin-5-amine;
3-[(2-chlorophenyl)methyl]-7-(3,3-difluoropyrrolidin-1-yl)-N-(oxetan-3-yl)triazolo[4,5-d]pyrimidin-5-amine;
3-[(2-chlorophenyl)methyl]-N-cyclobutyl-7-(3,3-difluoropyrrolidin-1-yl)-N-methyltriazolo[4,5-d]pyrimidin-5-amine;
(3S)-1-[5-(tert-butylamino)-3-[(4-methoxyphenyl)methyl]triazolo[4,5-d]pyrimidin-7-yl]pyrrolidin-3-ol;
N-tert-butyl-7-(3,3-difluoropyrrolidin-1-yl)-3-[(4-methoxyphenyl)methyl]triazolo[4,5-d]pyrimidin-5-amine;
N-[(3S)-1-[5-(tert-butylamino)-3-[(4-methoxyphenyl)methyl]triazolo[4,5-d]pyrimidin-7-yl]pyrrolidin-3-yl]acetamide;
N-tert-butyl-7-(3,3-difluoropyrrolidin-1-yl)-3-[[2-(trifluoromethyl)phenyl]methyl]triazolo[4,5-d]pyrimidin-5-amine;

N-tert-butyl-7-(3,3-difluoropyrrolidin-1-yl)-3-[(2-methylsulfonylphenyl)methyl]triazolo[4,5-d]pyrimidin-5-amine;

N-tert-butyl-3-[(3-chloropyridin-2-yl)methyl]-7-(3,3-difluoropyrrolidin-1-yl)triazolo[4,5-d]pyrimidin-5-amine;

N-tert-butyl-7-(3,3-difluoropyrrolidin-1-yl)-3-[(1-methyltetrazol-5-yl)methyl]triazolo[4,5-d]pyrimidin-5-amine;

N-tert-butyl-7-(3,3-difluoropyrrolidin-1-yl)-3-[(4-methyl-1,2,5-oxadiazol-3-yl)methyl]triazolo[4,5-d]pyrimidin-5-amine;

N-[(3S)-1-[5-(tert-butylamino)-3-[(3-chloropyridin-2-yl)methyl]triazolo[4,5-d]pyrimidin-7-yl]pyrrolidin-3-yl]acetamide;

(3S)-1-[5-(tert-butylamino)-3-[(2-chlorophenyl)methyl]triazolo[4,5-d]pyrimidin-7-yl]pyrrolidin-3-ol;

(3S)-1-[5-(tert-butylamino)-3-[(1-methyltetrazol-5-yl)methyl]triazolo[4,5-d]pyrimidin-7-yl]pyrrolidin-3-ol;

(3S)-1-[5-(tert-butylamino)-3-[(4-methoxyphenyl)methyl]triazolo[4,5-d]pyrimidin-7-yl]-3-methylpyrrolidin-3-ol;

(3R)-1-[5-(tert-butylamino)-3-[(4-methoxyphenyl)methyl]triazolo[4,5-d]pyrimidin-7-yl]-3-methylpyrrolidin-3-ol;

(3S)-1-[3-[(2-chlorophenyl)methyl]-5-morpholin-4-yltriazolo[4,5-d]pyrimidin-7-yl]-3-methylpyrrolidin-3-ol;

(3S)-3-methyl-1-[5-morpholin-4-yl-3-[[2-(trifluoromethyl)phenyl]methyl]triazolo[4,5-d]pyrimidin-7-yl]pyrrolidin-3-ol;

(3S)-1-[3-[(3-chloropyridin-2-yl)methyl]-5-morpholin-4-yltriazolo[4,5-d]pyrimidin-7-yl]-3-methylpyrrolidin-3-ol;

(3S)-3-methyl-1-[3-[(3-methyl-1,2,4-oxadiazol-5-yl)methyl]-5-morpholin-4-yltriazolo[4,5-d]pyrimidin-7-yl]pyrrolidin-3-ol;

(3R)-1-[3-[(2-chlorophenyl)methyl]-5-morpholin-4-yltriazolo[4,5-d]pyrimidin-7-yl]-3-methylpyrrolidin-3-ol;

(3R)-3-methyl-1-[5-morpholin-4-yl-3-[[2-(trifluoromethyl)phenyl]methyl]triazolo[4,5-d]pyrimidin-7-yl]pyrrolidin-3-ol;

(3R)-3-methyl-1-[3-[(2-methylsulfonylphenyl)methyl]-5-morpholin-4-yltriazolo[4,5-d]pyrimidin-7-yl]pyrrolidin-3-ol;

(3R)-3-methyl-1-[3-[(3-methyl-1,2,4-oxadiazol-5-yl)methyl]-5-morpholin-4-yltriazolo[4,5-d]pyrimidin-7-yl]pyrrolidin-3-ol;

3-[(2-chlorophenyl)methyl]-7-(3,3-difluoropyrrolidin-1-yl)-5-(2,2,2-trifluoroethoxy)triazolo[4,5-d]pyrimidine;

3-[(2-chlorophenyl)methyl]-7-(3,3-difluoropyrrolidin-1-yl)-5-(1,1,1-trifluoropropan-2-yloxy)triazolo[4,5-d]pyrimidine;

3-[(2-chlorophenyl)methyl]-7-(3,3-difluoropyrrolidin-1-yl)-5-[(2S)-1,1,1-trifluoropropan-2-yl]oxytriazolo[4,5-d]pyrimidine;

3-[(2-chlorophenyl)methyl]-5-(2,2-difluoroethoxy)-7-(3,3-difluoropyrrolidin-1-yl)triazolo[4,5-d]pyrimidine;

3-[(2-chlorophenyl)methyl]-7-(3,3-difluoropyrrolidin-1-yl)-5-ethoxytriazolo[4,5-d]pyrimidine;

5-butoxy-3-[(2-chlorophenyl)methyl]-7-(3,3-difluoropyrrolidin-1-yl)triazolo[4,5-d]pyrimidine;

3-[(2-chlorophenyl)methyl]-7-(3,3-difluoropyrrolidin-1-yl)-5-(2-fluoroethoxy)triazolo[4,5-d]pyrimidine;

3-[(2-chlorophenyl)methyl]-5-(cyclopropylmethoxy)-7-(3,3-difluoropyrrolidin-1-yl)triazolo[4,5-d]pyrimidine;

3-[(2-chlorophenyl)methyl]-5-cyclobutyloxy-7-(3,3-difluoropyrrolidin-1-yl)triazolo[4,5-d]pyrimidine;

3-[(2-chlorophenyl)methyl]-7-(3,3-difluoropyrrolidin-1-yl)-5-(oxetan-3-yloxy)triazolo[4,5-d]pyrimidine;

3-[(2-chlorophenyl)methyl]-7-(3,3-difluoropyrrolidin-1-yl)-5-[(3-methyloxetan-3-yl)methoxy]triazolo[4,5-d]pyrimidine;

3-[(2-chlorophenyl)methyl]-7-(3,3-difluoropyrrolidin-1-yl)-5-[(2R)-1,1,1-trifluoropropan-2-yl]oxytriazolo[4,5-d]pyrimidine;

3-[(2-chlorophenyl)methyl]-7-(3,3-difluoropyrrolidin-1-yl)-5-(2,2-dimethylpropoxy)triazolo[4,5-d]pyrimidine;

3-[(2-chlorophenyl)methyl]-5-(2,2-difluoropropoxy)-7-(3,3-difluoropyrrolidin-1-yl)triazolo[4,5-d]pyrimidine;

3-[(2-chlorophenyl)methyl]-7-(3,3-difluoropyrrolidin-1-yl)-5-(2-methylpropoxy)triazolo[4,5-d]pyrimidine;

3-[(2-chlorophenyl)methyl]-7-(3,3-difluoropyrrolidin-1-yl)-5-propan-2-yloxytriazolo[4,5-d]pyrimidine;

3-[(2-chlorophenyl)methyl]-7-(3,3-difluoropyrrolidin-1-yl)-5-prop-2-ynoxytriazolo[4,5-d]pyrimidine;

3-[(2-chlorophenyl)methyl]-7-(3,3-difluoropyrrolidin-1-yl)-5-(1-methoxypropan-2-yloxy)triazolo[4,5-d]pyrimidine;

1-[3-[(2-chlorophenyl)methyl]-7-(3,3-difluoropyrrolidin-1-yl)triazolo[4,5-d]pyrimidin-5-yl]oxy-2-methylpropan-2-ol;

3-[(2-chlorophenyl)methyl]-7-(3,3-difluoropyrrolidin-1-yl)-5-propoxytriazolo[4,5-d]pyrimidine;

(3S)-1-[3-[(2-chlorophenyl)methyl]-5-(2,2,2-trifluoroethoxy)triazolo[4,5-d]pyrimidin-7-yl]pyrrolidin-3-ol;

(3S)-1-[5-(2,2,2-trifluoroethoxy)-3-[[2-(trifluoromethyl)phenyl]methyl]triazolo[4,5-d]pyrimidin-7-yl]pyrrolidin-3-ol;

(3S)-1-[3-[(2-chlorophenyl)methyl]-5-propan-2-yloxytriazolo[4,5-d]pyrimidin-7-yl]pyrrolidin-3-ol;

(3S)-1-[3-[(2-methylsulfonylphenyl)methyl]-5-propan-2-yloxytriazolo[4,5-d]pyrimidin-7-yl]pyrrolidin-3-ol;

(3S)-1-[3-[(1-methyltetrazol-5-yl)methyl]-5-propan-2-yloxytriazolo[4,5-d]pyrimidin-7-yl]pyrrolidin-3-ol;

7-(3,3-difluoropyrrolidin-1-yl)-5-(2,2-dimethylpropoxy)-3-[(1-methyltetrazol-5-yl)methyl]triazolo[4,5-d]pyrimidine;

7-(3,3-difluoropyrrolidin-1-yl)-5-(2,2-dimethylpropoxy)-3-[(2-methylsulfonylphenyl)methyl]triazolo[4,5-d]pyrimidine;

3-[[7-(3,3-difluoropyrrolidin-1-yl)-5-(2,2-dimethylpropoxy)triazolo[4,5-d]pyrimidin-3-yl]methyl]-4-methyl-1,2,5-oxadiazole;

7-(3,3-difluoropyrrolidin-1-yl)-3-[[2-(trifluoromethyl)phenyl]methyl]-5-[(2S)-1,1,1-trifluoropropan-2-yl]oxytriazolo[4,5-d]pyrimidine;

7-(3,3-difluoropyrrolidin-1-yl)-3-[(2-methylsulfonylphenyl)methyl]-5-[(2S)-1,1,1-trifluoropropan-2-yl]oxytriazolo[4,5-d]pyrimidine;

3-[(3-chloropyridin-2-yl)methyl]-7-(3,3-difluoropyrrolidin-1-yl)-5-[(2S)-1,1,1-trifluoropropan-2-yl]oxytriazolo[4,5-d]pyrimidine;

2-[[7-(3,3-difluoropyrrolidin-1-yl)-5-[(2S)-1,1,1-trifluoropropan-2-yl]oxytriazolo[4,5-d]pyrimidin-3-yl]methyl]-5-methyl-1,3,4-oxadiazole;

5-[[7-(3,3-difluoropyrrolidin-1-yl)-5-[(2S)-1,1,1-trifluoropropan-2-yl]oxytriazolo[4,5-d]pyrimidin-3-yl]methyl]-3-methyl-1,2,4-oxadiazole;

7-(3,3-difluoropyrrolidin-1-yl)-3-[(1-methyltetrazol-5-yl)methyl]-5-[(2S)-1,1,1-trifluoropropan-2-yl]oxytriazolo[4,5-d]pyrimidine;

3-[[7-(3,3-difluoropyrrolidin-1-yl)-5-[(2S)-1,1,1-trifluoropropan-2-yl]oxytriazolo[4,5-d]pyrimidin-3-yl]methyl]-4-methyl-1,2,5-oxadiazole;

7-(3,3-difluoropyrrolidin-1-yl)-5-[(2S)-1,1,1-trifluoro-propan-2-yl]oxy-3-(3,3,3-trifluoropropyl)triazolo[4,5-d]pyrimidine;

3-[(1-cyclopropyltetrazol-5-yl)methyl]-7-(3,3-difluoro-pyrrolidin-1-yl)-5-[(2S)-1,1,1-trifluoropropan-2-yl]oxytriazolo[4,5-d]pyrimidine;

N-[(3S)-1-[3-[(2-chlorophenyl)methyl]-5-(2,2-dimethyl-propoxy)triazolo[4,5-d]pyrimidin-7-yl]pyrrolidin-3-yl]acetamide;

N-[(3S)-1-[3-[(3-chloropyridin-2-yl)methyl]-5-(2,2-dimethylpropoxy)triazolo[4,5-d]pyrimidin-7-yl]pyrrolidin-3-yl]acetamide;

N-[(3S)-1-[5-(2,2-dimethylpropoxy)-3-[(4-methyl-1,2,5-oxadiazol-3-yl)methyl]triazolo[4,5-d]pyrimidin-7-yl]pyrrolidin-3-yl]acetamide;

N-[(3S)-1-[3-[(2-chlorophenyl)methyl]-5-[(2S)-1,1,1-tri-fluoropropan-2-yl]oxytriazolo[4,5-d]pyrimidin-7-yl]pyrrolidin-3-yl]acetamide;

N-[(3S)-1-[3-[[2-(trifluoromethyl)phenyl]methyl]-5-[(2S)-1,1,1-trifluoropropan-2-yl]oxytriazolo[4,5-d]pyrimidin-7-yl]pyrrolidin-3-yl]acetamide;

3-[(2-chlorophenyl)methyl]-7-(3,3-difluoropyrrolidin-1-yl)-5-ethylsulfanyltriazolo[4,5-d]pyrimidine;

3-[(2-chlorophenyl)methyl]-7-(3,3-difluoropyrrolidin-1-yl)-5-(2,2,2-trifluoroethyl sulfanyl)triazolo[4,5-d]pyrimidine;

3-[(2-chlorophenyl)methyl]-7-(3,3-difluoropyrrolidin-1-yl)-5-propan-2-ylsulfanyltriazolo[4,5-d]pyrimidine;

5-tert-butylsulfanyl-3-[(2-chlorophenyl)methyl]-7-(3,3-difluoropyrrolidin-1-yl)triazolo[4,5-d]pyrimidine;

3-[(2-chlorophenyl)methyl]-7-(3,3-difluoropyrrolidin-1-yl)-5-ethylsulfonyltriazolo[4,5-d]pyrimidine;

5-benzylsulfonyl-3-[(2-chlorophenyl)methyl]-7-(3,3-difluoropyrrolidin-1-yl)triazolo[4,5-d]pyrimidine;

3-[(2-chlorophenyl)methyl]-7-(3,3-difluoropyrrolidin-1-yl)-5-propan-2-ylsulfonyltriazolo[4,5-d]pyrimidine;

2-[3-[(2-chlorophenyl)methyl]-7-(3,3-difluoropyrrolidin-1-yl)triazolo[4,5-d]pyrimidin-5-yl]sulfanylethanol;

1-[3-[(2-chlorophenyl)methyl]-7-(3,3-difluoropyrrolidin-1-yl)triazolo[4,5-d]pyrimidin-5-yl]sulfanylpropan-2-ol;

5-butylsulfanyl-3-[(2-chlorophenyl)methyl]-7-(3,3-difluoropyrrolidin-1-yl)triazolo[4,5-d]pyrimidine;

3-[(2-chlorophenyl)methyl]-7-(3,3-difluoropyrrolidin-1-yl)-5-(2-methylpropylsulfanyl)triazolo[4,5-d]pyrimidine;

5-butylsulfonyl-3-[(2-chlorophenyl)methyl]-7-(3,3-difluoropyrrolidin-1-yl)triazolo[4,5-d]pyrimidine;

3-[(2-chlorophenyl)methyl]-7-(3,3-difluoropyrrolidin-1-yl)-5-(2-methylpropylsulfonyl)triazolo[4,5-d]pyrimidine;

1-[3-[(2-chlorophenyl)methyl]-7-(3,3-difluoropyrrolidin-1-yl)triazolo[4,5-d]pyrimidin-5-yl]sulfonylpropan-2-ol;

3-[(2-chlorophenyl)methyl]-7-(3,3-difluoropyrrolidin-1-yl)-5-(2-methoxyethyl sulfonyl)triazolo[4,5-d]pyrimidine; and N-[(3S)-1-[5-(tert-butylamino)-3-[(2-chlorophenyl)methyl]triazolo[4,5-d]pyrimidin-7-yl]pyrrolidin-3-yl]acetamide.

10. A compound according to claim 1 selected from
3-[(2-chlorophenyl)methyl]-5-cyclobutyl-7-(3,3-difluo-ropyrrolidin-1-yl)triazolo[4,5-d]pyrimidine;

3-[(2-chlorophenyl)methyl]-7-(3,3-difluoropyrrolidin-1-yl)-5-propan-2-yltriazolo[4,5-d]pyrimidine;

N-tert-butyl-3-[(2-chlorophenyl)methyl]-7-(3,3-difluoro-pyrrolidin-1-yl)triazolo[4,5-d]pyrimidin-5-amine;

N-tert-butyl-7-(3,3-difluoropyrrolidin-1-yl)-3-[(2-meth-ylsulfonylphenyl)methyl]triazolo[4,5-d]pyrimidin-5-amine;

3-[(2-chlorophenyl)methyl]-7-(3,3-difluoropyrrolidin-1-yl)-5-(2,2-dimethylpropoxy)triazolo[4,5-d]pyrimidine;

3-[(2-chlorophenyl)methyl]-7-(3,3-difluoropyrrolidin-1-yl)-5-(2-methylpropoxy)triazolo[4,5-d]pyrimidine;

(3S)-1-[3-[(2-chlorophenyl)methyl]-5-(2,2,2-trifluoroeth-oxy)triazolo[4,5-d]pyrimidin-7-yl]pyrrolidin-3-ol;

7-(3,3-difluoropyrrolidin-1-yl)-3-[[2-(trifluoromethyl)phenyl]methyl]-5-[(2S)-1,1,1-trifluoropropan-2-yl]oxytriazolo[4,5-d]pyrimidine;

3-[(2-chlorophenyl)methyl]-7-(3,3-difluoropyrrolidin-1-yl)-5-ethylsulfanyltriazolo[4,5-d]pyrimidine; and 5-tert-butylsulfanyl-3-[(2-chlorophenyl)methyl]-7-(3,3-difluoropyrrolidin-1-yl)triazolo[4,5-d]pyrimidine.

11. A process for the preparation of a compound of formula (I) according to claim 1, comprising one of the following steps:

(a) the reaction of a compound of formula (A1)

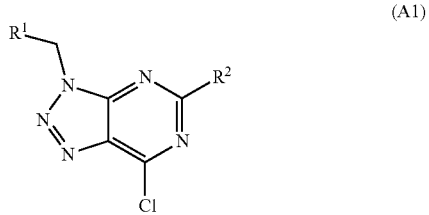

(A1)

in the presence of a compound of formula (A2)

(A2)

wherein $R^2$ is isopropyl, cycloalkyl or alkenyl and $R^1$, $R^3$, $R^4$ and n are as defined in claim 1;

(b) the reaction of a compound of formula (B1)

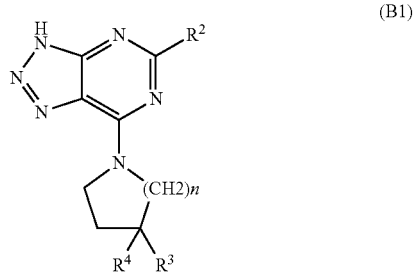

(B1)

in the presence of $R^1CH_2X$ wherein X is a halogen, a hydroxyl or a sulfonate group, wherein $R^2$ is isopropyl, cycloalkyl or alkenyl and wherein $R^3$ to $R^4$ and n are as defined in claim 1; or (c) the reaction of a compound of formula (C1)

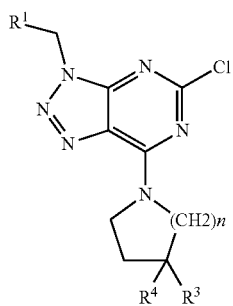

(C1)

in the presence of $R^2$—H wherein $R^2$ is piperidinyl, alkylamino, azetidinyl, pyrrolidinyl, cycloalkylamino, alkyloxetanylamino, morpholinyl, (cycloalkyl)(alkyl)amino, haloalkyloxy, alkoxy, cycloalkylalkoxy, cycloalkyloxy, oxetanyloxy, alkyloxetanylalkyloxy, alkynyloxy, alkoxyalkoxy, hydroxyalkyloxy, alkylsulfanyl, haloalkylsulfanyl, alkylsulfonyl, hydroxyalkylsulfanyl, hydroxyalkylsulfonyl or alkoxyalkylsulfonyl and wherein $R^1$, $R^3$, $R^4$ and n are as defined in claim 1.

12. A pharmaceutical composition comprising a compound in accordance with claim 1 and a therapeutically inert carrier.

13. A method for the treatment of pain, atherosclerosis, age-related macular degeneration; diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischema, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis, which method comprises administering an effective amount of a compound as defined in claim 1 to a patient in need thereof.

14. The method of claim 13 wherein the treatment is for diabetic retinopathy.

* * * * *